United States Patent [19]
Briggs et al.

[11] Patent Number: 6,068,976
[45] Date of Patent: *May 30, 2000

[54] MODULATORS OF OB GENE AND SCREENING METHODS THEREFOR

[75] Inventors: Michael R. Briggs, Downingtown, Pa.; Johan Auwerx, Millionfosse, France; Piet de Vos, Zingem; Bart Staels, Kraainem, both of Belgium; Glenn E. Croston; Stephen G. Miller, both of San Diego, Calif.

[73] Assignee: Ligand Pharmaceuticals Incorporated, San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/618,100

[22] Filed: Mar. 19, 1996

Related U.S. Application Data

[63] Continuation-in-part of application No. 08/558,588, Oct. 30, 1995, abandoned, which is a continuation-in-part of application No. 08/510,584, Aug. 2, 1995, abandoned, which is a continuation-in-part of application No. 08/418,096, Apr. 5, 1995, abandoned, which is a continuation-in-part of application No. 08/408,584, Mar. 20, 1995, abandoned.

[60] Provisional application No. 60/008,601, Dec. 14, 1995, provisional application No. 60/007,721, Nov. 30, 1995, and provisional application No. 60/007,390, Nov. 21, 1995.

[51] Int. Cl.⁷ .................................................. C12Q 1/68
[52] U.S. Cl. .............................. 435/6; 435/4; 435/320.1; 536/24.1; 536/23.1; 536/23.5
[58] Field of Search .................... 536/24.1, 23.5, 536/23.1; 435/320.1, 4, 6

[56] References Cited

U.S. PATENT DOCUMENTS 5,698,389 12/1997 de la Brousse et al. .................. 435/4

FOREIGN PATENT DOCUMENTS 0 764 722 A2  3/1997  European Pat. Off.
WO 97/18228   5/1997  WIPO.

OTHER PUBLICATIONS

S. Faisst and S. Meyer, Compilation of vertebrate–encoded transcription factors, Jan. 1992, Nucleic Acids Research vol. 20, No. 1, pp. 3–26.

P. Tontonoz, et al., mPPARγ2: tissue–specific regulator of an adipocyte enhancer, 1994, Genes & Development, vol. 8, pp. 1224–1234.

De Vos, et al. *J. Biol. Chem.* 270(27):15958–15961 (1995).

Gong, et al. *J. Biol. Chem.* 271(8):3971–3974 (1996).

Isse, et al. *J. Biol. Chem.* 270(46):27728–27733 (1995).

Saladin, et al. *Nature* 377(6549):527–529 (1995).

*Primary Examiner*—Remy Yucel
*Attorney, Agent, or Firm*—Lyon & Lyon LLP

[57] ABSTRACT

This invention relates to the isolation and cloning of the promoter and other control regions of a human ob gene. It provides a method for identifying and screening for agents useful for the treatment of diseases and pathological conditions affected by the level of expression of an ob gene. These agents interact directly or indirectly with the promoter or other control regions of the ob gene. A PPARγ agonist, BRL49653, has been identified to be useful in treating anorexia, cachexia, and other diseases characterized by insufficient food intake or body weight loss. Modulators of ob gene expression may be used to treat other diseases such as obesity, diabetes, hypertension, cardiovascular diseases and infertility.

42 Claims, 21 Drawing Sheets

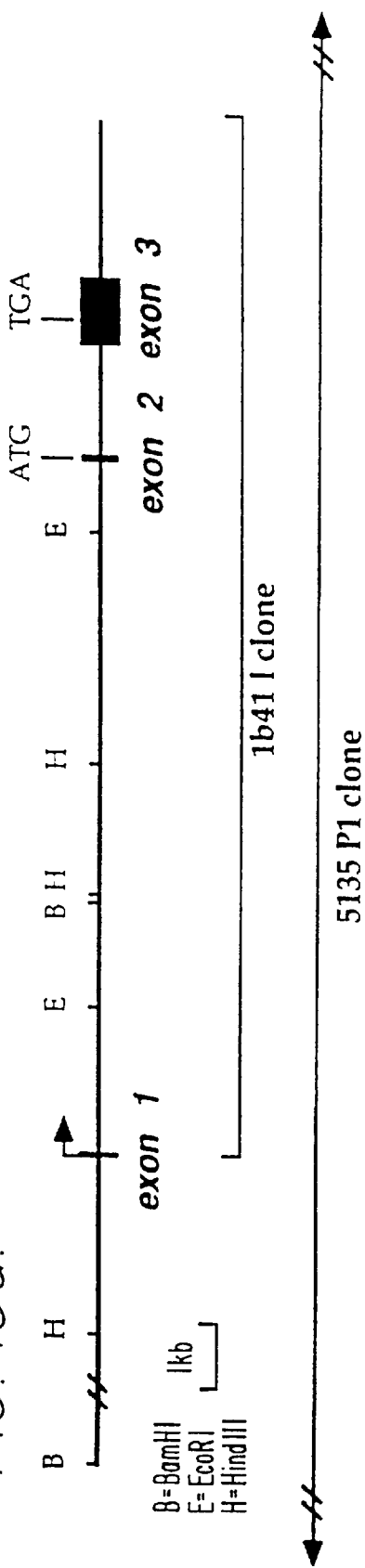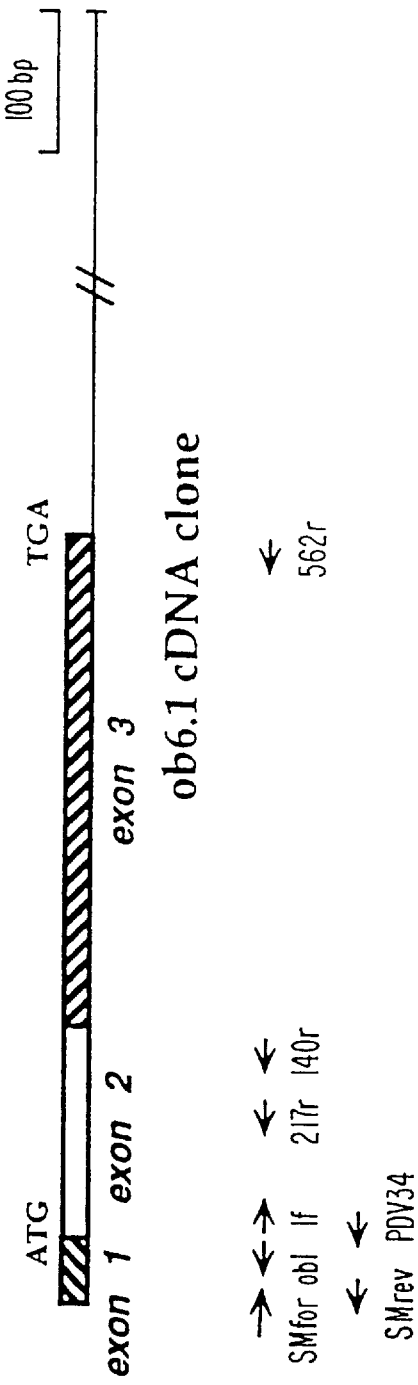

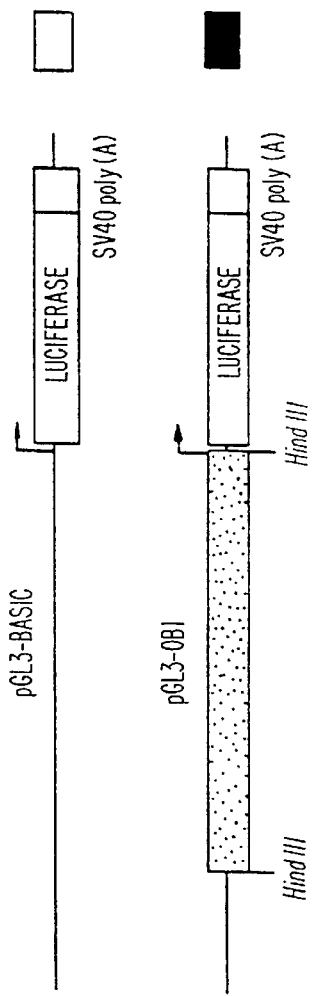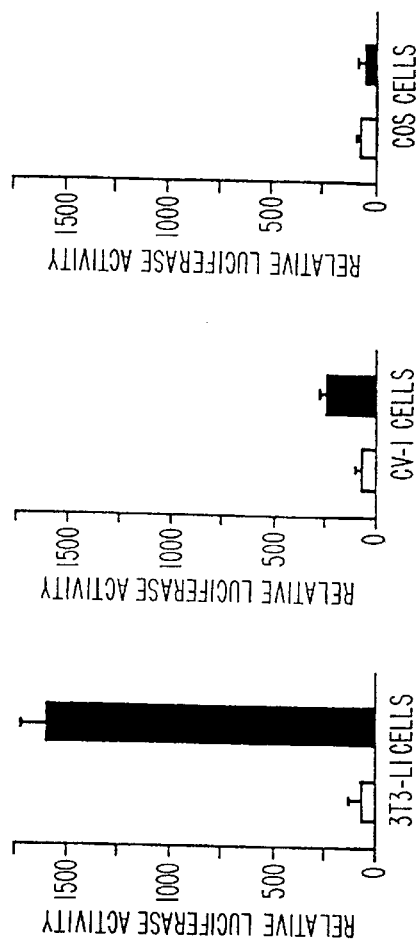

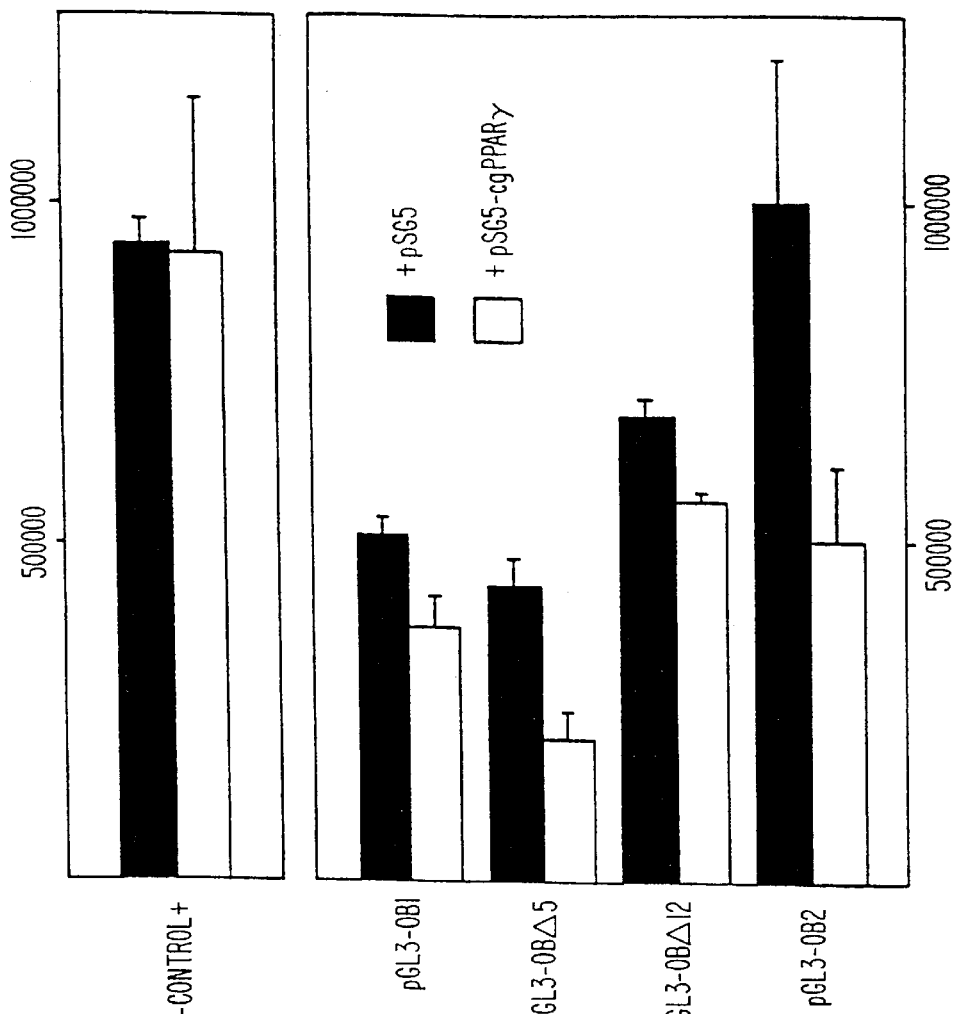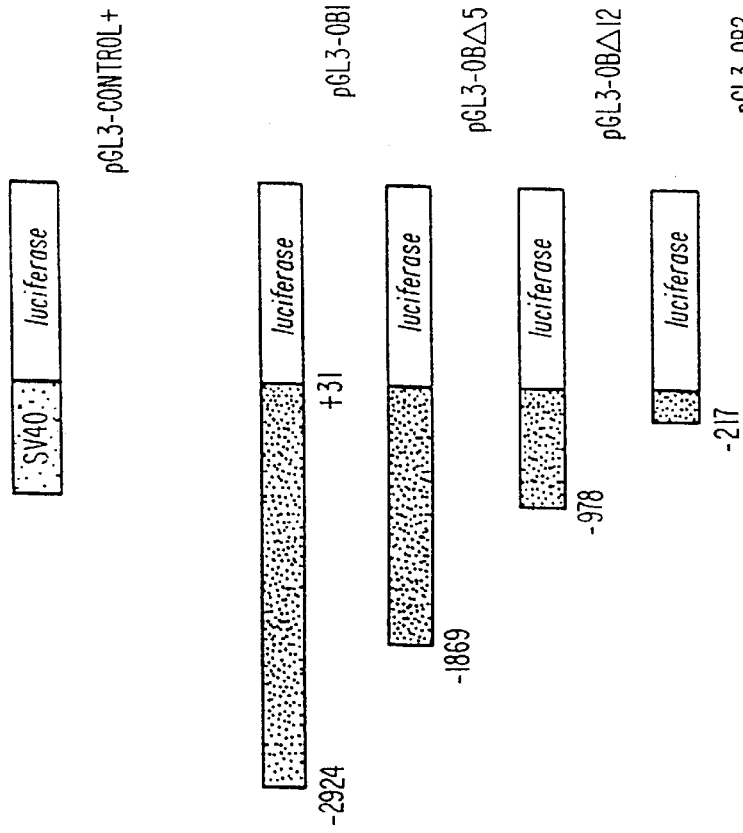

MODULATORS OF OB GENE AND SCREENING METHODS THEREFOR

CROSS REFERENCE TO RELATED APPLICATIONS

This application is a continuation-in-part of U.S. application Ser. No. 08/558,588 filed Oct. 30, 1995, abandoned, which is a continuation-in-part of U.S. application Ser. No. 08/510,584 filed Aug. 2, 1995, abandoned, which is a continuation-in-part of U.S. application Ser. No. 08/418,096 filed Apr. 5, 1995, abandoned, which is a continuation-in-part of U.S. application Ser. No. 08/408,584 filed Mar. 20, 1995, abandoned, the disclosure of which are incorporated by reference herein, including drawings, tables and sequence listings.

Other priority applications include provisional applications entitled "Modulators of ob Gene and Screening Methods Therefor," filed by Briggs et al. on Dec. 14, 1995 (Ser. No. 60/008,601), Nov. 30, 1995 (Ser. No. 60/007,721), and Nov. 21, 1995 (Ser. No. 60/007,390), the disclosure of which are incorporated by reference herein, including drawings, tables and sequence listings.

FIELD OF THE INVENTION

This invention relates to a method for screening for agents useful for treatment of diseases and pathological conditions affected by ob genes, and agents and compositions identified using such screening method. This invention also relates to regulatory elements and promoter sequences which serve to promote transcription of the ob gene.

BACKGROUND OF THE INVENTION

Obesity is usually defined as a body weight more than 20% in excess of the ideal body weight. Obesity is associated with an increased risk for cardiovascular disease, diabetes and an increased mortality rate (see Grundy et al., *Disease-a-Month* 36:645–696, 1990). Treatment for obesity includes diet, exercise and surgery (Leibel, R. L. et al., *New England Journal of Medicine* 332:621–628, 1995).

At least five single-gene mutations resulting in obesity have been described in mice, implicating genetic factors in the etiology of obesity (Friedman et al., *Cell* 69:217–220, 1990). In the ob mouse, a single gene mutation, obese, results in profound obesity, which is accompanied by diabetes (Friedman et al., *Genomics* 11:1054–1062, 1991). Cross-circulation experiments have suggested that ob mice are deficient of a blood-borne factor regulating nutrient intake and energy metabolism (Coleman, D. L., *Diabetologia* 14:141–148, 1978).

Zhang et al., *Nature* 372:425–432, 1994, not admitted to be prior art, describe cloning and sequencing the mouse ob gene and its human homologue. They indicate that the ob gene is exclusively expressed in white adipose tissue.

SUMMARY OF THE INVENTION

Loss of appetite, diminished food intake, and loss of body weight are problems associated with many diseases. In the scope of the present invention it has been found that a down regulator of ob gene expression, BRL49653, i.e. 5-[[4-[2-(methyl-2-pyridinylamino)ethoxy]phenyl]methyl]-2,4-thiazolidinedione, has the properties of increasing food intake and body weight in rats. The administration of an effective amount of an ob gene down regulator will be able to treat a patient suffering from anorexia, cachexia and other wasting diseases characterized by loss of appetite, diminished food intake or body weight loss.

Also in the scope of the present invention, it has been found that up regulators of ob gene expression, glucocorticoids, have the properties of decreasing food consumption and body weight gain in rats. The administration of an effective amount of an ob gene up regulator will be able to treat a patient suffering from excessive food consumption and obesity, and related pathological conditions such as type II adult onset diabetes, infertility (Chehab, et al. *Nature Genetics,* 12:318–320, 1996, not admitted to be prior art), hypercholesterolemia, hyperlipidemia, cardiovascular diseases and hypertension.

By "ob gene" is meant a gene encoding a contiguous amino acid sequence sharing about at least 60% (preferably 75%, and more preferably 95%) identity with the human ob gene amino acid sequence disclosed on page 430 of Zhang et al., *Nature* 372:425–432, 1994, including, but not limited to, the human ob gene and the mouse ob gene disclosed in Zhang et al. id.

Without being bound by any theory, Applicant proposes that the effects of BRL49653 and glucocorticoids on food intake and body weight mass are mediated through the level of ob gene expression. Therefore, body weight homeostasis may be modulated by compounds regulating the expression of ob gene. Some of these compounds are disclosed in this application. Others will be identified by the methods disclosed in this application.

Accordingly, the present invention is also related to the isolation, cloning and identification of the promoter and other regulatory elements of the ob gene and the use of ob gene control regions to screen for agents that modulate ob gene expression and thence use these modulators as lead compounds to design or search for other drugs to treat disease related to the level of ob gene expression. The isolated ob gene control regions have utility in constructing in vitro and in vivo experimental models for studying the modulation of ob gene expression and assaying for modulators of ob gene expression. Such experimental models make it possible to screen large collections of natural, semisynthetic, or synthetic compounds for therapeutic agents that affect ob gene expression.

The ob gene modulators identified by the methods of this invention may be used to control a variety of physiological or biochemical conditions in animals (esp. mammals) such as the level of metabolism, body weight, food intake, oxygen consumption, body temperature, serum insulin level, serum glucose level, body fat content (versus muscle content) and the level of physical activities. Such modulators are useful in treating a host with abnormal levels of ob gene expression, as well as those having normal levels of ob gene expression. The ob gene modulators may also be used to treat diseases and conditions affected by the level of ob gene expression, such as, but not limited to, obesity, hypercholesterolemia, hyperlipidemia, cardiovascular diseases, hypertension, diabetes, infertility, anorexia, cachexia and other wasting diseases characterized by loss of appetite, diminished food intake or body weight loss. The modulators are useful in mimicking human diseases or conditions in animals relating to the level of ob gene expression, such as, obesity, hypercholesterolemia, hyperlipidemia, cardiovascular diseases, hypertension, diabetes, infertility, anorexia, cachexia and other wasting diseases characterized by loss of appetite, diminished food intake or body weight loss. Such modulators of ob gene expression may be used to increase circulating levels of ob protein (i.e. leptin), the physiological consequences of which include the normalization of insulin and glucose levels (Pelleymounter, M. A. et al. *Science* 269:540–543, 1995; Halaas, J. L. et al. *Science* 269:543–546, 1995; Campfield, L. A. et al. *Science* 269:546–549, 1995; not admitted to be prior art). The modulators may be used in experimental testing of ob gene modulators for veterinary uses, including, but not limited to, controlling the body weight of animals and the fat content of meat.

Thus, in one aspect, the present invention is directed to an isolated, purified, enriched or recombinant nucleic acid containing a control region of a mammalian ob gene from, including, but not limited to, human, rat, mouse, pig, cattle, dog, or cat. In a preferred embodiment, the control region is from the human ob gene.

By "control region" is meant a nucleic acid sequence capable of, required for, assisting or impeding initiating, terminating, or otherwise regulating the transcription of a gene, including, but not limited to, promoter, enhancer, silencer and other regulatory elements (e.g. those regulating pausing or anti-termination). A positive transcription element increases the transcription of the ob gene. A negative transcription element decreases the transcription of the ob gene. The term "control region" does not include the initiation or termination codons and other sequences already described in Zhang et al., supra. A control region also includes a nucleic acid sequence that may or may not be sufficient by itself to initiate, terminate, or otherwise regulate the transcription, yet is able to do so in combination or coordination with other nucleic acid sequences. A control region can be in nontranscribed regions of a gene, introns or exons. A control region can be in the 5' upstream region or the 3' downstream region to the amino acid coding sequence. A control sequence can be a single regulatory element from a gene. A control region can also have several regulatory elements from a gene linked together. These several regulatory elements can be linked in a way that is substantially the same as in nature or in an artificial way.

A control region in introns and exons may also be involved with regulating the translation of an ob protein, e.g. splicing, processing heteronuclear ribonucleoprotein particles, translation initiation and others described in Oxender, et al. *Proc. Natl. Acad. Sci. USA* 76:5524 (1979) and Yanofsy, *Nature* 289:751–758, (1981).

A control region of this invention is isolated or cloned from a mammalian ob gene. It is distinguished from control regions disclosed in the prior art in that it contains a regulatory element of novel or unique nucleic acid sequence for the ob gene, a known regulatory element set in a novel or unique nucleic acid sequence context for the ob gene, or a few known regulatory elements linked in a novel or unique way for the ob gene.

A nucleic acid of this invention can be single stranded or double stranded, DNA or RNA, including those containing modified nucleotides known to one skilled in the art. The complementary strand of an identified sequence is contemplated herein.

In a preferred embodiment, the nucleic acid contains the entire oh gene, including the control regions and the amino acid coding region.

In another preferred embodiment, the nucleic acid does not contain the intron between the first two exons of an oh gene or portions of the intron.

In yet another preferred embodiment, the nucleic acid contains a control region cloned in a P1 plasmid, such as one of the three P1 vectors (5135, 5136, and 5137) in bacterial strain N8-3529, deposited at ATCC (American Type Culture Collection, 10801 University Boulevard, Manassas, Va. 20110-2209) on Mar. 17, 1995 (accession numbers 69761, 69762, and 69763, respectively), e.g. from the sequence 5' to exon 1 in the P1 clones.

In other preferred embodiments, the control region is a promoter capable of initiating the transcription of the ob gene.

By "promoter" is meant a DNA regulatory region capable of binding directly or indirectly to RNA polymerase in a cell and initiating transcription of a downstream (3' direction) coding sequence. A preferred promoter of this invention contains a sequence from nucleotide −217 to the transcription initiation site of the human ob gene or a portion (e.g. at least 60 contiguous nucleotides) of that sequence. A promoter of a DNA construct, including an oligonucleotide sequence according to the present invention may be linked to a heterologous gene when the presence of the promoter influences transcription from the heterologous gene, including genes for reporter sequences such as growth hormone, luciferase, chloramphenicol acetyl transferase, β-galactosidase secreted placental alkaline phosphatase and other secreted enzyme reporters.

Alternatively, the control region is a positive transcription element capable of up regulating or a negative transcription element capable of down regulating the transcription of the ob gene, e.g. containing a negative transcription element between nucleotide −978 and −217 of the human ob gene or between nucleotide −1869 and −217 of the human ob gene.

The control region may contain at least 100, 60, 30, 12, 8 or 6 contiguous nucleotides from the 5' non-coding sequence or an intron of the ob gene. In a further preferred embodiment, the control region is from the region 5' upstream of the transcription initiation site of the human ob gene, a region between the transcription initiation site of the human ob gene and the HindIII site about 3 kb upstream, a region between the first two exons of the human ob gene, Seq. ID No. 1, 2, 3 or 4, or a region from nucleotide −217 to −1, −978 to −217 or −1869 to −217 of the human ob gene. In yet another further preferred embodiment, the contiguous nucleic acid sequence contains a PPRE, RXRE, GRE, insulin response element, C/EBP binding site, Oct-1 binding site, SP1 binding site, AP-1 binding site, AP-2 binding site, serum response element, CAMP response element, or NFκB site, including, but not limited to, those existing in Seq. ID No. 1, 3 or 4.

The ob gene control regions described herein may be used to prepare antisense molecules against and ribozymes that cleave transcripts from the genomic ob sequence, thus interfering or inhibiting RNA processing or translation of the ob gene. Such antisense molecules and ribozymes down regulate the expression of the ob gene.

Antisense nucleic acids of this invention are DNA or RNA molecules that are complementary to at least a portion of a specific mRNA molecule and hybridize to that mRNA in the cell, forming a double-stranded form. Antisense methods have been used to inhibit the expression of many genes in vitro (Marcus-Sekura, *Anal. Biochem.* 172:289–295, 1988; Hambor et al., *J. Exp. Med.*, 168:1237–1245, 1988).

Ribozymes of this invention are RNA molecules possessing the ability to specifically cleave other single-stranded RNA molecules (Cech, *J. Am. Med. Assoc.*, 260:3030–3034 (1988). Ribozymes capable of modulating the expression of an ob gene may be designed and synthesized with methods known to one skilled in the art such as those disclosed in Stinchcomb, et al. "Method and Reagent for Inhibiting the Expression of Disease Related Genes," WO 95/23225.

The invention also features recombinant nucleic acid comprising a control region of the mammalian oh gene and a nucleic acid sequence (i.e., a reporter sequence), preferably inserted in a vector (virus vector or plasmid vector), also preferably in a cell or an organism. The control region and the reporter sequence are operationally linked so that the control region, such as a promoter, is effective to initiate, terminate or regulate the transcription or translation of the reporter sequence. The recombinant nucleic acid may further comprise a transcriptional termination region functional in a cell.

In preferred embodiments, a human ob gene control region (e.g. promoter) is selected, the control region and the reporter sequence are inserted in a vector. In further preferred embodiments, the promoter contains the region from the 5' HindIII site to the transcription initiation site of Exon 1 in FIG. 9 (i.e. from nucleotide −2921 to −1) or from nucleotide −217 to −1 of the human ob gene. Exemplary recombinant nucleic acids are pGL3B-OB1, pGL3B-OB2, pGL3B-OB3 and pGL3B-OB4. In other further preferred embodiments, a positive transcription element or negative transcription element is selected. For example, the negative transcription elements from nucleotide −978 to −217 or from nucleotide −1869 to −217 of the human ob gene may be used. Exemplary recombinant nucleic acids are pGL3-OBΔ12 and pGL3-OBΔ5.

By "isolated" in reference to nucleic acid is meant a polymer of 2 (preferably 21, more preferably 39, most preferably 75) or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular context. Thus, the sequence may be in a cell-free solution or placed in a different cellular environment or nucleic acid context. The term does not imply that the sequence is the only nucleotide chain present, but does indicate that it is the predominate sequence present (at least 10–20% more than any other nucleotide sequence) and is essentially free (about 90–95% pure at least) of non-nucleotide material naturally associated with it. The term does not encompass an isolated chromosome containing an ob gene control region.

By "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased in a useful manner and preferably separate from a library of undefined clones. The term "significantly" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The DNA from other sources may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

By "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the cDNA derived from the native message.

By "recombinant" in reference to nucleic acid is meant the nucleic acid is produced by recombinant DNA techniques such that it is distinct from a naturally occurring nucleic acid.

By "enhancer" is meant a DNA regulatory region that enhances transcription. An enhancer is usually, but not always, located outside the proximal promoter region and may be located several kilobases or more from the transcription start site, even 3' to the coding sequence or within the introns of the gene. Promoters and enhancers may alone or in combination confer tissue specific expression.

By "silencer" is meant a control region of DNA which when present in the natural context of the ob gene causes a suppression of the transcription from that promoter either from its own actions as a discreet DNA segment or through the actions of trans-acting factors binding to said elements and effecting a negative control on the expression of the gene. This element may play a role in the restricted cell type expression pattern seen for the ob gene, for example expression may be permissive in adipocytes where the silencer may be inactive, but restricted in other cell types in which the silencer is active. This element may or may not work in isolation or in a heterologous promoter construct.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In another aspect, the present invention features a method for identifying agents which modulate or regulate the transcription of an ob gene. This method includes (a) providing a system having a control region of an ob gene (e.g. human ob gene) and a nucleic acid sequence (e.g., a reporter gene) (both of which are preferably inserted in a vector), wherein the control region is transcriptionally linked to the nucleic acid sequence so that it is effective to initiate, terminate or regulate the transcription of that nucleic acid sequence, (b) contacting a candidate agent with the system, and (c) assaying for a measurable difference in the level of transcription of the nucleic acid sequence as an indicant of the candidate's activity. The system may be a cell, an animal such as a mammal, or an in vitro transcription system. The preferred cells are eukaryotic cells, including yeast cells and mammalian cells. The recombinant nucleic acid described above may be included in the system to provide the control region and the reporter sequence. An agent that increases the level of transcription of the nucleic acid sequence is an up regulator. An agent that decreases the level of transcription of the nucleic acid sequence is a down regulator. Where an ob gene has a control region that is also present in a non-ob gene, the control region from equivalent sources may also be used in the screening assay. For example, if a glucocorticoid response element (GRE) is present in an ob gene control region, GREs from other sources may be used to screen for ob gene modulators too.

In a preferred embodiment, the nucleic acid is introduced into a host cell or an organism by either transfection or adenovirus infection and the system includes the cell or the organism. In an even further preferred embodiment, a transgenic animal system is used in the assay.

In another preferred embodiment, the system further includes a transcriptional protein.

By "transcriptional protein" is meant a cytoplasmic or nuclear protein that, when activated, binds a promoter, enhancer or silencer either directly, or indirectly through a complex of proteins to modulate the transcription activity of the promoter. The transcriptional protein may either be endogenous to the cell or expressed from a recombinant nucleic acid transfected into the cell. Examples of transcriptional proteins include, but are not limited to, C/EBPα protein and other proteins that bind to a C/EBP site or Sp1 site, and intracellular receptors.

By "intracellular receptor" is meant an intracellular transcription factor whose activity is regulated by binding of small molecules, including, but not limited to, estrogen receptor (ER), retinoid acid receptors (RAR), retinoid X receptors (RXR), glucocorticoid receptors (GR), progesterone receptors (PR), androgen receptors (AR), thyroid hormone receptors (TR), peroxisome proliferator activated-receptors (PPARs, such as PPARγ) and vitamin D receptors. The intracellular receptor may either be endogenous to the cell or expressed from a recombinant nucleic acid transfected into the cell. Preferred intracellular receptors to be present in the assay include PPARγ, RXR and PPARα.

The basal level of the mammalian ob gene expression may be raised up before adding a candidate down regulator to the screening assay.

In a preferred embodiment, the assay is conducted in a mammalian adipocyte cell such as a primary adipocyte cell or a immortalized adipocyte cell. A rat, mouse or a human primary adipocyte cell is used. Mammalian preadipocytes may be used for the assay as well. Exemplary cells include 3T3-F422A, ob 1771, 3T3-L1 and rat primary adipocyte. Any other cells in which the control region is capable of initiating, terminating or regulating the transcription of the reporter sequence may be used.

In another preferred embodiment, the sequence of the control region is used as a guide in selecting potential modulators for screening. For example, if glucocorticoid response elements (GRE), peroxisome proliferator response elements (PPRE), thyroid hormone response elements (TRE), retinoic acid response elements (RARE), retinoid X response elements (RXRE), estrogen response elements (ERE), progesterone response elements (PRE), androgen response elements (ARE), insulin receptor response elements, other transcription regulatory binding sites such as the helix-loop-helix family members including sterol regulatory element binding protein family (SREBP) or its adipocyte expressed homologue ADD-1, CAAT/enhancer binding protein (C/EBP), AP-1, AP-2, SP-1, NFκB, Oct-1, serum response elements, cAMP response elements, or growth hormone (GH) response elements are present in this region, compounds known to act through these elements will be selected for screening. Compounds acting on the above mentioned elements can be screened in the assays for ob gene modulators.

In a preferred embodiment, the candidate agent is selected from, but not limited to, the group consisting of estrogen receptor, retinoid acid receptors, retinoid X receptors, glucocorticoid receptors, progesterone receptors, androgen receptors, thyroid hormone receptors, and vitamin D receptors.

In another preferred embodiment, the candidate agent is selected from the group consisting of glucocorticoids; thyroid hormones; thyromimetics; fibrates, free fatty acids and other agonists of PPAR including Di-(2-ethylhexyl)-phthalate, plasticizers and herbicides including 2, 4, 5-trichlorophenoxyacetic acid and leukotriene antagonists; antagonists of PPAR and PPAR subtype selective compounds; RAR selective agonists and antagonists including subtype selective compounds; RXR selective agonists and antagonists including subtype selective compounds; estrogens and other agonists and antagonists of ER; androgens and other agonists and antagonists of AR; progestins and other agonists and antagonists of PR; non-steroid progestins; mineralocorticoids and other agonists and antagonists of MR; insulin; glucose; glucagon; free fatty acids; amino acids; sugars and other secretagogues including biguanides; antidiabetics including metformin and phenformin; pyroglyrides; linoglyrides and benzothenediones; non-steroidal anti-inflammatory drugs; prostacyclins; prostaglandins; dihydroepiandosterone and stimulators, precursors and derivatives thereof including Dioscorea and aloe vera, and extracts and compounds derived therefrom; tumor necrosis factors; cytokines and related signaling molecules; growth factors; fetuin; Amylin agonists and antagonists; prolactin; niacin; Acepimox and other nicotinic acid derivatives; triacsins; amphetamines and derivatives including fenfluramine and dexfenfluramine; endorphin antagonists; somatostatin; cholecystokinin; bombesin; gastrin; oral anti-diabetic agents; corticotropin releasing hormone; thiazolidinedione compounds; adrenocorticotropic hormones; melanocyte stimulating hormone; gastric inhibitory peptide; growth hormone agonists and antagonists; β-adrenergic agonists and antagonists including is phenoxybenzamide; fluloxetine; neuropeptide Y and modulators of its activity or expression; and the gene products of agouti and GLP-1.

Candidate compounds of ob gene modulators include but are not limited to those disclosed and referred to in Table 1.

Peptide or small molecule combinatorial libraries can be used to screen for modulators of ob gene expression (Bunin, B. A. N. Ellman, J. A., *J. Am. Chem. Soc.* 114:10997–10998 (1992) and references contained therein).

Preferred candidate up regulators of an ob gene include PPARδ antagonist, C/EBP protein agonist, PPARα agonist, glucocorticoid, insulin derivative, insulin secretagogue, insulin sensitizer, and insulin mimetic.

Preferred candidate down regulators of an ob gene include PPARγ agonist, C/EBP protein antagonist, PPARα antagonist, glucocorticoid antagonist, and insulin antagonist. A preferred PPARγ agonist is a thiazolidinedione compound, including, but not limited to, troglitazone (CS-045), pioglitazone (AD-4833), ciglitazone (ADD-3878) and analogs (e.g. WAY-120, 744), BRL 49653 and analogs, englitazone, AD 5075 and darglitazone (CP-86325).

To screen for an agent which modulates the interaction of a ligand with an intracellular receptor, a ligand for the intracellular receptor is included in the assay.

The binding of a transcriptional protein to the ob gene promoter and regulatory elements may be measured by techniques known to those skilled in the art, including, but not limited to, mobility shift assay, co-transfection assay, and expression of a reporter gene linked to the promoter.

Applicant discovered that thiazolidinedione compounds reduce the expression of ob gene through PPARγS. Thiazolidinedione compounds are also useful in partially restoring euglycemia in NIDDM patients. They act at both transcriptional and non-transcriptional levels that may mimic or oppose the actions of insulin.

On the one hand, it is known that these compounds act immediately to facilitate the translocation of glucose transporter GLUT4 to the cell membrane where it rapidly increases glucose uptake in treated cells, an effect which cannot be accounted for by transcriptional mechanisms.

On the other hand, these compounds, esp. ERL 49653, have been shown to be ligands for the PPARγ subtype and can act as transcriptional modulators to directly affect the transcription of target genes, e.g. modulating the effects of PPARγ on the expression of certain genes. For example, BRL 49653 amplifies the suppression of ob gene expression by PPARγ in primary adipocytes, an effect opposite to that of insulin.

Therefore, thiazolidinedione compounds can exert different effects on a gene or metabolic pathway depending on the combinatorial makeup of the promoter of the gene and whether the effect is transcriptional or non-transcriptional. The screening assay described herein allows one to identify the effect of thiazolidinedione compounds on ob gene expression.

While steroids and steroid analogues may exemplify agents identified by the present invention, Applicant is particularly interested in the identification of agents of low molecular weight (less than 10,000 Daltons, preferably less than 5,000, and most preferably less than 1,000) which can be readily formulated as useful therapeutic agents.

Such agents can then be screened to ensure that they are specific to tissues with pathological conditions related to ob gene expression with little or no effect on healthy tissues such that the agents can be used in a therapeutic or prophylactic manner. If such agents have some effect on healthy tissues they may still be useful in therapeutic treatment, particularly in those diseases which are life threatening.

Once isolated, a candidate agent can be put in pharmaceutically acceptable formulations, such as those described in *Remington's Pharmaceutical Sciences*, 18th ed., Mack Publishing Co., Easton, Pa. (1990), incorporated by reference herein, and used for specific treatment of diseases and pathological conditions with little or no effect on healthy tissues.

In another aspect, this invention features a pharmaceutical composition capable of modulating the transcription activity of a mammalian (e.g., human) ob gene control region, i.e. containing a pharmaceutically effective amount of a modulator (e.g. up regulator or down regulator) of the mammalian ob gene control region.

In a preferred embodiment, the composition is held within a container which includes a label stating to the effect that the composition is approved by the FDA in the United States (or other equivalent labels in other countries) for treating a disease or condition selected from the group consisting of obesity, diabetes, infertility, cardiovascular diseases, hypertension, hyperlipidemia, hypercholesterolemia, cachexia and anorexia; or even approval to use the agent by normal humans who wish to change their body weight or other physical conditions by modulating the expression level of the ob gene. Such a container will provide therapeutically effective amount of the active ingredient to be administered to a host.

In further preferred embodiments, the composition includes a glucocorticoid, such as, but not limited to, hydrocortisone, triamcinolone or dexamethasome hydrocortisone; insulin, insulin derivative, insulin secretagogue, insulin sensitizer, or insulin mimetic; PPARγ agonist or antagonist including fish oils, free fatty acids, or thiazolidinedione compounds such as BRL49653 or pioglitazone. Other thiazolidinedione compounds include, but are not limited to, troglitazone (CS-045), ciglitazone (ADD-3878) and analogs (e.g. WAY-120, 744), englitazone, AD 5075 and darglitazone (CP-86325).

In another aspect, this invention features a method for modulating the expression level of a mammalian ob gene by administering to a mammalian cell or a mammal a composition including an effective amount of a modulator (e.g. up regulator or down regulator) of the control region. Other systems (e.g. in vivo or in vitro, yeast or Drosophila) containing a control region of an ob gene may be modulated similarly.

In a preferred embodiment, the method further includes step of measuring the transcriptional activity of the control region.

In further preferred embodiments, the composition includes an up regulator, e.g. a glucocorticoid, such as, but not limited to, hydrocortisone, triamcinolone or dexamethasome hydrocortisone; insulin, insulin derivative, insulin secretagogue, insulin sensitizer, or insulin mimetic; PPARγ antagonist; C/EBP protein agonist; and PPARα agonist.

In another further preferred embodiments, the composition includes a down regulator, e.g. a C/EBP protein antagonist, PPARα antagonist, glucocorticoid antagonist, insulin antagonist, fish oil, free fatty acid, or PPARγ agonist including thiazolidinedione compounds such as BRL49653 or pioglitazone. Other thiazolidinedione compounds include, but are not limited to, troglitazone (CS-045), ciglitazone (ADD-3878) and analogs (e.g. WAY-120, 744), englitazone, AD 5075 and darglitazone (CP-86325).

An effective amount of an agonist or antagonist of PPARα or PPARβ may also be included in the composition.

In another aspect, this invention features a method for treating a patient with anorexia by administering sufficient amount of a down regulator of human ob gene expression.

In another aspect, this invention features a method for the treatment of cachexia, anorexia or any wasting disease characterized by insufficient food intake or body weight loss, whereby a host (e.g. a mammalian animal or human) is administered with a composition containing a pharmaceutically effective amount of a down regulator of ob gene expression.

In preferred embodiments, the down regulator is a free fatty acid, fish oil, or PPARγ agonist which includes a thiazolidinedione compound such as BRL49653 or pioglitazone. Other thiazolidinedione compounds include, but are not limited to, troglitazone (CS-045), ciglitazone (ADD-3878) and analogs (e.g. WAY-120, 744), englitazone, AD 5075 and darglitazone (CP-86325). The down regulator may also be a C/EBP protein antagonist, PPARα antagonist, glucocorticoid antagonist, or insulin antagonist.

In another aspect, this invention features a method for changing the body weight or body fat content of a host by administrating to a composition containing a pharmaceutically effective amount of an up regulator or down regulator of ob gene expression. The up regulator may be selected from the group consisting of glucocorticoid, hydrocortisone, triamcinolone and dexamethasome hydrocortisone, insulin, insulin derivative, insulin secretagogue, insulin sensitizer, insulin mimetic, PPARγ antagonist, PPARα agonist, and C/EBP protein agonist. The down regulator may be selected from the group consisting of PPARγ agonist, thiazolidinedione, BRL49653 and analogs, pioglitazone, troglitazone (CS-045), ciglitazone (ADD-3878) and analogs (e.g. WAY-120, 744), englitazone, AD 5075, darglitazone (CP-86325), free fatty acid, fish oil, C/EBP protein antagonist, PPARα antagonist, glucocorticoid antagonist, and insulin antagonist.

In another aspect, this invention features a method for treating an overweight patient having a body weight more than about 10% to or about 20% in excess of the ideal body weight by administering a composition containing a pharmaceutically effective amount of an up regulator of ob gene expression.

In another aspect, this invention features a method for helping a person having a functional ob gene to control his or her body weight by administering a composition containing a pharmaceutically effective amount of a modulator of human ob gene expression.

By "a functional ob gene" is meant an ob gene encoding an ob protein having substantially the same biochemical activity of the wild type ob proteins disclosed in Zhang et al., Nature 372:425–432, 1994, including, but not limited to, the wild type ob genes disclosed in Zhang et al., id. A functional ob gene may have some differences from the wild type ob genes disclosed in Zhang et al., id., yet these differences do not significantly change the biochemical activity of the ob protein expressed therefrom. Also included is the case where one allele of ob is mutated, leaving only one functional copy of the ob gene whose expression is subject to modulation.

In yet another aspect, this invention features a composition and method to use this composition to change the body weight or body fat content of an animal, including, but not limited to, a mammalian animal for veterinary or agricultural purposes; this composition comprises an effective amount of a modulator of ob gene expression.

The present invention also relates to the isolation and identification of the promoter and other regulatory elements of other genes in the fatty acid metabolic pathways using methods described herein for the ob gene. These genes include, but are not limited to, fat, tub, db (diabetics), agouti, glucagon-like protein-1, neuropeptide-Y and fatp (fatty acid transfer protein). The discoveries of control regions for these genes allow for the screening of agents that specifically influence these genes, expression and thence for construction or design of other modulators of such genes' expression. Such discovery will also allow identifying therapeutic agents and using these agents to treat diseases and conditions affected by these genes and/or these genes, product, such as, but not limited to, obesity, cardiovascular diseases, diabetes and anorexia.

Other features and advantages of the invention will be apparent from the following detailed description of the invention, and from the claims.

Panel A: Body weights were recorded at the beginning and end of the experiment and are expressed as percentage of pre-treatment (day 0) body weight.

Panel B: At the end of the experiment adipose tissue was isolated, RNA extracted and ob and β-actin mRNA levels measured as described in materials and methods. Values are expressed in relative absorbance units (R.A.U.) taking the controls as 100%.

Figure 5A:
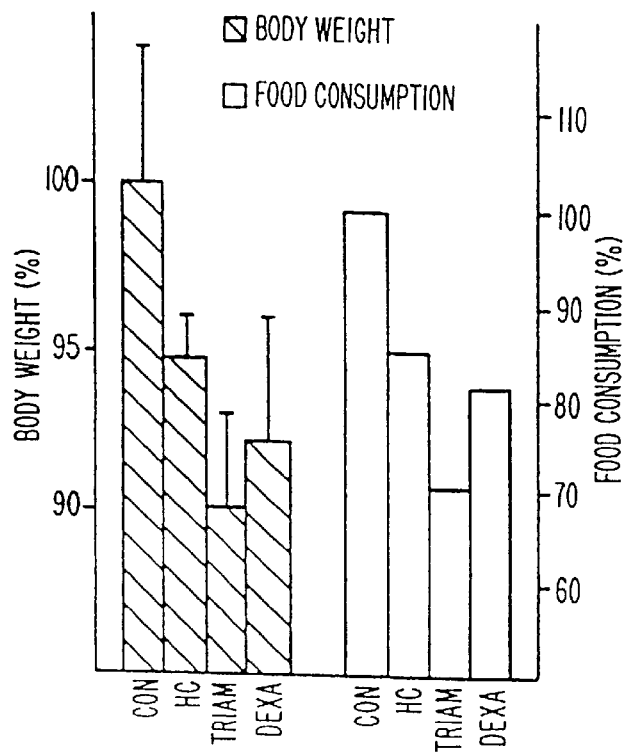
Figure 5B:
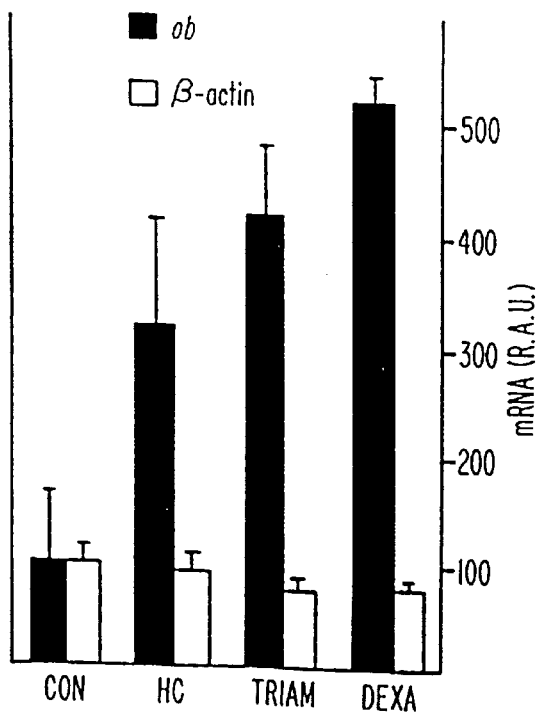

FIGS. 5A–B is a graph which shows body weight, food consumption (A) and adipose tissue's ob mRNA levels (B).

Panels A&B: Adult male rats (n=3 animals/group) were treated for 4 days with vehicle (CON), hydrocortisone (HC; 100 μg/g body weight/day), triamcinolone (TRIAM; 20 μg/g body weight/day) or dexamethasone (DEXA; 3.7 μg/g body weight/day). Body weight and food consumption were recorded at the end of the experiment and are expressed as percentage of the controls (Panel A). Adipose tissue was isolated, RNA extracted and ob and β-actin mRNA levels were measured as described below (Panels B). Values are expressed in relative absorbance units (R.A.U.) taking the controls as 100%.

Adult male rats (n=3 animals/group) were sacrificed 24 hr after a single injection of dexamethasone (DEXA; 3.7 μg/g body weight/day) or vehicle (CON). 10 mg of total RNA extracted from individual animals was pooled and subjected to electrophoresis, transferred to a nylon membrane and hybridized consecutively to labeled ob (top panel) or β-actin (bottom panel) cDNA as described below. The position of the 18S and 28S rRNA bands are indicated on the right of the top panel.

Figure 6:
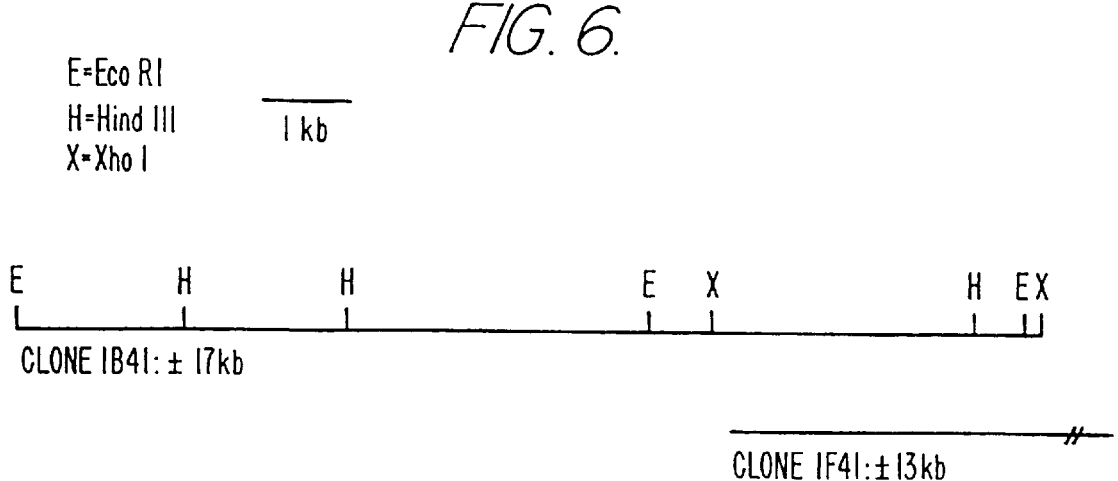

FIG. 6 is a restriction map of clones 1B41 and 1F41. Coding sequence has been localized to the unique 5' XhoI-HindIII 3' fragment indicating that clone 1B41 has more than 5 Kb of 5' flanking sequences.

Figure 7:
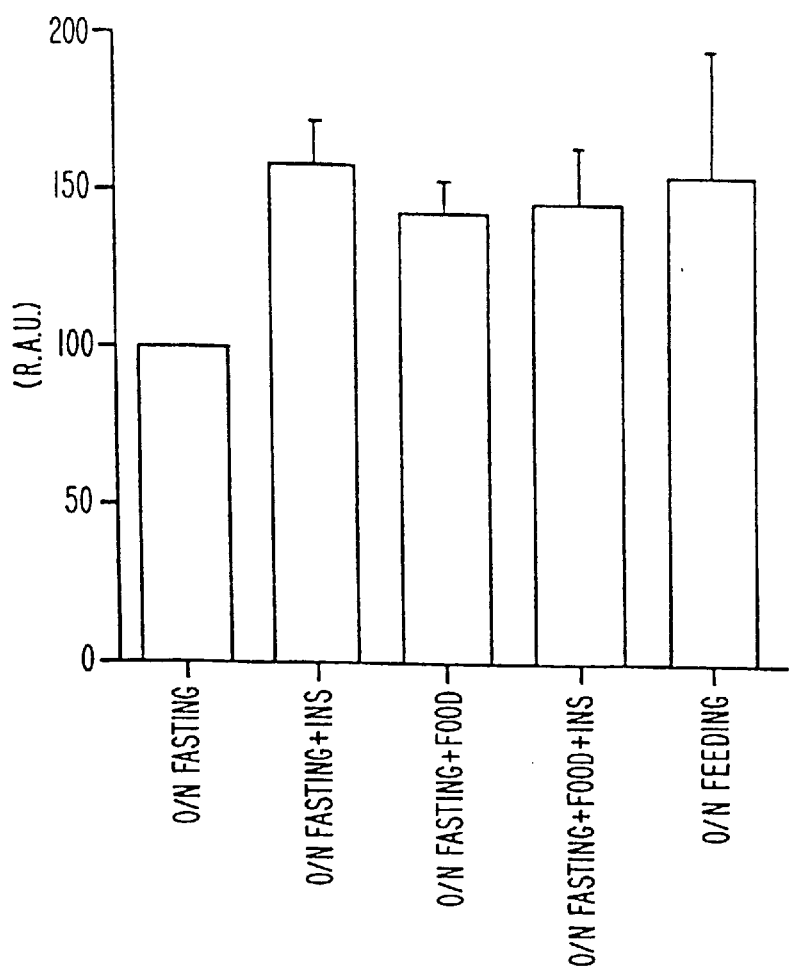

FIG. 7 is a graph which shows the level of ob gene transcription after food consumption or insulin injection.

Figure 8:
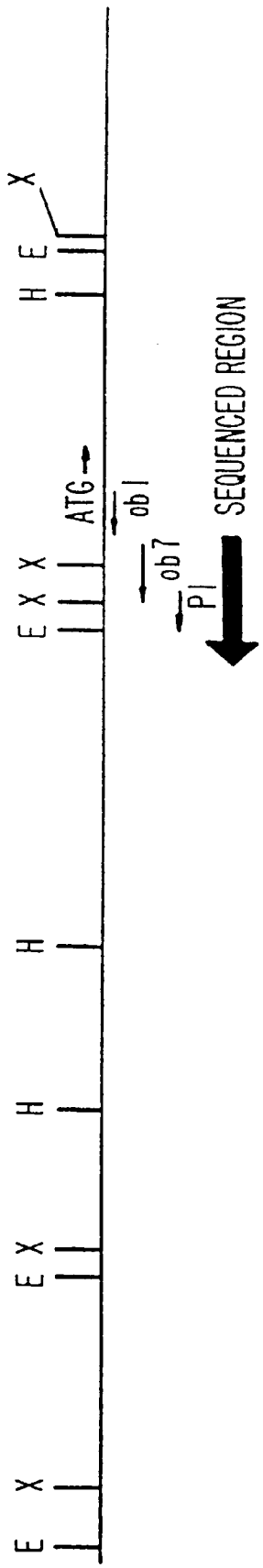

FIG. 8 is a restriction map of clone 1B41 showing schematically the approximate positions of ATG start codon for human ob gene, primers ob1, ob7 and P1, and the sequenced region represented by Seq. ID No. 3.

FIGS. 9A–I is a map showing the 5' upstream of the human ob gene. (A) is a restriction map wherein B=BamHI, E=EcoRI, H=HindIII and X=XhoI. (B) shows the location of a control region. (C) identifies regions that have been sequenced. (C) shows the location of the 1B41 clone. (E) shows the location of the EcoRI subclone of the 1B41 clone. (F) shows the location of the HindIII subclone of the P1 clones. (G) shows the location of the EcoRI subclone of the P1 clones. (H) shows the location of the BamHI subclone of the P1 clones. (I) is a scale showing the size of this map.

FIG. 10(A) is a genomic map of the human ob gene. The gene is shown in 5' to 3' orientation at the top of the diagram and is drawn to scale. Exons are denoted by black rectangles and introns by a solid line. Restriction sites for Bam HI, EcoRI, and HindIII are indicated by their first letter. Transcription initiation sites are indicated by the arrow, whereas the location of the ATG start-codon and TGA stop-codon are indicated. The regions encompassed in the λ phage and 5135 Pi clones are indicated at the bottom.

FIG. 10(B) is a map showing the structure of the human ob cDNA clone phob6.1. The different exons are highlighted. The approximate location of the various oligonucleotides used in the project are indicated at the bottom.

Figure 11:
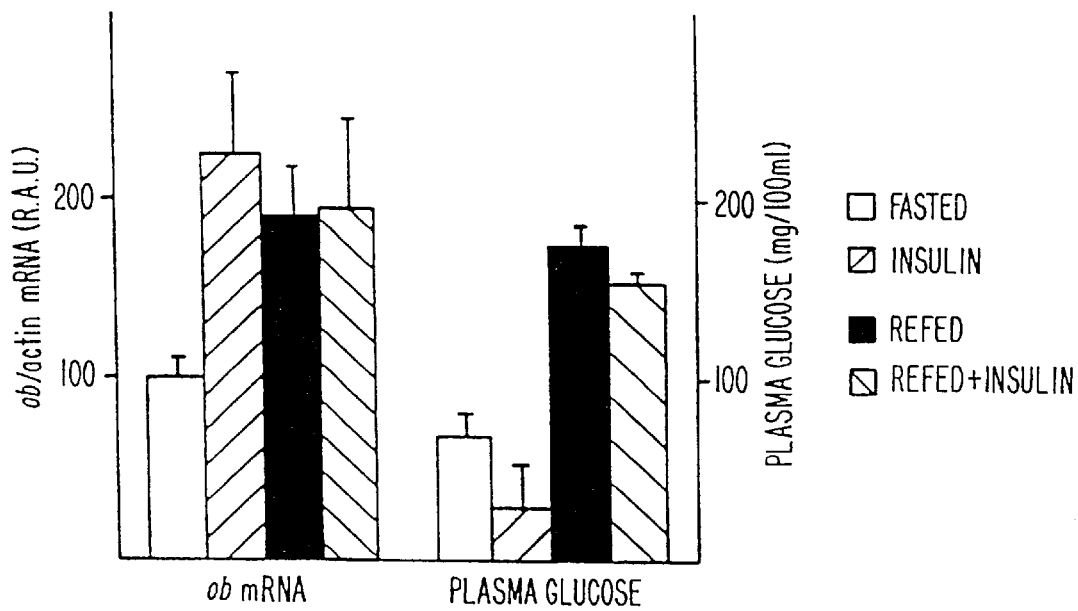

FIG. 11 is a graph which shows the levels of ob mRNA and plasma glucose after insulin injection and food consumption.

Figure 12:
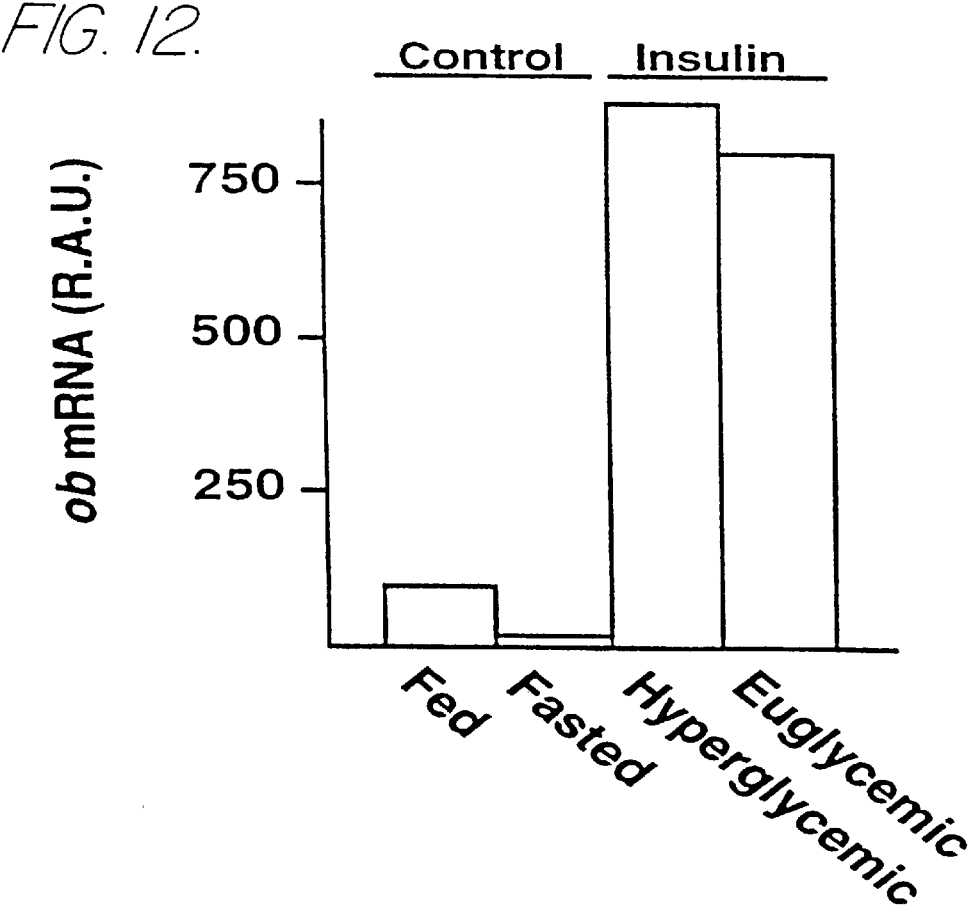

FIG. 12 is a graph which shows the levels of ob mRNA after insulin injection when plasma glucose levels were maintained at either high or low levels.

Figure 13:
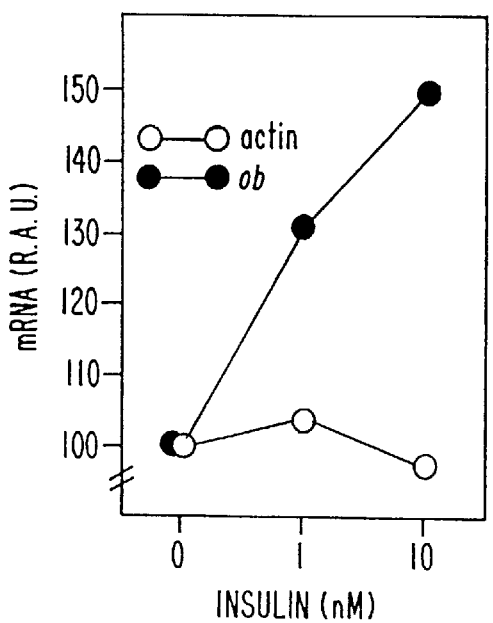

FIG. 13 is a graph which shows the levels of ob mRNA and actin mRNA in rat primary adipocytes after insulin treatment.

Figure 14A:
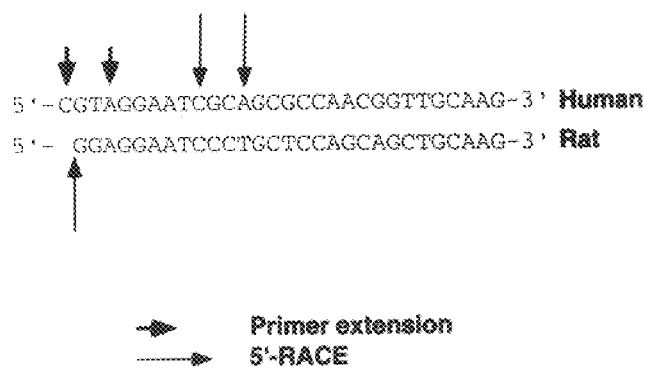
Figure 14B:
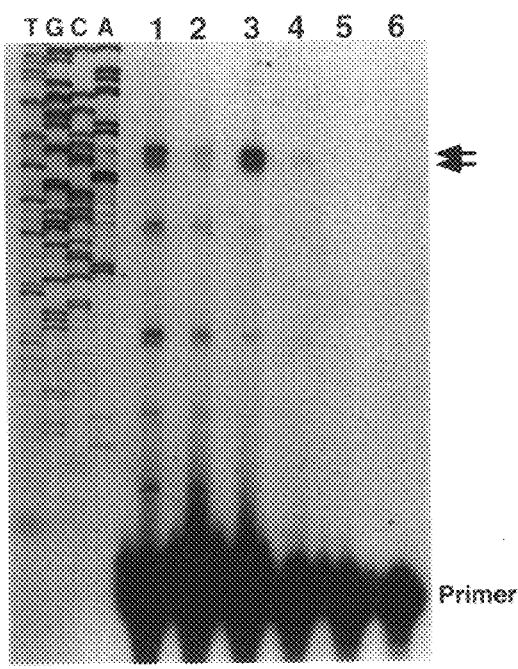

FIG. 14(A) is sequences showing ob gene transcription initiation sites in human (SEQ ID NO:47) and rat (SEQ ID NO:48) as determined by 5'-RACE and primer extension;

FIG. 14(B) is an autoradiograph showing the result of primer extension.

Figure 15:
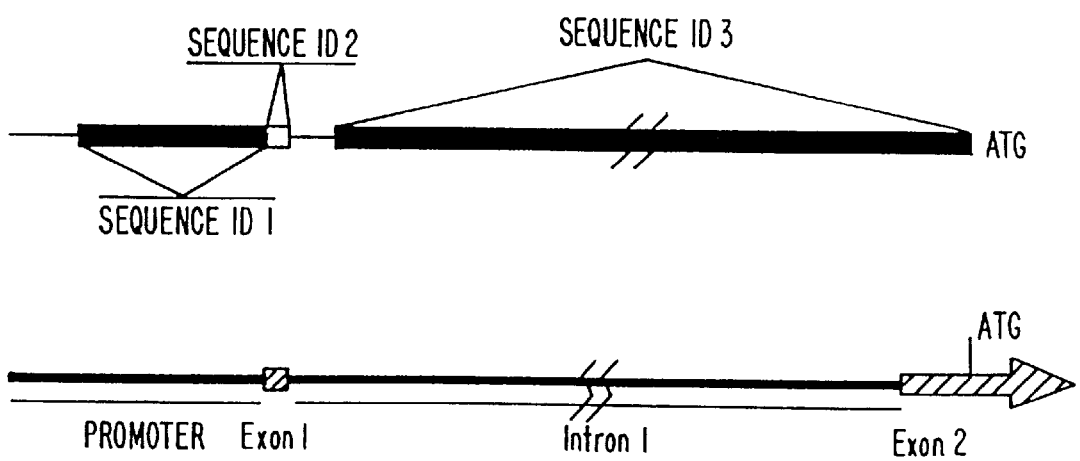

FIG. 15 is a diagram showing the locations of Sequence I.D. Nos. 1, 2 and 3; and 15(B) is a diagram showing the locations of ob gene promoter, Exon 1, Intron 1, Exon 2 and translation initiation ATG codon.

Figure 16A:
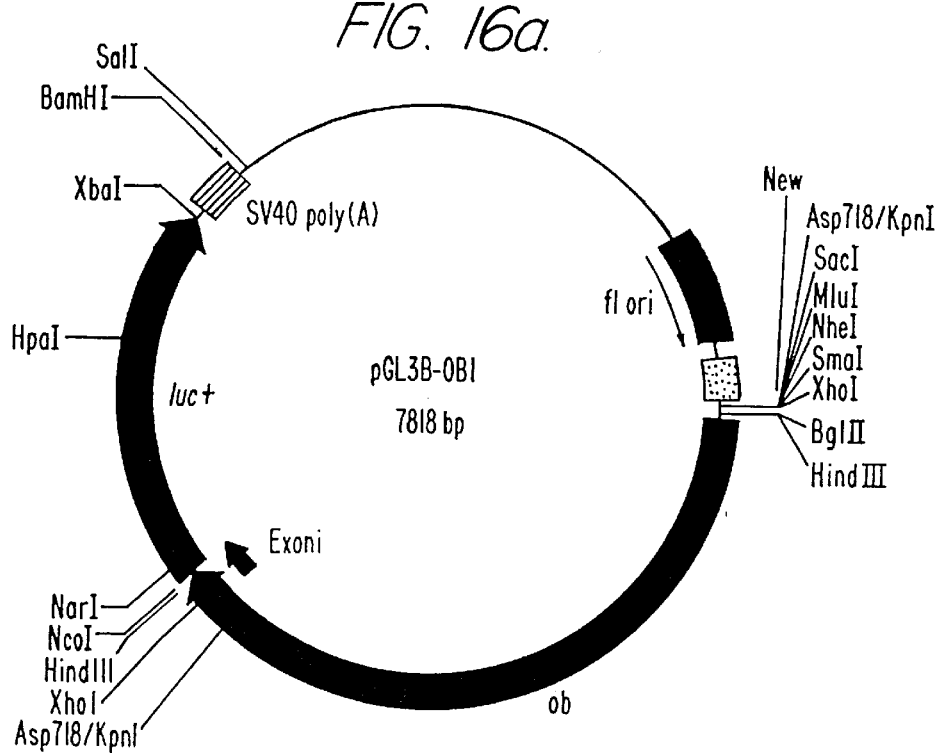
Figure 16B:
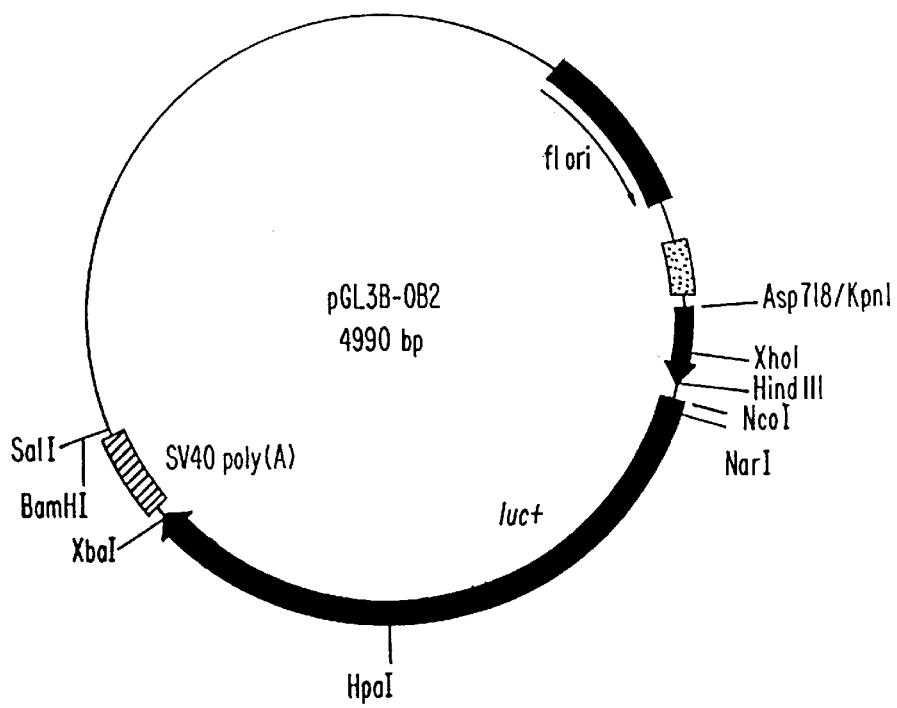
Figure 16C:
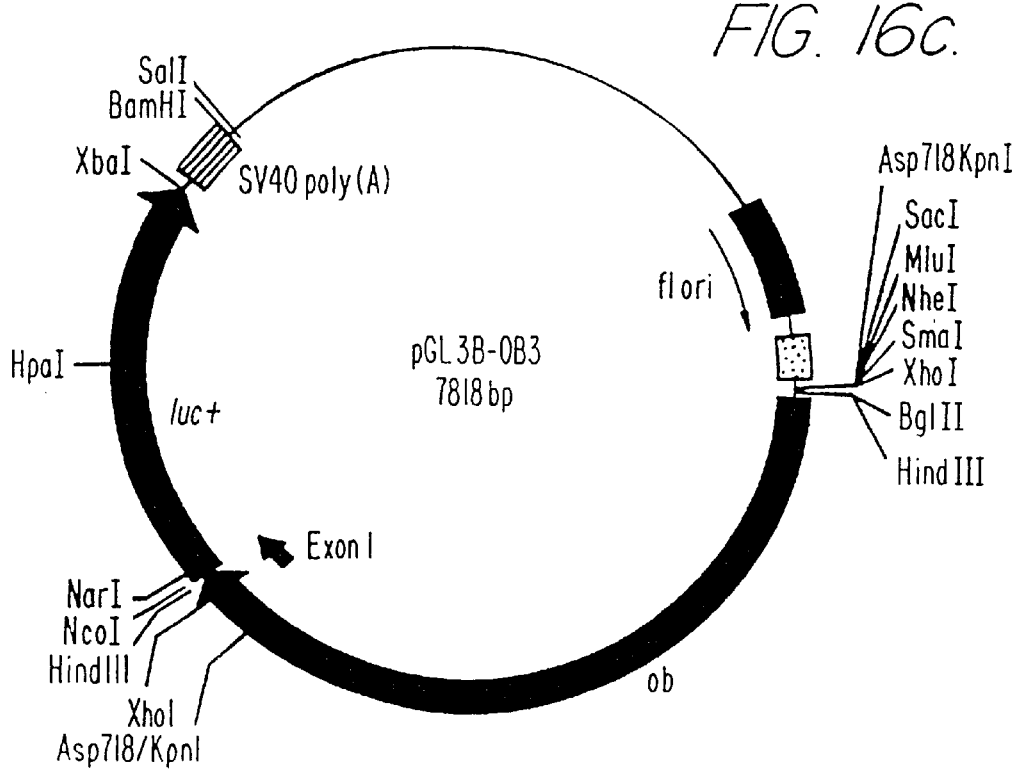
Figure 16D:
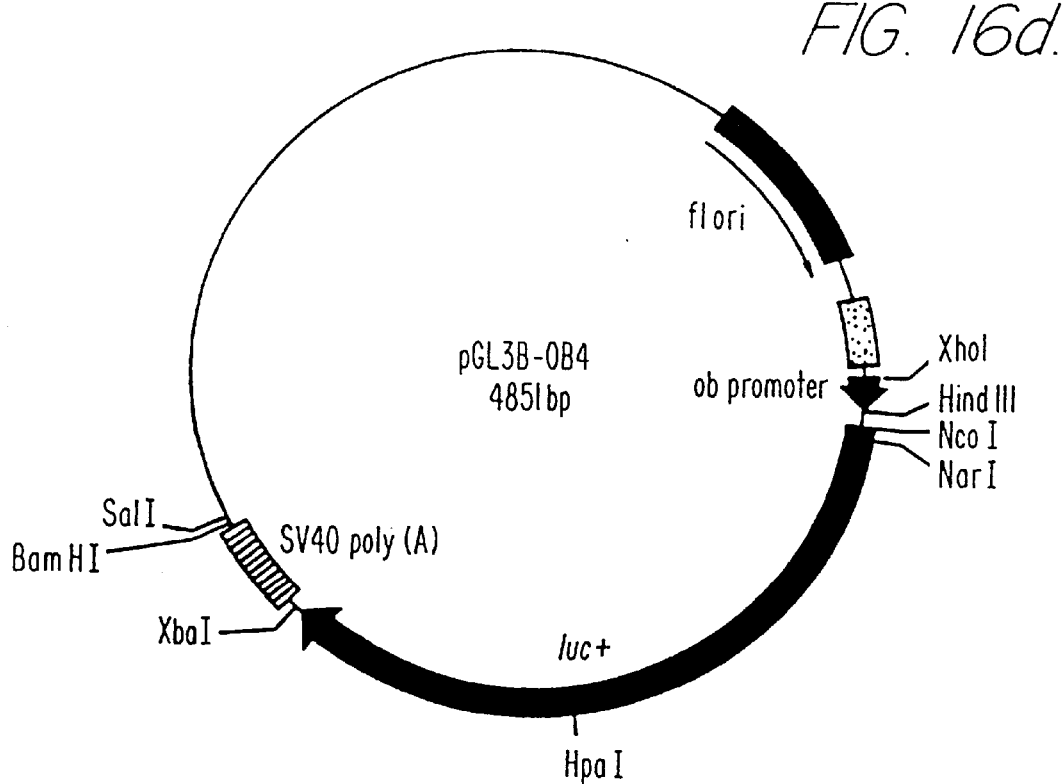

FIGS. 16(a), (b), (c) and (d) are diagrams showing schematic organization of plasmids pGL3B-OB1, pGL3B-OB2, pGL3B-OB3 and pGL3B-OB4, respectively.

Figure 17A:
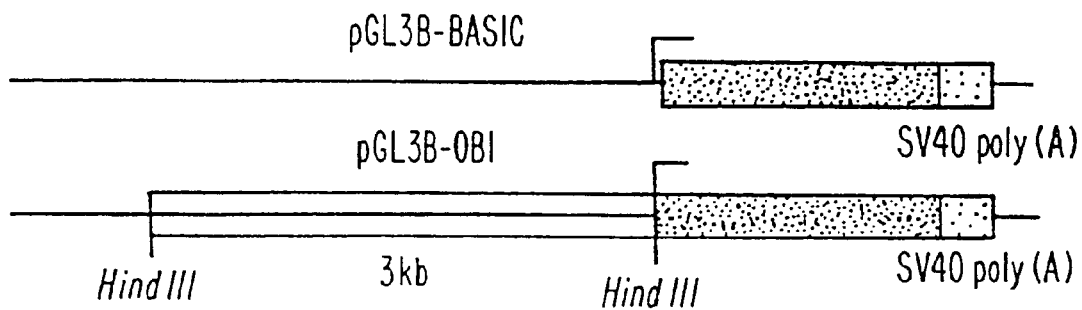
Figure 17B:
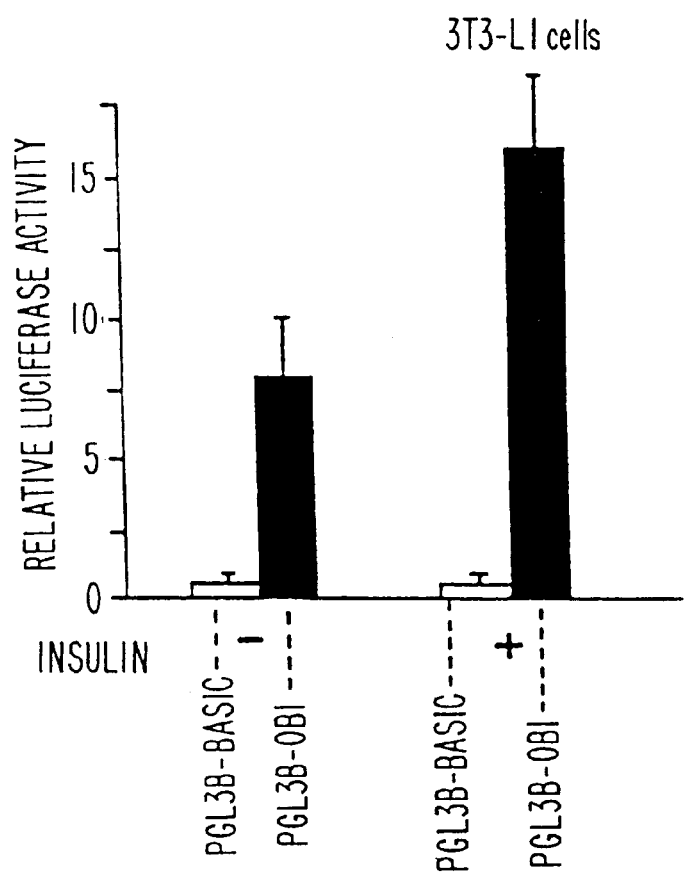

FIG. 17(A) is a diagram showing the difference in construction between pGL3B-Basic and pGL3B-OB1;

FIG. 17(B) is a graph showing luciferase activity in 3T3-L1 cells transfected with pGL3B-Basic or pGL3B-OB1 with or without insulin treatment.

Figures 1, 18C:
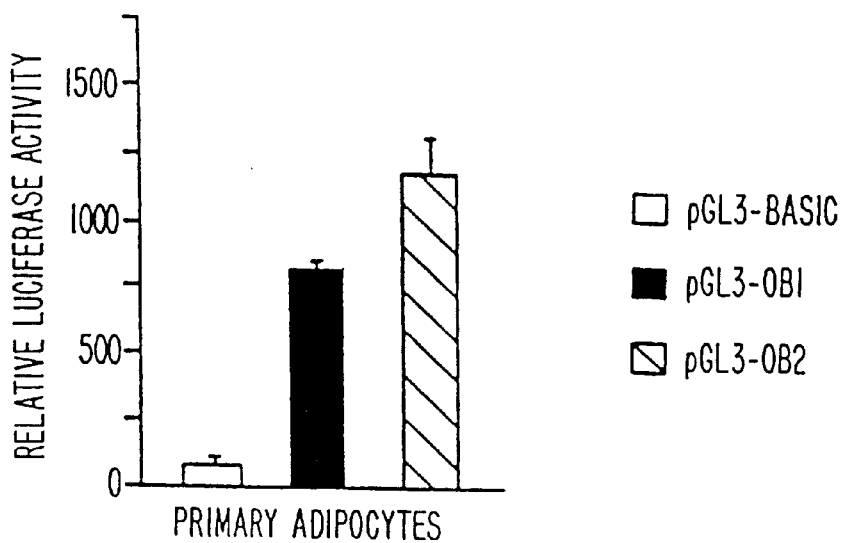
Figures 2, 18C:
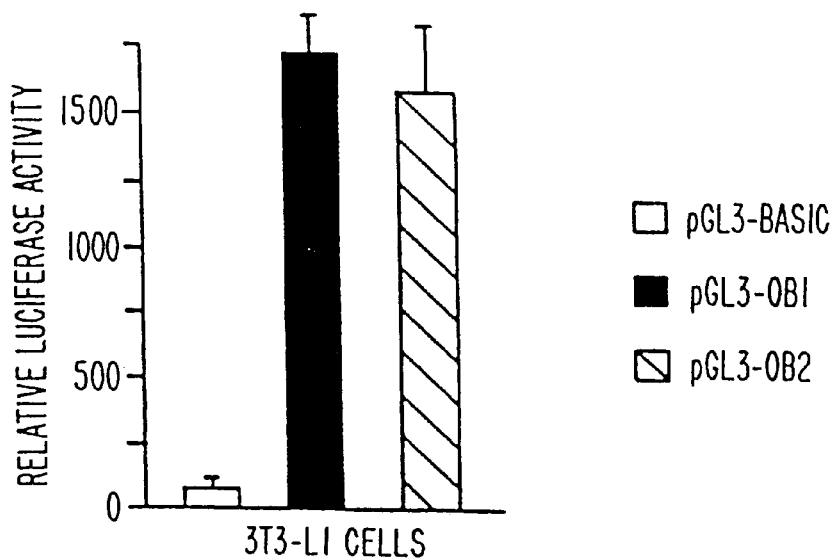

FIG. 18(A) is a diagram showing the constructs of pGL3B-Basic, pGL3B-OB1 and pGL3B-OB2;

FIG. 18(B1–4) are graphs showing normalized luciferase activity of the pGL3B-OB1 construct containing 3 kb of regulatory sequence of the human ob gene after transfection in rat primary adipocytes, 3T3-L1, CV-1 and COS cells;

FIG. 18(C1–2) is a graph showing normalized luciferase activity in rat primary adipocytes and 3T3-L1 cells transfected with pGL3B-Basic, pGL3B-OB1, or pGL3B-OB2. It shows that 217 bp of the 5' flanking region is sufficient to drive the expression of luciferase gene in transfected rat primary adipocytes and 3T3-L1 cells.

Figure 19C:
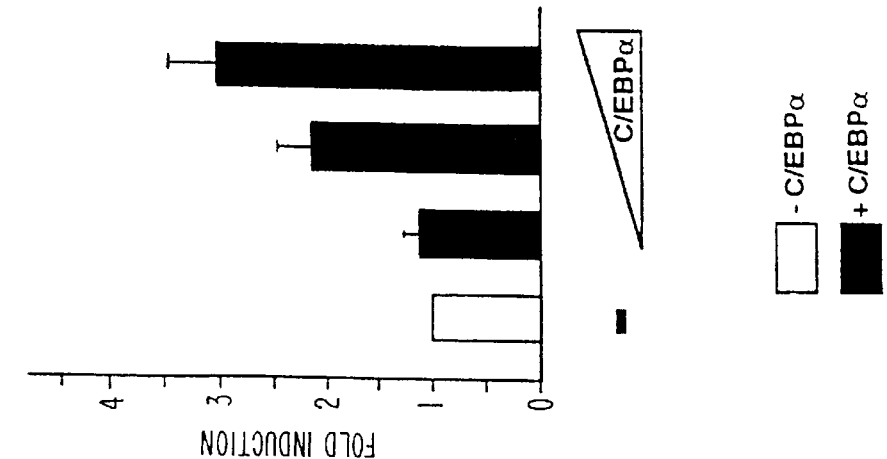
Figure 19B:
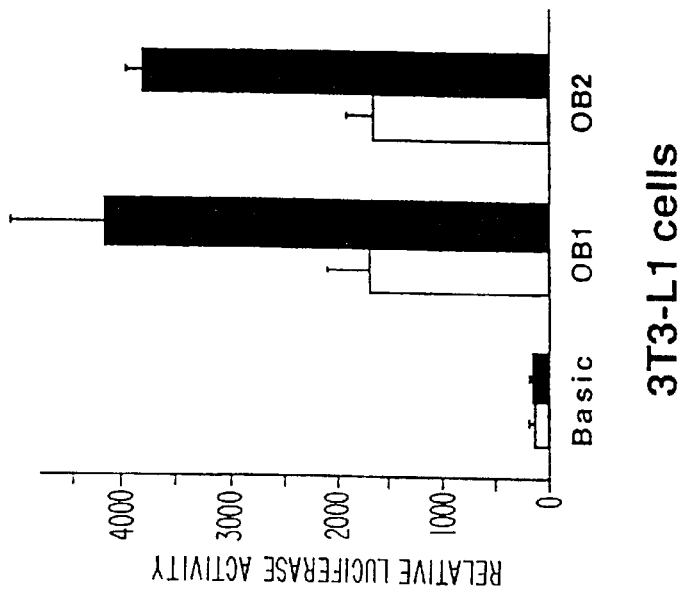
Figure 19A:
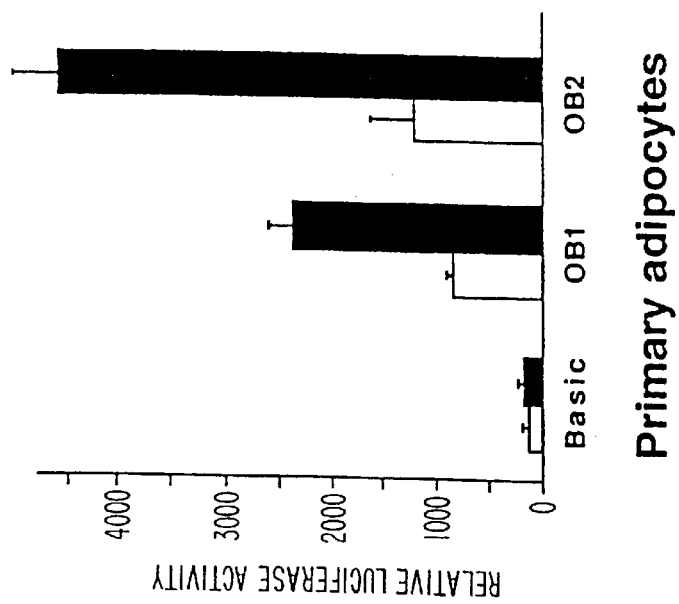

FIG. 19(A) is a graph showing normalized luciferase activity in rat primary adipocytes transfected with pGL3B-Basic, pGL3B-OB1 or pGL3B-OB2 and with or without a C/EBP-α expressing plasmid, pMSV-C/EBP (8 $\mu$g);

19(B) is a graph showing normalized luciferase activity in 3T3-L1 cells transfected with pGL3B-Basic, pGL3B-OB1 or pGL3B-OB2 and with or without a C/EBP-c expressing plasmid, pMSV-C/EBP (2$\mu$g);

19(C) is a graph showing normalized luciferase activity in rat primary adipocytes transfected with pGL3B-OB1 and increasing amount of C/EBPα expression vector. The amounts of cotransfected C/EBPα expression vector were 0, 2, 4 and 8 $\mu$g.

Figure 20A:
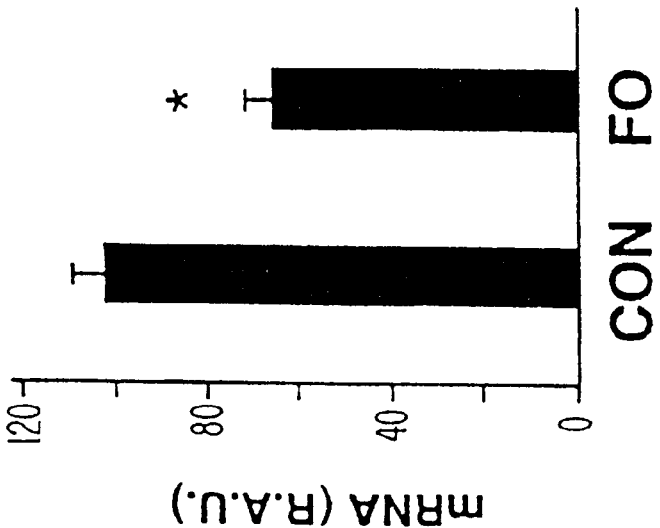

FIGS. 20(a), (b) and (C) are graphs showing adipose tissue endogenous ob mRNA levels in rats after treatment with BRL 49,653 (BRL; 10 mg/kg/day for 7 days), fenofibrate (FF; 0.5% w/w for 14 days), or a diet enriched in fish oils (FO; 20% of total caloric intake for 3 months). Results are expressed as the mean ±SD. Significant differences from control values (CON), as determined by Student's t-test ($p<0.005$), are indicated by an asterisk.

Figure 21B:
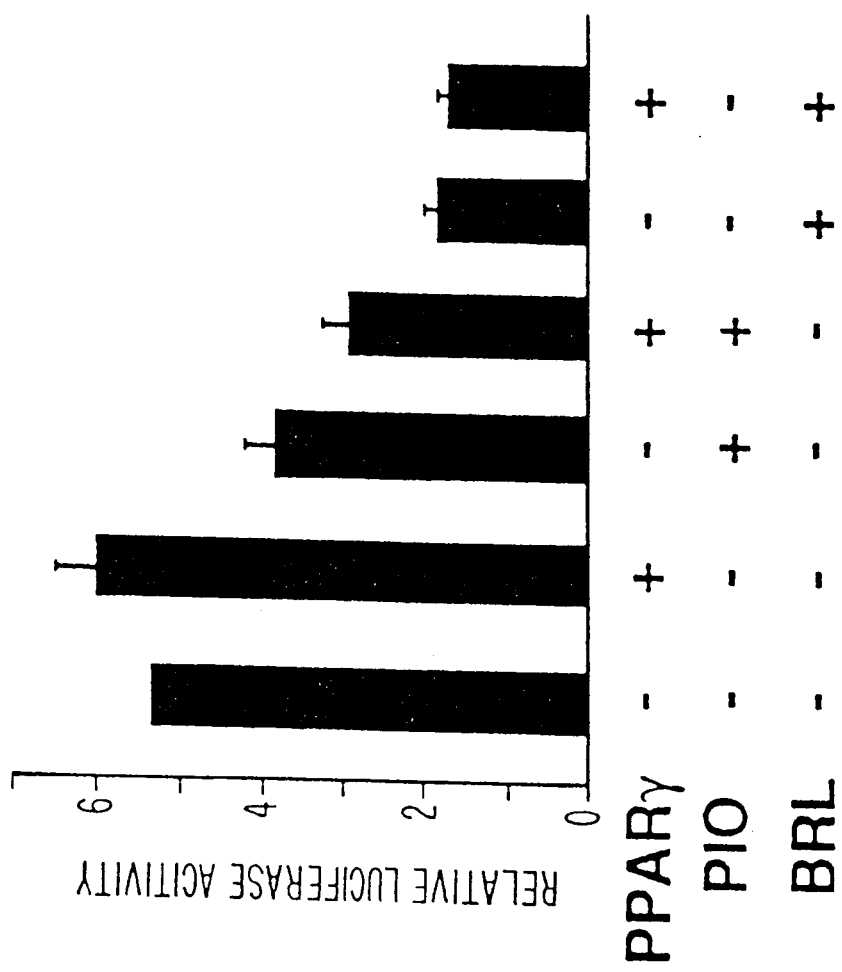
Figure 21A:
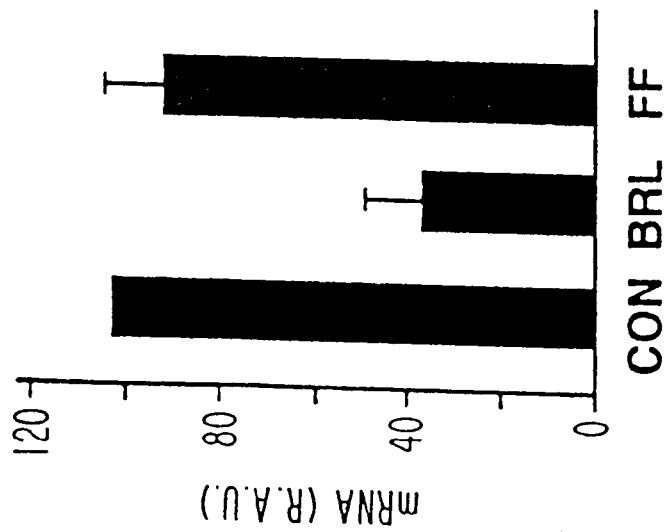

FIG. 21(A) is a graph showing endogenous ob mRNA levels in rat primary adipocytes after treatment with BRL 49,653 (100 $\mu$M, 24 hr) or fenofibric acid (250 $\mu$M, 24 hr). Results are normalized to γ-actin levels.

21(B) is a graph showing normalized luciferase activity in rat primary adipocytes transfected with pGL3B-OB1 (with 5 $\mu$g of pSG5-cgPPARγ expression vector or the empty pSG5 expression vector in the presence or absence of 10 $\mu$M BRL 49,653 or 10 $\mu$M pioglitazone (PIO)).

Figure 22:
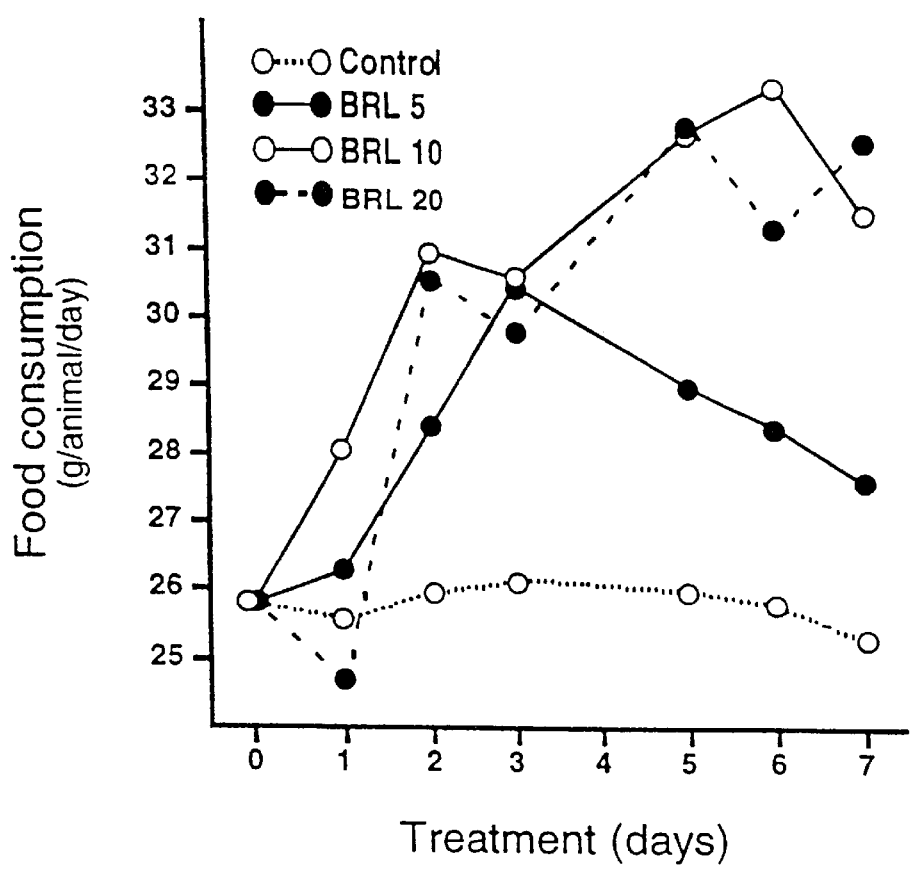

FIG. 22 is a graph showing the effect of BRL49653 on food intake in rats. Rats were administered either 0, 5, 10 or 20 mg/kg/day of BRL49653 and the effect on food intake was recorded daily.

Figure 23:
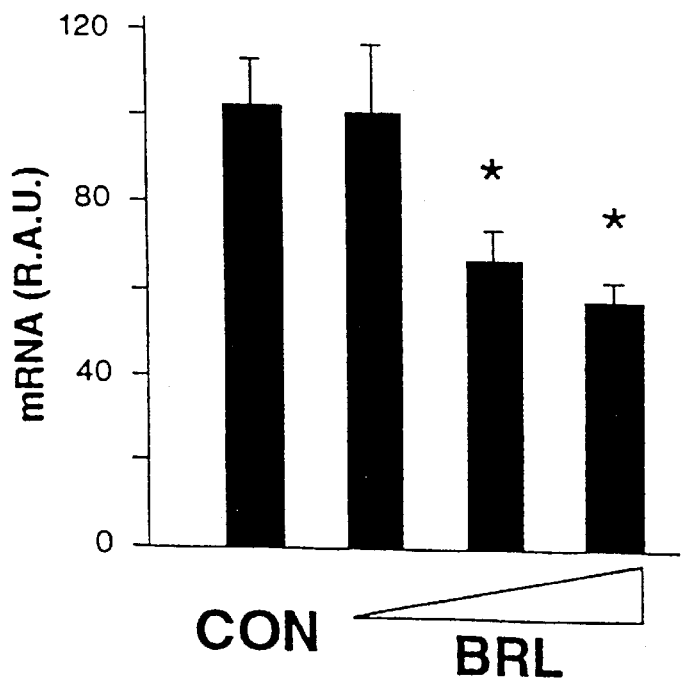

FIG. 23 is a graph showing the dose-dependent of BRL49653 on ob mRNA levels. Male rats were administered either 0, 1, 2 or 5 mg/kg/day of BRL49653 for 7 days. Adipose tissue RNA was isolated and mRNA levels quantified. The mean ±SD for 4 animals is shown.

Figure 24:
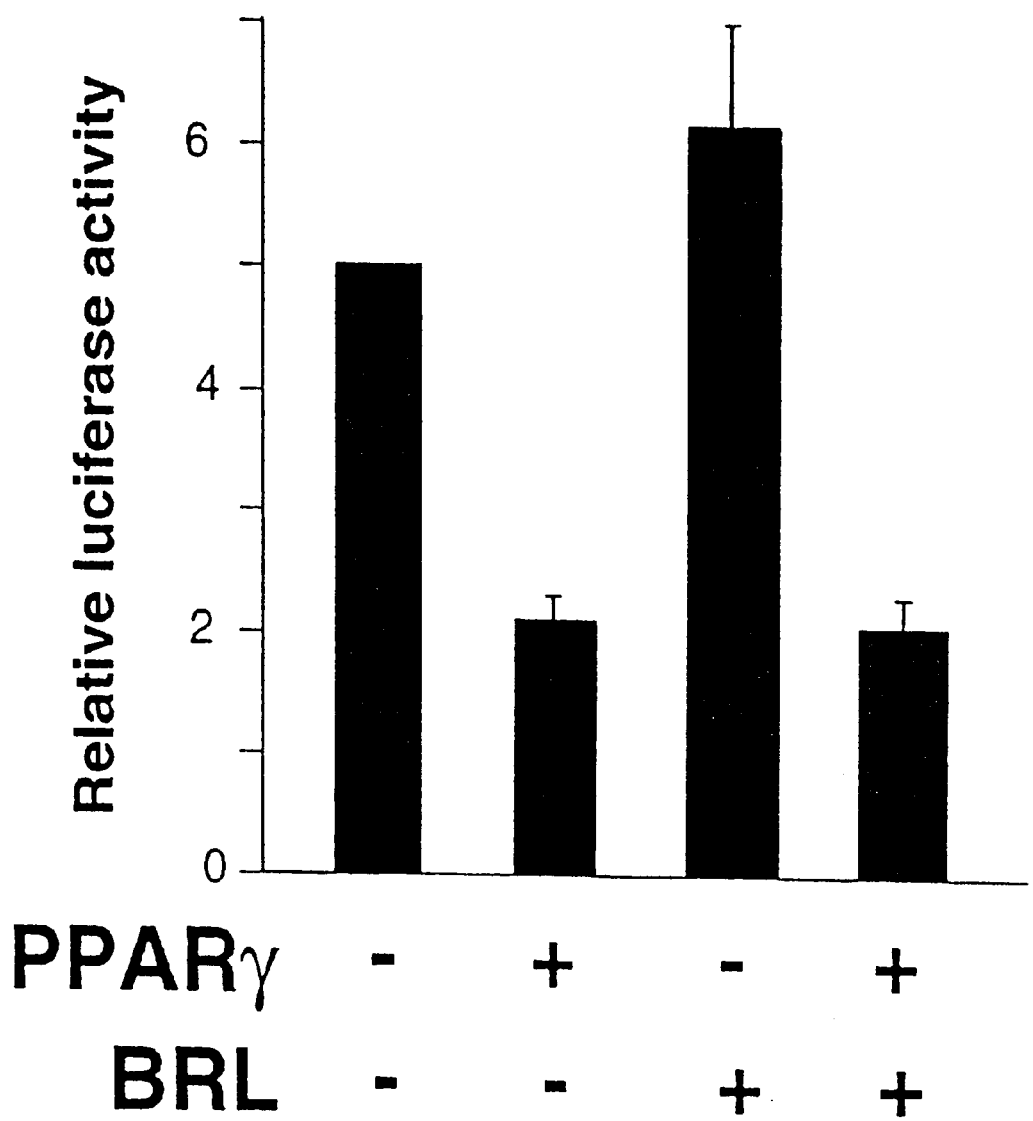

FIG. 24 is a graph showing the promoter activity of the pGL3-OB1 (2 $\mu$g) construct in 3T3-L1 preadipocytes. Luciferase activity was determined in cells cotransfected with either 2 $\mu$g of pSG5-cgPPARγ or the empty pSG5 expression vector in the presence or absence of 10 $\mu$M BRL 49,653. Cells were exposed to BRL 49,653 for 24 hours. The mean of 4 points is shown.

FIG. 25(A) is a schematic representation of the various human ob gene promoter - luciferase constructs used in the assay.

25(B) is a graph showing luciferase activity in 3T3-L1 preadipocytes driven by various nested deletions of the human ob promoter. Luciferase activity was determined in cells cotransfected with either 1 $\mu$g of the pSG5-cgPPARγ or the empty pSG5 expression vector. Results represent the mean of five points.

DETAILED DESCRIPTION OF THE INVENTION

I. Cloning the ob Gene Control Regions

The present invention embodies the realization that the precise genetic elements which are responsible for ob gene expression can be isolated away from ob gene open reading frame (i.e., amino acid coding sequences) and employed to assay for agents that modulate ob gene expression.

Figure 9:
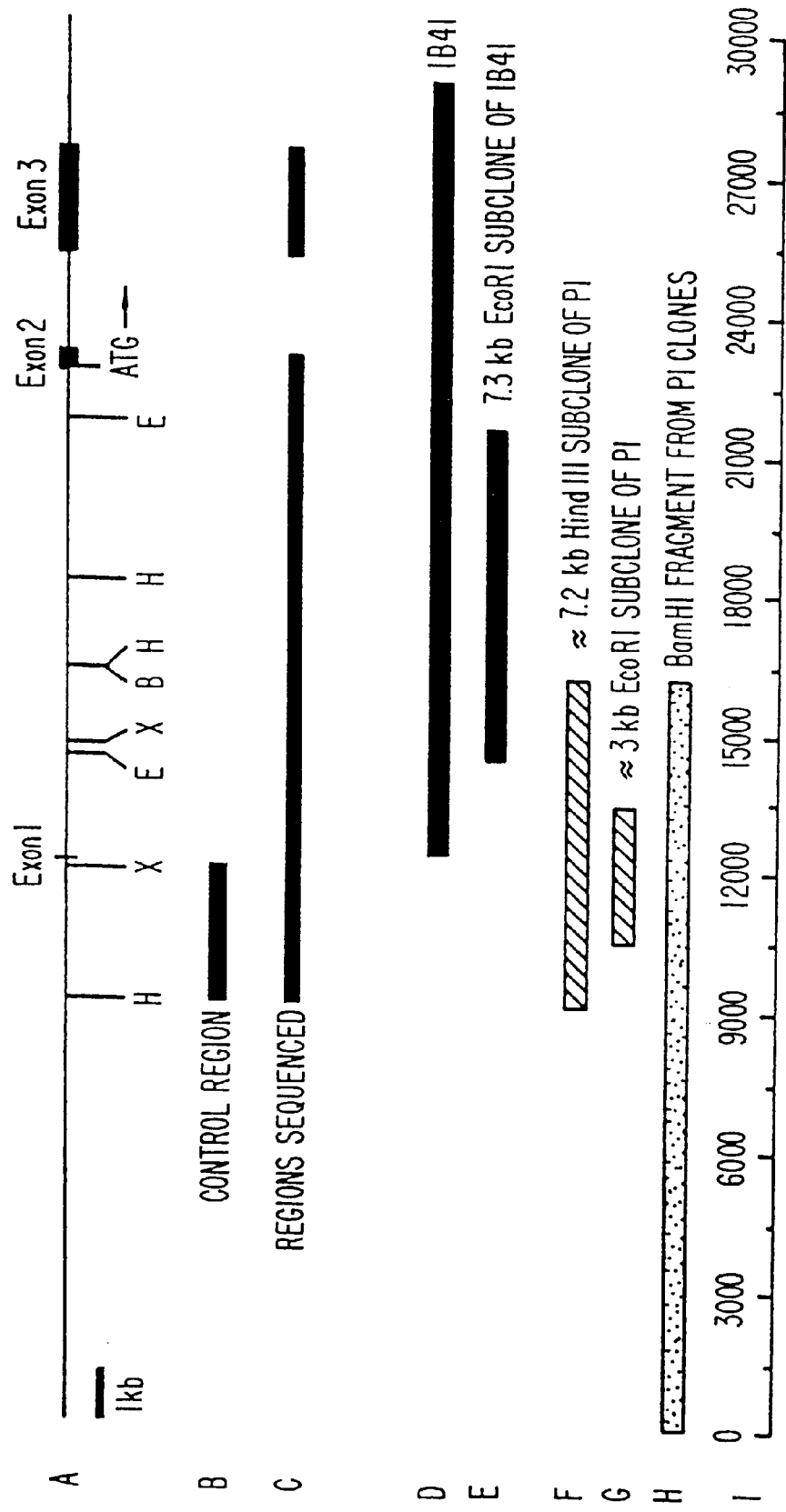

The present invention describes that the human ob gene has two introns and three exons (see FIG. 9). The novel nucleic acid sequences of the present invention comprise the ob gene control region such as (1) sequences which provide a positive promotion of transcription, i.e., promoters and enhancers; or (2) sequences which provide a negative regulation of transcription, e.g., silencers. Other mammalian ob gene control regions may be isolated by the methods described below and by hybridization of other mammalian DNA libraries with probes derived from the human ob gene control regions.

Oligonucleotide primers

The oligonucleotides used for various aspects in this application are listed below (whereas N1=G, A, or C; and N=G, A, C, or T):

```
1F:         5'-ATG CAT TGG GGA ACC CTG TGC GG-3'                    (SEQ ID NO:5)

140R:       5'-TGT GAA ATG TCA TTG ATC CTG GTG ACA ATT-3'           (SEQ ID NO:6)

217R:       5'-GAG GGT TTT GGT GTC ATC TTG GAC-3'                   (SEQ ID NO:7)

562R:       5'-CCT GCT CAG GGC CAC CAC CTC TGT CG-3'                (SEQ ID NO:8)

anchored-T: 5'-TTC TAG AAT TCA GCG GCC GC(T)30N1N-3'                (SEQ ID NO:9)

AP1:        5'-CCA TCC TAA TAC GAC TCA CTA TAG GGC-3'               (SEQ ID NO:10)

AP2:        5'-ACT CAC TAT AGG GCT CGA GCG GC-3'                    (SEQ ID NO:11)

pdv34R:     5'-GCC ACA AGA ATC CGC ACA GGG TTC CCC ATG C-3'         (SEQ ID NO:12)

RACE1:      5'-CTC TTA GAG AAG GCC AGC-3'                           (SEQ ID NO:13)

RACE2:      5'-CGC GGG CTC GAG AAG GTC AGG ATG GGG TGG AGC-3'       (SEQ ID NO:14)

SMFOR:      5'-CGC AGC GCC AAC GGT TGC AAG GC-3'                    (SEQ ID NO:15)

SMREV:      5'-GCC TTG CAA CCG TTG GCG CTG CG-3'                    (SEQ ID NO:16)

SMREV2:     5'-CGC GGG AAG CTT GCC TTG CAA CCG TTG GCG CTG CG-3'    (SEQ ID NO:17)

MUT1a:      5'-GAG CCT CTG GAG GGA CAT CA-3'                        (SEQ ID NO:18)

MUT2a:      5'-TGG CGT CTT CCA TGG GGT CT-3'                        (SEQ ID NO:19)

CEBPfor:    5'-GCC TGC GGG GCA GTT AAA AAA GTT GTG ATCG-3'          (SEQ ID NO:20)

CEBPrev:    5'-CGA TCA CAA CTT AAA AAA CTG CCC CGC AGG-3'           (SEQ ID NO:21)

OB/S1       5'-GCT TCT TGG GCC TTG CAA CCG TTG GCG CTG CGA TTC
CTA         CGG GGC TCC ATG CCT GC-3'                               (SEQ ID NO:22)
```

Cloning mouse ob cDNA

A mouse ob cDNA fragment spanning nucleotides +50 to +659 was cloned from mouse adipose tissue by reverse transcription and PCR-amplification (sense primer. 5CCA AGA AGA GGG ATC CCT GCT CCA GCA GC - 3' (SEQ ID NO:23) anti-sense primer. 5t CCCTCT ACA TGA TTC TTG GGT ACC TGG TGG CC-3') (SEQ ID NO:24) (Zhang et al., Nature 372:425–432, 1994). The resulting PCR-fragment was digested with BamHI and KpnI and cloned into the BamHI and KpnI site of pBluescript KS to generate pmob.1. Sequence analysis of pmob.1 revealed complete identity to the reported mouse ob cDNA sequence (Zhang et al., Nature 372:425–432, 1994).

Cloning human ob cDNA

A human adipose tissue λgt11 library was next screened with the complete mouse ob cDNA as a probe. Duplicate filters were prepared and hybridized with $^{32}$P-labeled (random priming: Boehringer Mannheim) BamHI-KpnI fragment of mouse ob cDNA clone pmob.1. After hybridization filters were washed in 0.2×SSC and 0.1% SDS for 10 min at room temperature (about 20–25° C.)and twice for 30 minutes in 1×SSC, 0.1% SDS at 50° C. and subsequently exposed to X-ray film (X-OMAT-AR, Kodak). Several positive clones which gave signals on both duplicate filter lifts were obtained and one of them, ob 6.1 was characterized in detail. A 1.6 kb EcoRI fragment of this clone starting about 90 bp upstream of the ATG start codon and extending downstream into the 3'UTR sequence was subcloned into the EcoRI site of pBluescript SK-, to generate phob 6.1. The sequence of the 5'UTR region is 5'- GGC CCC TGA CCA CCA GGA ACT GAA CCT TGA TGC GTC CCT CCA ACT GCC CAG CCG CAG CTC CAA GCC AAG AAG CCC ATC CTG GGA AGG AAA ATG -coding region -3' (SEQ ID NO:25). Sequence analysis of phob 6.1 confirmed it as being the human homologue of the mouse ob cDNA (Zhang et al., Nature 372:425–432, 1994).

Isolating human genomic ob clones

The genomic library was derived from female leucocyte DNA partially digested with Sau3A and inserted into λDASHII arms. The library contains 5×10$^5$ independent recombinants and has an insert size between 15–20 kb.

For the initial screening, a $^{32}$P-labeled (random priming; Boehringer Mannheim) unique BamHI-KpnI fragment of mouse ob cDNA clone pmob 1 was used as a probe. Filters were washed in 2×SSC, 0.1% SDS for 10 minutes at room temperature and twice in 0.1×SSC, 0.1% SDS at 65° C. for 30 minutes. During this round of screening 8 positive plaques were identified.

In the first purification step, the $^{32}$P labeled (random priming: Boehringer Mannheim) 1.6 kb insert released by Eco RI from phob 6.1 was used as a probe, and the treatment of the filters was identical as in the initial screening.

Two genomic phage clones were retained and they were termed 1B41 and 1F41. Both clones were again positive upon the second round of purification and were verified to be pure. Clone 1B41 contains an insert of approximately 17 kB, whereas 1F41 has an insert of 13 kb which overlaps to a large extent with clone 1B41. These clones were further characterized by restriction analysis with the restriction enzymes EcoRI, Hind III, and Xho I, and a restriction map is presented in FIG. 6.

In order to further characterize these clones a set of PCR reactions were performed. Initially we verified whether the entire coding region was contained in our genomic clones. PCR amplifications using the 1F/217R primers resulted in the appearance of a 102 bp band when either genomic DNA, the 1B41 and 1F41 genomic clones, or the phob 6.1 cDNA were used as template, suggesting that both primers were localized in a single exon. When PCR reaction was carried out with the 1F/562R primers, a 2.5 kb band was amplified from human genomic DNA and from the 1B41 and 1F41 genomic clones.

However, amplification on the phob 6.1 cDNA with 1F and 562R primers resulted in the appearance of a 447 bp fragment consistent with the presence of an intron in the region confined between 217R and 562R. These data suggested that the 1B41 and 1F41 clones contained the entire coding region of the human ob gene as well as intron genomic sequences.

The 1B41 and 1F41 clones hybridized with oligonucleotide 1F, which covers the ATG start codon and with oligonucleotide 562R, localized in the 3'region of the coding sequence indicating that the entire coding sequence was contained in these clones. Further, sequencing of 1B41 in the 5' direction using oligonucleotides ob 1 (5' CATTTTCCT-TCCCAGGATG 3') (SEQ ID NO:26), ob7, and P1 has yielded sequence information diverging from the cDNA sequence of clone phob 6.1 (no homologous sequence is found in Genbank) (from 5' to 3', see sequence ID No. 3).

Cloning the entire human ob gene in P1 plasmid

In order to isolate genomic P1 plasmid clones containing the entire human ob gene, the primer pair 1F/140R were used to amplify a 140 bp probe with the phob 6.1 plasmid as a template. This fragment was then used to screen a P1 human genomic library. P1 library is from human foreskin fibroblast (Sternberg et al., *New Biologist* 2:151 (1990); *Trends in Genetics* 8(1), January 1992).

A number of hybridizing clones (about 100) yielded from the primary screen of the P1 library. The screening can be repeated with the novel 5' flanking sequence from the 1B41 clone with the primer pair ob 1 and kenobe (5' TGGGT-GAGTACCATAATCGC 3') (SEQ ID NO: 27)to identify clones containing the ob gene 5' flanking sequences. Primer pair 1F and 140R was used to generate a probe to screen the P1 clones.

Three positive clones were isolated and termed 5135, 5136, and 5137. All three clones were shown to hybridize with the following oligonucleotides 1F, ob 1, 562R and 140R as well as kenobe oligos at the extreme 5' sequence obtained from the 1B41 clone, thus demonstrating that the sequence 5' to the coding region of the ob gene is contained in these Pi clones. Standard molecular biology techniques were used to further characterize the 5' regions of the ob gene to locate control regions, such as detailed restriction analysis, genomic sequencing of the 5' regions of the ob gene contained within the P1 clones, and primer extension and S1 mapping analysis of human adipose tissue.

Determining the transcription initiation site of the ob gene 5'-RACE

The Marathon cDNA amplification kit (Clontech) was used for 5'-Rapid Amplification of cDNA Ends (RACE) to obtain the sequence of the 5' untranslated region (5'-UTR) of the human ob gene transcript. The 5'-RACE was performed on total RNA (1 μg) from several independent human white adipose tissue samples and on double stranded cDNA derived from human adipose tissue (Clontech). The anchored-T primer included in the kit or the ob-specific primer 562R were used to prime first strand synthesis on adipose tissue RNA and second strand synthesis was performed according to the instructions provided by the manufacturer. PCR reaction products were recovered, ligated into the TA cloning vector pCRII (InVitrogen), and sequenced.

Total human white adipocyte tissue (WAT) cellular RNA was prepared by the acid guanidinium thiocyanate/phenol chloroform method (Choeczynski, et al., *Analytical Biochemistry* 162:156–159, 1987)

First-strand cDNA synthesis was performed in parallel reactions, each using 1μg of total RNA isolated from human white fat as template. One reaction utilized an anchored-T primer to prime first strand synthesis. A second reaction utilized a primer specific for human ob (562R) for first strand synthesis.

An anchored-T primer, included in the Clontech kit, was used to prime first strand synthesis. After synthesis of double-stranded cDNA and anchor ligation, polymerase chain reaction was carried out using the following primer sets: AP1/140R, AP1/RACE1 and AP1/RACE2.

The 5' ends of these primers are located at +140 bp (140R), +215 bp (RACE2), and +347 bp (RACE1) relative to the ATG start codon of the open reading frame of human ob gene. The anchor primer AP1 is provided in the Clontech kit. A fraction of the primary 5'-RACE product derived from this PCR reaction was run on a polyacrylamide gel and products were visualized by staining with ethidium bromide. A band of about 360 bp was obtained.

5'-RACE was also carried out using double stranded cDNA derived from human fat tissue obtained from Clontech (Part #7128-1). The anchors included in the Marathon kit were ligated to this cDNA and PCR amplification and cloning carried out as described above. The products of the PCR step were separated on an agarose gel and visualized with ethidium bromide. The major bands were recovered from a low melting point agarose gel and ligated into the TA cloning vector pCRII (InVitrogen).

A parallel set of ligations were performed using the 5'-RACE PCR product without purification. The clones obtained were sequenced using the 140R primer.

Secondary PCR was carried out on aliquots of the primary 5'-RACE product using the primer sets AP1/217R, AP2/217R or 1F/217R. The primer AP2 anneals to sequences located within the 5'-RACE anchor and is nested relative to the AP1-binding sequence. A product of about 360 bp was recovered from both the AP1/217R and AP2/217R PCR reactions and a product of about 100 bp was recovered from the 1F/217R PCR reaction.

The product from the 1F/217R PCR reaction was the size expected from the human ob sequence and comigrated with the product of parallel PCR reactions carried out using 1F/217R and either the human ob cDNA clone phob6.1 or the human genomic clone 1B41 as template. Therefore, the primary 5'-RACE product contains authentic human ob sequence and the full length human white fat mRNA contains a 5' untranslated region of about 260 bp.

The product of the AP2/217R PCR reaction was ligated into the vector pCR-Script SK(+)(Stratagene) using the methods described by the manufacturer. The cloned inserts were sequenced on both strands. The AP2/217R PCR product was also subjected to direct DNA sequencing using cycle sequencing.

A. 5' RACE with RNA

Sequence was obtained from four independent 5'-RACE clones (Clones 1–4; Table 1) using a sequencing primer located within the coding region of human OB (140R). The sequences are listed in Table 2.

Sequences shown above are from the region between the AP1 5'-RACE primer and the ATG start codon (bold) for the initiating methionine of human ob protein. The underlined regions indicate sequences that diverge from the genomic sequence (see Table 4 for comparison).

Clones 1, 2 and 3 were obtained using primers 140R and AP1 for PCR. Clone 4 was obtained using primers RACE1 and AP1.

B. 5' RACE with cDNA

A second set of 5'-RACE reactions were carried out using human adipose tissue double-stranded cDNA (obtained from Clontech) as starting material. Sequence was obtained from three clones (clones 5–7; Table 3). These sequences were identical to one another and to the 5'-RACE sequences obtained from the independent tissue source shown above. These clones were 3 base pairs shorter than the longest 5'-RACE clone obtained using human adipose total RNA as a starting material.

Sequences shown above are from the region between the AP1 5'-RACE primer and the ATG start codon (bold) for the initiating methionine of human ob protein. The underlined regions indicate sequences that diverge from the genomic sequence (see Table 4 for comparison).

These clones were obtained using the primers 140R and AP1 for PCR.

The sequences of all seven clones diverge from the genomic sequence 26 bp 5' from the initiating ATG of the human ob reading frame (Table 4).

Genomic Clone (2) is shown relative to the sequence of human genomic DNA in this region. Regions of sequence identity are indicated (|), the novel sequence is underlined. The following experiment was carried out to map the 5' exon on human genomic P1 clones.

Primer extension

The oligonucleotide pdv34R was $^{32}$P-labeled and used for the primer extension reaction at $10^5$ dpm per 50 µg adipose tissue total RNA from different subjects in a final reaction volume of 100 µl. The reaction mix was precipitated and the primer extension reactions were carried out using standard methodologies with a mixture of 1.25 Units of AMV reverse transcriptase (BRL) and 100 Units MMLV reverse tran scriptase (BRL). Reaction products were phenol/chloroform extracted, precipitated, dissolved in formamide loading buffer and run on a 10% denaturing acrylamide gel. A sequencing reaction of an ob cDNA clone with the same primer was run in parallel to map the position of the extension products.

FIG. 14 shows human and rat ob gene transcription initiation sites as mapped by 5'-RACE and primer extension.

S1 analysis 50,000 cpm of a 5' $^{32}$P-labeled, gel-purified oligonucleotide probe OB/S1 was annealed (14 hr, 30° C.) to 50 µg adipose tissue total RNA from different subjects in 20 µl hybridization buffer. A 10 µl aliquot of the annealing reaction was subjected to S1 nuclease digestion according to the manufacturer's protocol (Ambion) and the reaction products analyzed on a 10% denaturing gel. A $^{35}$S-labeled 10-nucleotide ladder was used as a size standard. This method confirmed the most 5' start site as identified by primer extension assay.

Mapping the 5' exon of the human ob gene in the P1 clones

A. Identifying and isolating the 5' intron on human genomic P1 clones by PCR

Two oligonucleotides, SMFOR and SMREV, were synthesized based on the sequence obtained from 5'-RACE. SMFOR and SMREV are reverse complements of one another. Extended PCR was carried out on three human genomic P1 clones (5125, 5126, 5127) using SMFOR and 140R as primers.

An identical PCR product of approximately 10–12 kb was obtained using all three P1 clones. Amplification of this band required the presence of both primers and template. No product was obtained when the human genomic λ clone 1B41 was used as template.

This data indicates that an intron of approximately 10–12 kb is present in the primary transcript of the human ob gene. The exon within which the SMFOR/SMREV sequence is located ("5' exon") is not contained in the genomic clone 1B41 but is present in the three P1 clones. All three P1 clones hybridized with oligos from the 5' (1F) and 3' (562R) extremes of the coding sequence as well as the oligo SMFOR derived from the 5' RACE, and hence contain the transcription initiation site of the ob gene.

B. Locating the 5' exon on the P1 clones by restriction mapping

To localize the 5' exon within each of the three P1 clones, the clones were digested with either BamHI, EcoRI, HindIII or NotI. The restriction digests were separated on agarose gels, transferred to nitrocellulose, and probed by Southern hybridization using [$^{32}$P]-labeled SMFOR as a probe.

A single major band was detected in each digest. The sizes of the hybridizing bands were identical for all three P1 clones in the EcoRI (approximately 3 kb), HindIII (approximately 7.2 kb), and NotI (>20 kb) digests. The sizes of the hybridizing bands were different for each of the three clones when digested with BamHI (5125≈11 kb; 5126≈14 kb; 5127 (–12 kb). The BamHI results indicate that the 5' exon is located within approximately 11–14 kb of one end of each of the P1 inserts.

The EcoRI fragment and HindIII fragment from the P1 clone containing the 5' exon were subcloned into pBSII-SK+, respectively (see FIG. 9 for the location of the EcoRI and HindIII fragments.

Sequence obtained from the HindIII subclone using the M13 -20 flanking primer (the HindIII site is underlined):

```
5'   AAGCTTCTTT AAGGATGGAG AGGCCCTAGT GGAATGGGGA GATTCTTCCG

GGAGAAGCGA TGGATGCACA GTTG -3' (SEQ ID NO:28)
```

Sequence obtained from the HindIII subclone using the T3 flanking primer (the HindIII site is underlined and a BamHI site is double underlined):

```
5'-  AAGCTTTAGC TAGTCTGAGT CCTCTCCCTA TACACATTCT CCTGTGGGAT

CCCCTCCTG -3' (SEQ ID NO:29)
```

This sequence is identical to a region of genomic sequence localized within the 10–12 kb intron approximately 6.4 kb 5' of the initiating ATG. The location and orientation of this HindIII clone is shown in FIG. 9.

Sequence obtained from the EcoRI subclone using an M13 -20 primer (the EcoRI restriction site is underlined):

```
5'-  GAATTCCTAC CCGCAGAGCA AGGCAATGTC TGGGACTGAG ACTGATCACT

TGCATCTGCG TCTCTCCTAN NCCCAACTTT ATCTCCTTCA GACTGGGGTG

GGACATCTGA TCTTTGGG  -3' (SEQ ID NO:30)
```

Sequence obtained from the EcoRI subclone using a T3 primer (the EcoRI restriction site is underlined):

```
5'-  GAATTCAAAA CTTTATAGAC ACAGAAATGC AAATTTCCTG TAATTTNNCC

GTTGAGAACT ATTCTTCTTT  -3' (SEQ ID NO:31)
```

The following sequence was obtained from both the HindIII subclone and the EcoRI subclone using the SMREV primer:

```
5'-  ACTGCCCCGC NGGCCCCGGC GCATTTCTAG CGCCAGCTCC CGCCCCGCCC

CTTCAGGTAG CGACAGTGCC GGGCGGCTGC TAGCCCTGGG CCCGCAGTGT

GCACCTCGCG GGGCCTCGAG GGAGGGC -3' (SEQ ID NO:32)
```

The letter "N" indicates an ambiguous base. The region upstream of the 5' exon contains a control region regulating ob gene expression. Two SP1 binding sites are double underlined.

FIG. 15 shows the splicing pattern in human genomic ob gene. Transcription starts at Exon 1, goes through Intron 1 to reach Exon 2. The translation start codon ATG is located inside Exon 2.

Physical map of the human ob gene.

The results indicated above were used to generate a physical map of the human ob gene locus (FIG. 9). Three exons and two introns exist within the primary transcript of the human ob gene. Promoter and control regions are present in the region immediately upstream of the 5' exon within the HindIII subclone. Addition genetic control regions may be present within the 5' intron.

As shown in FIG. 15, Sequence I.D. No. 1 represents 294 bp of the proximal promoter region, upstream of the transcriptional initiation site as determined by primer extension. A C/EBP binding site (5' TTGCGCAAG 3' (SEQ ID NO:33)) and an XhoI site (5° CTCGAG3') are located within Sequence I.D. No. 1. Sequence I.D. No. 2 represents the entire sequence of Exon 1. Sequence I.D. No. 3. represents the entire sequence of Intron 1, starting at the nucleotide 3' to Exon 1, and extending to the nucleotide 51 to Exon 2. Seq. I.D. No. 4 starts at the HindIII site immediately upstream of Exon I and ends at sequence -1, the nucleotide 5' next to the transcription initiation site. There are PPRE half sites, GRE sites, and a TATA box sequence (5' TATAAGA 3' (SEQ ID NO:34)) in Seq. I.D. No. 4.

The human ob gene's three exons cover approximately 15 kb of genomic DNA. The entire coding region is contained in exons 2 and 3, which are separated by a 2 kb intron. The first small 30 bp untranslated exon is located >10.5 kb upstream of the initiator ATG codon. 3 kb of DNA upstream of the transcription start site has been cloned and characterized.

Delineating ob gene promoter and other control regions

Segments of DNA from the 5' upstream region of the transcription initiation sites were assayed for their transcription regulation activities.

A. Construction of ob promoter-luciferase reporter vectors

To test the activity of the human ob promoter, several reporter constructs were made. A 7 kb HindIII fragment of P1 clone 5135 that hybridized to oligo SMFOR, was subcloned into the HindIII site of pBluescript (Stratagene). From this construct a fragment of about 3 kb in length, containing sequences from about −3 kb (5' HindIII site) to +31 relative to the transcription start site, was amplified by PCR with Vent polymerase using the HindIII subclone as template. The primers used were M13(−20) (5'-GTAAAACGACGGCCAGT-3' (SEQ ID NO:33)) and SMREV2 (containing a HindIII site). The PCR product was digested with HindIII and ligated into the HindIII site of the promoterless luciferase reporter vector pGL3-Basic (Promega) to generate pGL3-OB1 (51 HindIII site to +31) and sequenced to confirm orientation.

To avoid any errors introduced by the PCR step, an approximately 2.8 kb Asp718 fragment of pGL3B-OB1 was replaced by an equivalent fragment isolated from the 7 kb genomic HindIII clone in BlueScript. This plasmid was designated pGL3B-OB3 and represents a more authentic version of pGL3-OB1.

A third luciferase reporter vector, was constructed by digesting pGL3B-OB1 with Asp718 (or KpnI which is an isoschizomer of Asp718) and religating the Asp718(KpnI)-HindIII subfragment, spanning from −217 to +31, into the gel-purified vector backbone. This reporter vector was designated pGL3B-OB2 or pGL3-OB2.

A fourth luciferase reporter vector, containing −170 to +31, was constructed by digesting pGL3B-OB1 with XhoI and religating into the gel-purified vector backbone. This plasmid was designated pGL3B-OB4.

The orientation and construction of pGL3B-OB1, pGL3B-OB2, pGL3B-OB3 and pGL3B-OB4 are shown in FIG. 16(a)–(d). In this application, pGL3B-OB1 and pGL3-OB1 are interchangeable, so are pGL3B-OB2 and pGL3-OB2, pGL3B-OB3 and pGL3-OB3, and pGL3B-OB4 and pGL3-OB4.

The C/EBPα mutant construct pGL3-KOB1 was constructed using the mismatch PCR technique. Briefly, an oligonucleotide corresponding to sequences 5' to the Asp 718 in pGL3-OB1 (MUT1a) and a 3' oligo outside the multiple cloning site (MUT2a) and two additional oligos encompassing the C/EBP site (CEBPfor and CEBPrev) were synthesized. The first PCR step involved amplification with pGL3-OB1 as template and the primer pairs CEBPrev+MUT1a in one reaction and CEBPfor+MUT2a in a second reaction. The gel isolated products were pooled and reamplified with MUT1a+MUT2a primers. The resultant PCR product was digested with NcoI and Asp718 and subcloned into NcoI and Asp718 digested pGL3-OB1 and sequenced to confirm the mutant sequence. The pMSV-C/EBPα (Christy, et al., *Genes and Development* 3:1323–35, 1989) expression vector is described elsewhere.

Transfections were performed using either standard calcium phosphate precipitation techniques (Schoonjans, et al., *J. Biol. Chem.* 270:19269–19276, 1995) or electroporation for primary adipocytes (Quon, et al., *Biochem. Biophys. Res. Commun.* 194:338–346, 1993). Luciferase assays were carried out exactly as described previously (Schoonjans, et al. *J. Biol. Chem.* 270:19269–19276, 1995). pGL3-Basic and pGL3-Control (Promega, Madison, Wis.) were used as transfection controls for comparison across the cell lines. Relative expression of the pGL3-OB plasmids in pre-adipocytes was several fold lower than the primary adipocytes (raw luciferase values of ~5,000 vs. ~25,000 in a comparable assay) and the data are presented as relative levels within a given cell type.

B. Calcium phosphate transfection

3T3-L1 cells or other cell lines were plated at ~60% confluency and allowed to adhere to the plate overnight. The following day calcium phosphate DNA precipitates containing 2 µg of pGL3B-OB1 DNA were prepared and added to the cells for 8 hours. The cells were washed and refed with media containing 10% FBS and 200 µM insulin. After 48 hours the cells were washed and lysed for luciferase measurements using standard commercial reagents and protocols (Promega).

C. Assaying for tissue specific promoter activity

The expression of the ob mRNA is specific for adipose tissue and strongly regulated in rodents (Frederich, et al., (1995) *J. Clin. Invest* 96:1658–1663; MacDougald, et al., (1995) *Proc. Nat. Acad. Sci. USA* 92:9034–9037; Saladin, et al., (1995) *Nature* 377:527–529; Trayhurn, et al., (1995) *FEBS Let.* 368:488–490; DeVos, et al., (1995) *J. Biol. Chem* 270:15958–15961; Murakami, et al., (1995) *Biochem. Biophys. Res. Commun.* 214:1260–1267).

A region containing the proximal promoter is shown below:

```
(-220)
GGAGGTACCCAAGGGTGCGCGCGTGGCTCCTGGCGCGCCGAGGCCCTCCCTCGAGG
      KpnI                                              XhoI

CCCCGCGAGGTGCACACTGCGGGCCCAGGGCTAGCAGCCGCCCGGCACGTCGCTACCCTGA

GGGGCGGGGCGGGAGCTGCGCTAGAAATGCGCCGGGGCCTGCGGGGCAGTTGCGCAAGTTGT
   SP1                                                  C/EBP

GATCGGGCCGCTATAAGAGGGGCGGGCAGGCATGGAGCCC  (-1) CGTAGGAATC
           TATA

GCAGCGCCAA CGGTTGCAAG (+30)  (SEQ ID NO:34)
```

An AT-rich sequence 31 bp upstream of the transcription initiation site, TATAAGA, resembles a TATA box. The sequence immediately upstream of the transcription initiation site is extremely GC-rich, including several consensus Sp1 binding sites, implicating Sp1 in the expression of this gene. A C/EBP protein binding site is located at −45.

There are potential binding sites for the insulin responsive ETS family members SAP-1 and ELK-1 further upstream from the proximal promoter. Consensus sites containing CGGA or its complement TCCG are set in bold face and underlined in SEQ. ID NO. 4 (Jacob, et al. *J. Biol. Chem.* 270:27773–27779, 1995). CTTCCG, TCTCCG, and TCCGCGGA as indicated in SEQ ID NO.4 are likely to mediate insulin response of this ob promoter. Similar sites have been found in the insulin responsive genes somatostatin, thymidine kinase and prolactin, and several other genes which are regulated at the transcriptional level by insulin including phosphoenolpyruvate carboxykinase, glyceraldehyde 3-phosphate dehydrogenase and growth hormone. Id.

pGL3-OB1 was transfected into primary rat adipocytes, mouse 3T3-L1, CV-1 and COS cells. FIG. 17(B) shows the basal level of the human ob gene promoter activity in 3T3-L1 cells as compared to the control plasmid (pGL3B-Basic) with no ob promoter. FIG. 17(B) also shows that the ob promoter enhanced luciferase expression two-fold in response to insulin whereas the control was unaffected.

Relative to the promoterless parent vector the human ob promoter fragment stimulated luciferase expression up to 15-fold in primary rat adipocytes (FIG. 18). In the 3T3-L1 cells maintained under non-differentiating conditions, luciferase expression was 10- to 15-fold higher in the pGL3-OB1 transfected cells relative to the pGL3-Basic vector. In CV-1 cells, the same ob promoter fragment induced luciferase expression by <2.5-fold. Similar results were obtained with COS cells. These results are consistent with the observation that ob mRNA expression is primarily observed in adipocytes and preadipocytes. The results show that the sequences necessary for adipocyte lineage specific expression of the ob gene are contained within the 3 kb HindIII fragment in pGL3-OB1 and suggest the existence of tissue-specific regulatory elements.

To further define areas within this 3 kb region that are important for ob gene expression in adipocytes, pGL3-OB2 was used to transfect primary rat adipocytes, 3T3-L1 and CV-1 cells. pGL3-OB2 had comparable promoter activity to pGL3-OB1 in adipocytes, while the expression in non-adipocyte lineages remained low (FIG. 18C). The difference in expression level between adipocytes and cells from different origins suggests the existence of the region necessary for basal expression of ob gene and tissue-specific regulatory elements localized to the proximal 217 bp as evidenced by the robust expression of pGL3-OB2.

D. Delineating other control regions C/EBPα site

Adipocyte differentiation has been shown to be determined by the coordinately acting transcription factors PPARγ (Freytag, S. O. & Geddes, T. J. (1992) *Science* 256:379–382) and various members of the C/EBP family (Schoonjans, et al.,. (1995) *J. Biol. Chem.* 270:19269–19276; Freytag, S. O. & Geddes, T. J. (1992) *Science* 256:379–382; Freytag, et al., (1994) *Genes and Development* 8:1654–1663) among others. Since we had identified a potential binding site for C/EBP in the promoter, we examined its role in the expression of the ob gene. Co-transfection of C/EBP with pGL3-OB1 or pGL3-OB2 in rat primary adipocytes as well as in 3T3-L1 preadipocytes induced ob promoter activity significantly (FIGS. 19A & B). In primary rat adipocytes, expression of both the 3kb promoter construct, pGL3-OB1, and the 217 bp construct, pGL3-OB2, were stimulated 2.5 to 4-fold. In 3T3-L1 cells, C/EBPα cotransfection stimulated the expression of the two reporter vectors pGL3-OB1 and pGL3-OB2 by about 2.5 fold. No significant effect was seen on the promoterless control.

The expression of the pGL3-OB1 reporter vector was furthermore induced in a concentration-dependent way by C/EBPα in rat primary adipocytes (FIG. 19C). The fact that the stimulation was seen with both the pGL3-OB1 and pGL3-OB2 constructs indicates that the sequence identified by computer search and contained within the 217 bps adjacent to the transcription initiation site was responsible for the increased luciferase expression.

To further test this hypothesis, we mutated the consensus C/EBP site at nucleotide positions −53 to −45 from TTGCG-CAAG (SEQ ID NO:37) to TTAAAAAG (SEQ ID NO:38) (mutant nucleotides underlined) in the pGL3-OB1 vector. When the mutant C/EBP construct pGL3-KOB1 was introduced into primary rat hepatocytes, basal luciferase expression was reduced by more than 30% and the 2-fold stimulation of the wild-type promoter construct seen upon co-transfection with C/EBPα was absent, demonstrating that in the 3 kb promoter, this site was functional in mediating the effect of C/EBPα on ob gene expression.

The function of the Sp1 binding site can be analyzed using the same approach. Sp1 protein and its binding site are co-factors for basal and regulated transcription for genes such as the LDL receptor. The Sp1 binding site may be another positive transcription element for the ob gene promoter. In that regard, a Sp1 agonist would be an up regulator whereas a Sp1 antagonist would be a down regulator for the ob gene expression.

Negative regulators

Deletion constructs are useful for identifying and dissecting the control regions of the 51 promoter sequences. So are internal deletions and scrambled mutations for characterizing individual factor binding sites as demonstrated above for the C/EBP site. Nested deletions of the pGL3-OB1 construct were made as follows: The pGL3-OB1 vector was digested with SacI and MluI and treated with exonuclease III and S1 nuclease as described (Henkoff, *Gene* 28:351–359, 1984). The DNAs were treated with Klenow, ligated overnight at 20° C., and used to transform *E. coli* XL1-Blue cells. Positive clones were analyzed by restriction digestion and dideoxy-sequencing.

The deletion constructs that were selected for further experiments were pGL3-OBΔ5, containing sequences from −1869 to +31, and pGL3-OBΔ12, which contained sequence from −978 to +31, both relative to the transcription initiation site. The hamster expression vector pSG5-cgPPARγ was described elsewhere (Aperlo, et al., *Gene* 162:297–302, 1995).

pGL3-OB1, pGL3-OB2, pGL3-OBΔ5, pGL3-OBΔ12, and control plasmid without ob gene promoter were transfected into 3T3-L1 cells together with pSG5 or pSG5-cgPPARγ. The presence of PPARγ consistently downregulates the expression from the human ob gene promoter as was demonstrated for the endogenous gene expression in animals and cultured rat adipocytes treated with PPARγ agonists.

As shown in FIG. 25, deleting sequences localized upstream of −1869 or −978 from the transcription initiation site increased the level of expression of the ob promoter. This suggests the presence of negative transcription elements suppressing the ob gene transcription in the regions from −217 to −978 and to −1869. Since interference with the function of these negative transcription elements would allow a higher level of ob gene expression and augmenting the activity of these negative transcription elements would reduce the level of ob gene expression, this invention envisions screening for modulators of these negative transcription elements and using deletions and mutations to further isolate control regions from −217 to −1869.

The following clones are tested for transcription activity: pGL3-OB4 (−170 to +31), pGL3-OBΔ8 (−2411 to +31), pGL3-OBΔ14 (−1716 to +31), and pGL3-OBΔ2 (−2382 to +31).

II. Screening for Modulators of ob Gene Expression

Cloning of the control regions of the ob gene provides a powerful tool for dissecting the role of the ob gene product in obesity and other metabolic disorders, including diabetes, cardiovascular disease, cachexia and anorexia. It also provides novel tools for discovering pharmacologic modulators of ob gene expression.

The utility of such genetic control elements is far-ranging, extending from their use as tissue specific promoters to drive heterologous gene expression to the fine-tuning of metabolic processes involved in energy, carbohydrate and fat metabolism. The identification and characterization of the promoter, enhancer and silencer regions of the ob gene allows us to identify and understand the discreet control elements involved in the control of the ob promoter, likely including among others glucocorticoid response elements (GRE), peroxisome proliferator response elements (PPRE), thyroid hormone response elements (TRE), retinoic acid response elements (RARE), retinoid X response elements (RXRE), estrogen response elements (ERE), progesterone response elements (PRE), androgen response elements (ARE), insulin receptor response elements, as well as transcription regulatory binding sites for the helix-loop-helix family members sterol regulatory element binding protein family (SREBP) or its adipocyte expressed homologue ADD-1, CAAT/enhancer binding protein (C/EBP), AP-1, and growth hormone (GH). Such elements are important for the development of screening assays for modulators of ob gene expression.

Therefore, a primary utility of the present invention is to provide a model system in which to study the effects of candidate compounds of the classes described herein and by reference, acting upon the transcription factor classes a described herein among others and general transcription machinery of the cell to modulate the transcription, either negatively or positively, of the ob gene itself or of a reporter gene subcloned in place of the coding sequence of the ob gene.

Assay systems using cells

The host cells used in the screening assay herein generally are mammalian cells, and preferably are human cell lines.

Mammalian cells of choice are preadipocyte or adipocyte, e.g., 3T3-L1 or 3T3 F422A or ob 1771 (uninduced or induced to differentiate). In a preferred embodiment, isolated rat primary adipocytes are used as a model assay system to screen for ob gene modulators.

Isolated adipose cells are among the most responsive cells with respect to glucose transport and metabolism. They represent an ideal model to demonstrate insulin sensitivity. (BBRC 1993. 194:338–346). We used these cells as an assay system to observe the regulation of endogenous ob gene expression. These cells, whether derived from rodent, human or other mammalian species, can be used to monitor the expression of a reporter gene driven by ob gene control elements or regions.

Inguinal or epididymal fat pads from young rats are removed. Adipocytes are prepared by collagenase digestion (Rodbell, M. *J. Biol. Chem.* 239:375–380, 1964; and Karneli, E. et al. *J. Biol. Chem.* 256:4772–4777, 1981). Briefly, cells are washed and resuspended in DMEM at a cytocrit of approximately 40%.

Plasmid DNA containing the control regions of the ob gene operatively linked to a reporter gene is introduced into the adipose cells via electroporation technology (Quon, M. J. et al. *BBRC* 194:338–346, 1993).

Rat primary adipocytes were isolated and incubated in the presence of (a) insulin (100 nM), (b) dexamethasone (33 nM) (c) insulin and dexamethasone, or (d) without the presence of insulin or dexamethasone. After 48 hours of incubation total adipocyte RNA was prepared. 10 $\mu$g RNA per lane was electrophoresed on a gel and blotted to filters and probed with labeled mouse cDNA encoding the ob gene. Filters were washed and exposed to films.

The Northern blot showed that both dexamethasone and insulin stimulated production of the ob messenger RNA, and their stimulation effects were additive. Dexamethasone provided stronger stimulation of ob gene expression than insulin. Therefore, the rat primary adipocytes provide an assay system to evaluate the regulation and modulation of ob gene expression and a screen for ob gene modulators.

Other cell lines may also be used, for example, HeLa, CV-1, HepG2, 293, Hig 82, MCF-7, CHO, COS-1 through COS-7, HS578T, VERO, W138, BHK, and MDCK either transiently or more preferably stably transfected or otherwise expressing such reporter constructs provided that the ob gene control sequence used in such a heterologous system influences transcription from the heterologous gene.

Cell systems other than mammalian may also be used in the screening assays, such as Drosophila (SL-2, Kc or others) and yeast strains (permeabilized or not) such as *S. cerevisiae* or *S. pombe* provided that factors necessary for the adipocyte specific expression pattern can be incorporated.

Reporter sequences

Generally, reporter genes encode a polypeptide not otherwise produced by the host cell which is detectable by in situ analysis of the cell culture, e.g., by the direct fluorometric, radioisotopic or spectrophotometric analysis of the cell culture without the need to remove the cells for signal analysis from the culture chamber in which they are contained. Preferably the gene encodes an enzyme which produces colorimetric or fluorometric changes in the host cell which is detectable by in situ analysis and which is a quantitative or semi-quantitative function of transcriptional activation. Exemplary enzymes include luciferase, chloramphenicol acetyl transferase, $\beta$-galactosidase, secreted placental alkaline phosphatase, human growth hormone, esterases, phosphatases, proteases (tissue plasminogen activator or urokinase) and other secreted enzyme reporters and other enzymes whose function can be detected by appropriate chromogenic or fluorogenic substrates known to those skilled in the art.

A preferred example is *E. coli* $\beta$-galactosidase. This enzyme produces a color change upon cleavage of the indigogenic substrate indolyl-B-D-galactoside by cells bearing beta-galactosidase (see, e.g., Goring et al., *Science* 235:456–458 (1987) and Price et al., *Proc. Natl. Acad. Sci. USA* 84:156–160 (1987)). Thus this enzyme facilitates automatic plate reader analysis of ob control region mediated expression directly in microtiter wells containing transformants treated with candidate activators. Also, since the endogenous $\beta$-galactosidase activity in mammalian cells ordinarily is quite low, the analytic screening system using $\beta$-galactosidase is not hampered by host cell background.

Another class of reporter genes which confer detectable characteristics on a host cell are those which encode polypeptides, generally enzymes, which render their transformants resistant against toxins, e.g., the neo gene which protects host cells against toxic levels of the antibiotic G418 a gene encoding dihydrofolate reductase, which confers resistance to methotrexate or the chloramphenicol acetyltransferase (CAT) gene (Osborne et al., *Cell*, 42:203–212 (1985). Resistance to antibiotic or toxin requires days of culture to confirm, or complex assay procedures if other than a biological determination is to be made.

Other genes for use in the screening assay herein are those capable of transforming hosts to express unique cell surface antigens, e.g., viral env proteins such as HIV gp120 or herpes gD, which are readily detectable by immunoassays.

The polypeptide products of the reporter gene are secreted, intracellular or, as noted above, membrane bound polypeptides. If the polypeptide is not ordinarily secreted it is fused to a heterologous signal sequence for processing and secretion. In other circumstances the signal is modified in order to remove sequences that interdict secretion. For example, the herpes gD coat protein has been modified by site directed deletion of its transmembrane binding domain, thereby facilitating its secretion (EP 139,417A). This truncated from of the herpes gD protein is detectable in the culture medium by conventional immunoassays. Preferably, however, the products of the reporter gene are lodged in the intra-cellular or membrane compartments. Then they can be fixed to the culture container, e.g. microtiter wells, in which they are grown, followed by addition of a detectable signal generating substance such as a chromogenic substrate for reporter enzymes.

ob gene control regions

In general, an ob gene promoter is employed to control transcription and hence influence expression of the reporter gene. ob gene promoter is optionally combined with more potent promoters, e.g. the TK or SV40 early promoter described in the Examples infra in order to increase the sensitivity of the screening assay.

A preferred condition would be to use the sequences upstream or 5' to the transcription initiation site or the coding sequence as the control elements, with or without additional promoter elements such as a TATA sequence or other sequences as may be required and obvious to one practiced in the art of heterologous gene expression and with or without intron sequences fused to a reporter gene to measure the effects of candidate compounds added to the cell culture.

The ≈3 kb human genomic sequence upstream of the 5' exon in FIG. 9 is amplified by PCR with SMREV and the M13 -20 primers using the HindIII subclone in pBSII-SK+ as a template and ligated immediately upstream to the start codon of the reporter gene with or without additional control elements. The recombinant DNA so constructed is used to regulate the expression of a reporter gene in a cell line.

The ob gene promoter, whether a hybrid or the native ob gene promoter, is ligated to DNA encoding the reporter gene by conventional methods. The ob gene promoter is obtained by in vitro synthesis or recovered from genomic DNA. It is ligated into proper orientation (5' to 3') adjacent 5' to the start codon of the reporter gene with or without additional control elements. The region 3' to the coding sequence for the reporter gene will contain a transcription termination and polyadenylation site, for example the hepatitis B or SV40 polyA site. The promoter and reporter gene are inserted into a replicable vector and transfected into a cloning host such as *E. coli*, the host cultured and the replicated vector recovered in order to prepare sufficient quantities of the construction for later transfection into suitable eukaryotic host.

The screening assay typically is conducted by growing the ob gene promoter transformants (e.g. stably transformed) to a suitable state of confluency in microtiter wells, adding the candidate compounds to a series of wells, and determining the signal level after an incubation period that is sufficient to demonstrate a measurable signal in the assay system chosen. The wells containing varying proportions of candidates are then evaluated for signal activation. Candidates that demonstrate dose related enhancement of reporter gene transcriptions or expression are then selected for further evaluation as clinical therapeutic agents. Candidate compounds may be useful therapeutic agents that would modulate ob gene expression.

The ob gene control region, including, but not limited to, that included in the P1 clones (5135, 5136 and 5137) deposited at ATCC may be introduced into animals by transgenic techniques, such as those disclosed in PCT publication WO 94/18959, incorporated by reference herein.

Transgenic mice carrying the P1 clones described herein which contain the human ob gene locus of approximately 85 kilo bases with regulatory flanking sequences can be used both as a primary screening vehicle in which compounds can be administered and parameters such as feeding, weight and ob mRNA production can be measured along with other appropriate controls to effectively assess the changes in expression of ob mRNA as well as a means of corroborating primary compound positives.

Alternatively, the P1 clone DNA carrying the ob gene locus could be introduced into animals utilizing adenovirus drag technology in which the target DNA is admixed with poly-L-lysine and/or transferrin or asialoglycoprotein modified adenovirus and injected i.v. into the animal, resulting in expression of the foreign DNA (Wu et al., *JBC* 266:14338–14342, 1991; Yanow et al. 1993, *PNAS* 90:2122–2126). In a preferred embodiment, recombinant adenovirus carrying the exogenous DNA can be injected directly into fat deposits of mice, rats or other species as has been done previously in brain (Davidson, *Nature Genetics* 3:219, *Science* 259:988), muscle (Quantin, *PNAS* 89:2581) (Statford-Perricaudet *J. Clin. Invest.* 90:626), and tumors. These animal model assay systems are also useful in secondary characterization and study of compounds found to regulate ob gene expression identified in other assays.

Additionally, the coding region of the ob gene in this P1 clone construct can be replaced with a reporter gene as described above which could be then introduced into animals either via the standard transgenic practice or through the use of adenoviral drag or other methods of introducing foreign DNA into animals.

EXAMPLE 1

Assaying for modulators of ob gene expression

Since the ob gene is exclusively expressed in adipocytes, adipogenic factors likely play major roles in the expression and regulation of the ob gene. The expression of two important adipocyte transcription factors, PPARγ and C/EBPα, is induced during adipocyte differentiation and these factors are maintained in the mature adipocyte. Several adipocyte-specific genes have binding sites for these factors in their promoters and have been shown to be transcriptionally responsive to chemical modulators of these factors. The effect of C/EBPα on ob gene expression mediated by a C/EBP site in the proximal ob gene promoter has been shown in this application.

The effects of antidiabetic thiazolidinediones (TZDs), previously shown to be ligands for PPARγ (Lehmann et al., *Journal of Biological Chemistry* 270:12953–956, 1995, not admitted to be prior art), on expression of the ob gene were examined in vivo, ex vivo in primary adipocyte cultures, and in vitro in transfected cells.

In vivo assay in rats

To test the effects of drugs, rats were dosed once per day by oral gavage with vehicle alone or containing 1, 2 or 5 mg/kg body weight for seven days. At the end of the dosing period, the rats were sacrificed and tissues collected for mRNA analysis. Fat was collected for ob mRNA analysis and RNA samples were prepared from each individual animal (4 per group). Northern blot analysis was performed normalizing the ob mRNA signal to an actin signal as an RNA loading control.

The effects of the antidiabetic thiazolidinedione BRL 49653 on the expression of the ob gene was tested in vivo in rats. In animals receiving BRL 49653 at increasing doses (0, 1, 2, and 5 mg/kg/day) over 7 days no change in either body or liver weight was observed (Table 5). The absence of an effect on total body weight is likely due to the short time of treatment.

A dose-dependent increase in epidydimal fat pad weight was observed after BRL 49653 treatment (Table 5). The ratio of adipose tissue/body weight increased significantly (0.75%±0.1 before vs. 1.2%±0.2 after treatment; p<0.05) in animals treated with BRL-49653 (5 mg/kg/day), indicating that some remodeling of the body fat was occurring. BRL 49653 may contribute to fat redistribution in humans as well. Since the modulation of ob gene expression may be a part of the fat redistribution process, visceral fat increases associated with the metabolic syndrome or syndrome X may be controlled (e.g. increased or decreased) by ob gene modulators.

Figure 20B:
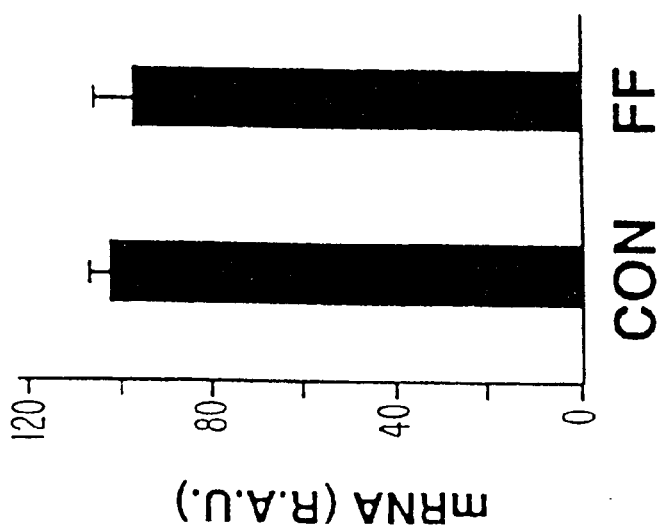
Figure 20C:
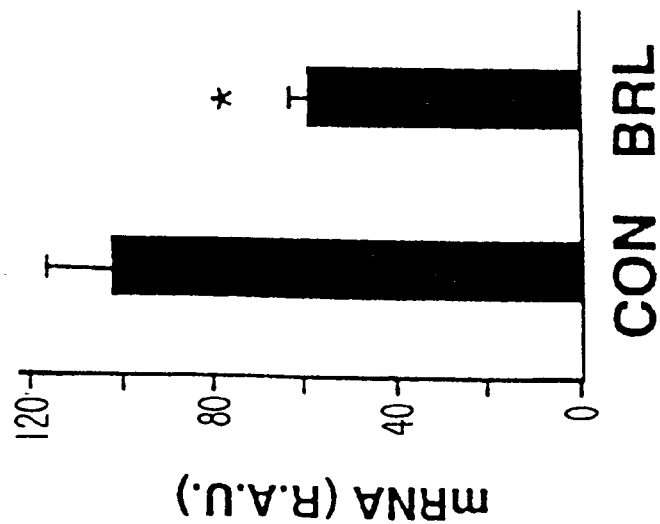

In this experiment, which used relatively low doses of BRL, food intake showed a tendency to decrease, although no statistical significance was obtained. When higher doses of BRL 49653 (5, 10, 20 mg/kg/day) were administered to rats over 7 days, a significant dose dependent increase in food intake was observed (FIG. 22).

ob mRNA levels in epidydimal fat pads of these rats decreased by 40% in rats treated with BRL 49653 (5 mg/kg/day) (FIG. 20). The effect of BRL 49653 on ob mRNA expression was furthermore dose-dependent (FIG. 23).

Figure 2:
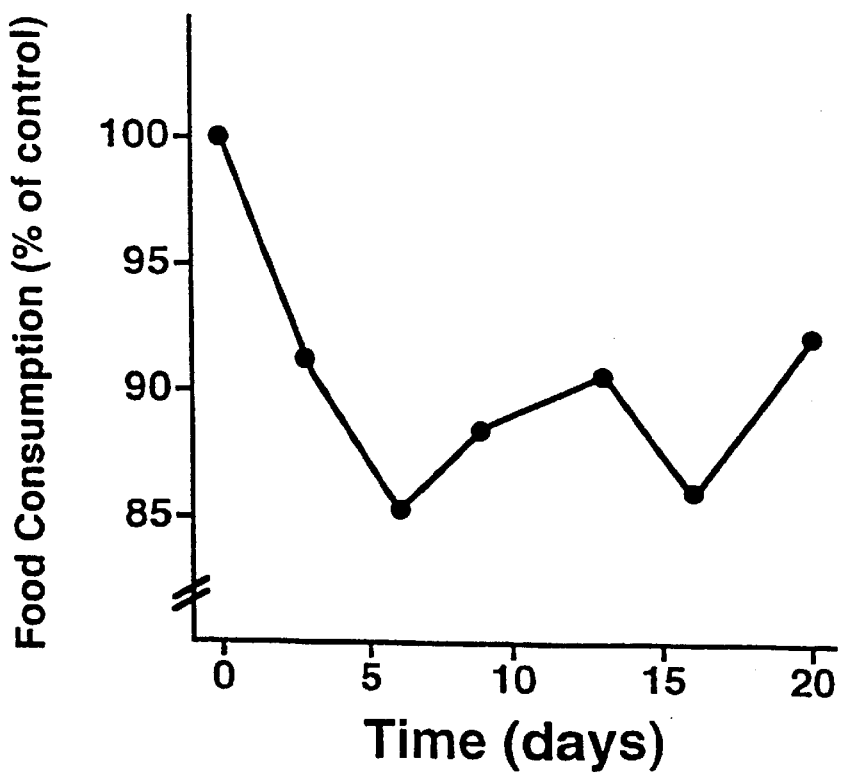
FIG. 2 is a graph which shows food consumption upon treatment with hydrocortisone. Adult male rats (n=4/group) were treated as described in FIG. 1. Total food consumption of each treatment group was measured at regular intervals and is expressed as a percentage of the food intake of a group of sham-treated controls.

Other potential conditions resulting in activation of PPARγ, such as administration of a diet enriched in fish oils (20% w/w in food, 3 months), also decreased ob mRNA expression significantly by 33% (FIG. 2). Therefore, fatty acid-derived PPAR activators are modulators of ob gene expression.

In contrast to the results obtained with thiazolidinediones and fish oils, administration of the PPARα activator, fenofibrate (0.5% w/w in food for 14 days ), did not result in a reduction of ob mRNA levels (FIG. 20). Treatment of animals with fenofibrate did not result in a change in body or adipose tissue weight, whereas the typical increase in liver weight (from 13.8±0.5 to 19.7±2.5 g) known to occur after treatment with peroxisome proliferators such as fenofibrate, was observed.

Ex vivo assay in primary adipocyte cultures

Primary rat adipocytes were obtained exactly as described by Hajduch et al. (1992) *J. Cell. Biochem.* 49:251–258. In order to determine whether the in vivo changes in ob gene expression are the result of a direct effect on adipocyte ob gene expression, the effects of BRL 49653 (100 μM; 24 hr) and the peroxisome proliferator, fenofibric acid (250 μM; 24hr), on ob mRNA expression were evaluated in primary rat adipocytes. Whereas BRL 49653 reduced ob mRNA expression significantly in three independent experiments, no effect of fenofibrate on ob mRNA levels was detected (FIG. 21A). These data confirm that the in vivo effects of the PPAR activators are due to a direct cellular effect on adipocyte ob gene expression.

In vitro in transfected cells

The effects of co-expression of PPARγ in the presence or absence of PPAR agonists on the human ob promoter construct pGL3-OB1 were examined.

In primary rat adipocytes, cotransfection of hamster PPARγ expression vector (pSG5-cgPPARγ) had minimal effect on basal activity observed in the absence of ligands or activators (FIG. 21B). Pioglitazone (PIO,10 μM) alone gave about 30% decrease in pGL3-OB1 expression, which further decreased to about 50% inhibition when PPARγ was cotransfected (FIG. 21B). When a more potent thiazolidinedione, such as BRL 49653 (10 μM), was used in rat primary adipocytes, the ob promoter activity was reduced to 40% and cotransfection of PPARγ had no further effect, suggesting the presence of saturating amounts of endogenous PPARγ in the mature adipocyte (FIG. 21B).

Treatment of the undifferentiated 3T3-L1 preadipocytes with thiazolidinediones by themselves had no effect on ob promoter activity in pGL3-OB1 because these cells, unlike primary adipocytes, do not contain PPARγ (Tontonoz, et al. (1994) *Cell* 79:1147–1156). Cotransfection of PPARγ in undifferentiated 3T3-L1 cells, however, reduced the activity of the pGL3-OB1 promoter construct. The degree of inhibition was dependent on the amount of PPARγ cotransfected. The addition of BRL 49653 had a slight cumulative effect.

In summary, the administration of the thiazolidinedione BRL49653, a PPARγ ligand, increased food intake and adipose tissue weight in rats while reducing ob mRNA levels in a dose-dependent manner. The inhibitory action of BRL49653 on ob mRNA levels was also observed in vitro. Thiazolidinediones (also including pioglitazone) reduced the expression of the human ob promoter in primary adipocytes. However, in undifferentiated 3T3-L1 preadipocytes lacking endogenous PPARγ, cotransfection of PPARγ was required to observe the decrease in ob mRNA. These data suggest that PPARγ activators reduce ob mRNA levels through an effect of PPARγ on the ob promoter.

The above assays have screened out PPARγ agonists, thiazolidinediones, BRL49653 and pioglitazone as modulators of an ob gene control region.

Other candidate compounds

The following compounds can be screened by the assays described and disclosed in this application for modulators of an ob gene control region:

1. Glucocorticoid Receptors

Compounds disclosed in Spiegelman et al., *J. Biol. Chem.* 264:1811–1815, (1989), Muglia et al., *Nature* 373:427–432, (1995) and Williams et al., *Mol Endocrinol.* 5:615–618 (1991) are incorporated by reference herein.

2. Thyroid Hormone Receptors ($T_3R$ family)

Thyroid hormones are known to have important effects on body weight homeostasis. On the one hand, in hyperthyroidism an increase in food intake has been observed, whereas in hypothyroidism food intake decreases significantly. Thyroid hormone is not only known to affect food intake but is also known to regulate basal metabolic rate (see chapters 9, 10, and 17 of Cryer et al., New Perspectives in adipose tissue: structure, function and development, London: Butterworths p. 474 (1985)) and adipose differentiation (Gharbi-Chibi et al., *Biochim. Biophys. Acta,* 1177:8014 (1993)). Due to this effect on basal metabolic rate one sees often a dissociation of the effects on body weight and food intake, suggesting that the effect on basal metabolic rate is the predominant one.

This was confirmed in a study analyzing the effects of thyroid hormone on body weight and food intake (Staels et al., *Endocrinology* 127:1144–1152 (1990)). Administration of thyroxine to make rats decrease in body weight despite an increase in food intake. Reduction of thyroid hormone levels by the administration of N-propyl-thiouracil results in a significant increase in body weight despite the fact that the animals ingest less food. These data show that thyroid function has a major impact on body weight. Therefore thyromimetics might be useful drugs for the treatment of obesity. Compounds disclosed in Underwood et al. *Nature* 324:425–429, 1986 are incorporated by reference herein. The thyromimetics disclosed in a European Patent Application entitled "Oxamic acid derivatives as hypocholesteremic agents" (Application Number 93810495.7, publication NO. 0580550A1, Jan. 26, 1994) are also incorporated by reference herein.

3. Peroxisome Proliferator Activated Receptors and their Agonists and Antagonists In contrast to the development of brown adipose tissue (BAT), which takes place mainly before birth, the development of WAT is the result of a continuous differentiation/development process throughout life (Lardy et al., *Annu. Rev. Biochem.* 59:689–710 (1990), Spiegelman et al., *J. Biol. Chem.* 268:6823–6826 (1993) and Aihauld et al., *TEM* 5:132–135 (1994)). During development, cells that are pluripotent become increasingly restricted to specific differentiation pathways. This process which culminates with differentiation into adult tissues undoubtedly involves a coordinate sequence of changes in gene expression reflected by the synthesis of increasingly specialized proteins.

Adipocyte differentiation from adipose precursor cells, or adipoblasts, has been shown to be orchestrated by two interdependently acting transcription factors: PPARγ (Tontonez et al., Genes & Development 8:1224–1234 (1994) and Tontonez et al., *Cell* 79:1147–1156 (1994)) and CCAATT enhancer binding protein α (C/EBP) (Christy et al., *Genes & Development* 3:1323–1335 (1989), Freytag et al., *Science* 256:379–382, (1992) and Freytag et al., *Genes & Development* 8:1654–1663 (1994)). Although both factors are capable of inducting terminal adipocyte differentiation, current evidence favors PPARγ as the initial trigger (Tontonez et al., *Cell* 79:1147–1156 (1994)).

In fact, expression of PPARγ occurs earlier than expression of C/EBPα during adipocyte differentiation. Furthermore, in contrast to C/EBPα, a transcription factor occurring in multiple tissues, PPARγ shows an adipose-restricted pattern of expression. Therefore the currently favored hypothesis suggests that PPARγ provides the initial trigger for the adipogenic program, whereas the terminal differentiation would require the concerted action of both PPARγ and C/EBPα.

At present 4 distinct peroxisome proliferator activated receptors (PPAR) have been described, i.e. α, β, γ, δ (Dreyer et al., Cell 68:879–887,(1992) and Kliewer et al., Proc. Natl. Acad. Sci. USA, 91:7355–7359 (1994)). PPARs are members of the superfamily of nuclear hormone receptors, which after ligand activation, regulate the expression of genes containing a specific response elements, called PPREs in their regulatory sequences (Osumi et al., *Biochem. Biophys. Res. Commun.* 175:866–871 (1991) and Tugwood et al., *EMBO J.* 11:433–439 (1992)). Functional PPREs have been characterized in several genes involved in the control of lipid metabolism (Osumi et al., *Biochem. Biophys. Res. Commun.* 175:866–871 (1991), Tugwood et al., EMBO J. 11:433–439 (1992), Zhang et al., *Proc. Natl. Acad. Sci. USA* 89:7541–7545 (1992), Marcus et al., *Proc. Natl. Acad. Sci. USA* 90:5723–5727 (1993), Alvarez et al., *Canc. Res.* 54:2303–2306 (1994), Bardot et al., *Biochem. Biophys. Res. Commun.* 192:37–45 (1993) and Tontonez et al., *Cell* 79:1147–1156 (1994)).

The transcriptional activity of the PPARs can be induced by various peroxisome proliferators (such as hypolipidemic fibrate drugs, plasticizers such as di-(2-ethylhexyl)-phtalate, or herbicides such as 2,4,5-trichlorophenoxyacetic acid) as well as by long chain fatty acids (Auwerx, *J. Hormone Research* 38:269–277 (1993)). This panoply of potential stimulators supports the current hypothesis that endogenous fatty acids are the true ligands for PPAR.

Whereas the endogenous ligands and activators of PPAR activity most likely are fatty acids, it is even more striking that most of the above mentioned PPAR target genes control various aspects in lipid metabolism. This points to a pivotal role of PPAR in the control of lipid metabolism and suggests that this factor might function as the key signaling molecule in many lipid and nutritionally controlled signalling pathways.

Coherent with this important role of PPAR in controlling lipid metabolism was the recent demonstration that one of the PPAR isoforms, PPARγ, was the key transcription factor triggering adipocyte differentiation (Tontonez et al., *Cell* 79:1147–1156 (1994)), and as such is involved in the direct transcriptional switch-on of several marker genes for adipocyte differentiation, including lipoprotein lipase and aP2 (Tontonez et. *Genes & Development* 8:1224–1234 (1994) and Tontonez et al., *Cell* 79:1147–1156 (1994)). The administration of PPARγ agonists resulted in a marked reduction of adipose tissue ob mRNA levels.

Genes with functional PPREs have been identified both in the LPL and the aP2 (Tontonez et al., *Genes & Develop.* 8:1224–1234 (1994) and Tontonez et al., *Cell,* 79:1147–1156 (1994)). This suggest that this nuclear hormone receptor is involved in differentiation pathways, a hypothesis supported by our recent studies on the lipoprotein lipase gene expression in the liver. The expression of LPL in the liver has been shown to be extinguished after birth, in a process very closely resembling the extinction of α-fetoprotein (Staels et al., *Development* 115:1035–1043 (1992)). Interestingly, administration of fibric acid derivatives or FFAs can reinduce the expression of LPL in the liver (Staels et al., *Development* 115:1035–1043 ((1992)), suggesting that the development role of PPAR is not limited to adipocytes.

Without being bound by any theory, Applicant proposes that ob gene may be silenced in tissues other than white fat cells. The silenced ob gene in a non-WAT cell may be turned on by an ob gene modulator to provide therapeutic effects.

FFA plays a role in adipose differentiation (Tontonez et al, 1994, *Genes & Development* 8:1224–1234, Tontonez et al., 1994, *Cell* 79:1147–1156, Amri et al., 1991, *J. Lipid Res.* 32:1449–1456 Amri et al., 1991, *J. Lipid Res.* 32:1457–1463, Chawla et al., 1994, *Proc. Natl. Acad. Sci. USA* 91:1786–1790 and Grimaldi, 1992, *Proc. Natl. Acad. Sci. USA* 89:10930–10934).

Fatty acids (Tontonoz, et al., (1994) *Cell* 79:1147–1156; Amri, et al., (1991) *J. Lipid Res.* 32:1449–1456; Chawla, A., and M. A. Lazar (1994) *Proc. Natl. Acad. Sci. USA* 91:1786–1790), arachidonic acid (Gaillard, et al., (1989) *Biochem. J.* 257:389–397), antidiabetic thiazolidinediones (Lehmann, et al., (1995) *J. Biol. Chem.* 270:12953–12956; Forman, et al., (1995) *Cell* 83:803–812), prostaglandin derivatives (Forman, et al., (1995) *Cell* 83:803–812; Kliewer, et al., (1995) *Cell* 83:813–819), and compounds disclosed in Tontonez et al., *Genes & Develop.* 8:1224–1234 (1994), Amri et al., *J. Lipid Res.* 32:1457–1463, and Grimaldi et al., *Proc. Natl. Acad. Sci. USA* 89:10930–10934 (1992) are incorporated by reference herein.

In addition to PPARγ, other PPAR subtypes such as PPARβ (also called FAAR, NUC1, or PPARδ) and PPARα play roles in adipocyte differentiation.

PPARβ is expressed in preadipocyte at an earlier stage than PPARγ, suggesting that it has function in adipocyte differentiation. Agonists and antagonists of PPARβ or agents affecting the expression of PPARβ may have effects on ob gene expression.

Mice deficient in PPARα (e.g. generated by homologous recombination) develop a pronounced obesity as they age. PPARα agonist are therefore potential agents decreasing adipocytogenesis and reducing obesity whereas PPARα antagonists are potential agents increasing adipocyte differentiation and increasing appetite, food intake, body fat content, or body weight.

Agonists and antagonists of PPARβ and PPARα are candidate compounds for the assays of this invention and modulation of ob gene expression.

4. Retinoic Acid Receptors and Retinoid X Receptors (RAR and RXR Families)

Retinoic acid is known to inhibit adipogenesis in 3T3-F442A and ob 17 cells. Compounds disclosed in Antras et al., J. Biol. Chem. 266:1157–1161 (1991), Salazar-Olivo et al., Biochem. Biophys. Res. Commun. 204:157–263 (1994) and Safanova, Mol. Cell. Endocrin. 104:201–211 (1994) are incorporated by reference herein.

5. Estrogen Receptors (ER Family)

Estrogens are known to have important effects on body weight and food intake. An experiment performed on female rats was published by Staels et al., J. Lipid Res. 30:1137–1145 (1989). Both ovariectomy (OVX) and consecutive substitution therapy, with the indicated doses of ethinylestradiol, showed a marked effect on body weight in ovariectomized rats.

This effect was not specific for female rats since changes in body weight and food intake was observed in male mice injected with ethinylestradiol. Whereas sham-injected male mice showed an increase in body weight of 1.81±1.04%, their ethinyl estradiol (0.75 μg/g body weight) injected littermates showed a 14.83±1.44% decrease in body weight over a 7 day treatment period. The decrease in body weight was associated with an important reduction in food intake.

In order to prove that the decrease in food intake caused by EE was responsible for the change in body weight, we compared body weight between ovariectomized rats and control rats, between ovariectomized rats and ovariectomized rats substituted with 20 μg ethylestradiol (EE) per day, and between ovariectomized rats and ovariectomized rats substituted with 2000 μg ethinylestradiol per day, who this time had been pair-fed (Staels et al., J. Lipid Res. 30:1137–1145 (1989)). Either the intact animals or the animals which received estrogens were taken as reference in the pair feeding. Interestingly, pair-feeding abolished the effects of estrogens on body weight, suggesting that estrogens exert their effect on body weight by reducing food intake.

6. Androgen Receptors (AR Family)
7. Progesterone Receptors (PR a and b)
8. Mineralocortinoid Receptors (MR Family)
9. Insulin and Insulin Receptors Including Secretagogue
10. Helix-Loop-Helix (HLH) Transcription Factors Such as SREBP-like Factors and ADD1

The compounds disclosed in Tontonez et al., Mol. Cell. Biol. 13:4753–4759 (1993) are incorporated by reference herein.

11. CAAT/Enhancer Binding Proteins (C/EBP)

C/EBP family members may be responsible for regulating ob as adipocytes undergo differentiation. It has been shown that expression of members of the C/EBP family can be modulated by extracellular compounds such as stimulators of the cAMP pathway and glucocorticoids. For example, two lines of evidence have shown that C/EBP α is involved in the differentiation of adipocytes. 1) Over expression of C/EBP α induces differentiation. 2) Antisense oligonucleotides to C/EBP α inhibit the differentiation of adipocytes. C/EBP family members have been shown to be regulated in mature adipocytes by insulin. Furthermore, many adipocyte-specific genes involved in differentiation contain C/EBP sites.

12. AP-1 Like Factors Including Protein Kinase C and Protein Kinase A

13. Growth Hormones and Their Agonists and Antagonists

Those disclosed in Corin et al., Proc. Natl. Acad. Sci. USA 87:7507–7511 (1990), Uchida et al., Biophys. Res. Commun. 172:357–363 (1990) and Barcellini-Couget et al., Biochem. Biophys. Res. Commun. 199:136–143 (1994) are incorporated by reference herein 14. Tumor Necrosis Factor (TNF) and Related Compounds TNF inhibits the expression of several adipocyte specific genes. This ultimately will result in a loss of differentiated adipose tissue (Kawakami et al., J. Cell. Physiol. 138:1–7 (1989)) and the occurrence of cachexia. It has been recently shown that adipocytes of animals suffering from obesity showed an increased production of TNF (Hotamisligil et al., Science 259:87–91, 1993). The TNF was furthermore linked to the occurrence of insulin-resistance a phenomenon often associated with obesity (Hotamisligil et al., Science 259:87–91 (1993)).

Without being bound by any theory, it is hypothesized that in normal weight subject TNF is involved in a physiologic feedback loop limiting the development of obesity. In obese animals this feedback process might be disturbed, resulting in a compensatory overproduction of TNF and the development of insulin resistance.

One of the most debilitating effects of cancer and AIDS is the wasting syndrome known as cachexia which often accompanies these conditions. Cachexia is a combination of anorexia, reduced intake of nutrients, and stimulation of catabolic processes leading to protein loss and depletion of lipid reserves. The cytokine tumor necrosis factor (TNF) is often elevated in the plasma of individuals displaying cachexia and was originally termed cachectin as a result of its association with cachexia. Administration of recombinant TNF to animals replicates the effects of cachexia in animals, and administration of anti-TNF antibodies can in some cases alleviate the effects of cachexia.

A target for therapeutic treatment of cachexia would be to block the production of TNF or TNF signal transduction which may play a role in the ob gene expression. The drug pentoxifylline has been tested in cancer patients for the reduction of cachexia and was found to improve the conditions of some patients. Monoclonal antibodies to TNF and soluble TNF (and/or ob gene product mediated) induced cachexia would be of utility in the treatment of wasting associated with chronic conditions such as cancer and AIDS.

Another strategy for therapeutic treatment of cachexia is to down regulate ob gene expression. Without being bound by any theory, applicant proposes that TNF and ob gene act synergistically to affect food intake. Inhibitors of TNF and inhibitors of ob production may act synergistically to relieve cachexia.

15. Cytokines and Growth Factor Such as IL1 and TGF-β

The compounds disclosed and referred to in Gimble et al., Mol. Cell. Biol. 57:4587–4595 (1989) are incorporated by reference herein.

16. Insulin

Insulin levels in blood are increased postprandially, whereas lower insulin levels are found during the interprandial periods. We have preliminary evidence showing that the induction in ob mRNA levels detected after food ingestion in rats relative to fasted animals can be ascribed to higher insulin levels in fed rats. Therefore, insulin administration or elevation of endogenous insulin via the administration of insulin secretagogues could induce ob mRNA levels and increase circulating ob levels. This would be translated into a decrease in food intake.

Candidate compounds include insulin mimetics (Ibrahimi et al., 1994 *Mol. Pharmacology* 46:1070–1076) and secretagogues, amino acids, free fatty acids, carbohydrates, sulfonamides, biguanides (antidiabetics), metformin, phenformin, pyroglyrides, thiazolidinediones and their antagonists.

17. Adrenergic System

Antagonists might be helpful since adrenergic stimulation promotes preadipocyte proliferation (Bouloumie et al., J. Biol. Chem. 269:30254–30259 (1994)). In contrast, α-antagonist, phenoxybenzamide, prevents weight gain and fat accumulation. β3-agonists and antagonists (e.g., ICI compounds D7–114, D2079) which stimulate development of brown adipose tissue are candidate compounds too.

The compounds disclosed and referred to in Lowell et al., *Endocrinology* 126:1514–1520 (1990) are incorporated by reference herein.

18. Glucocorticoids, Precursors and Derivatives (Antagonists)
19. Thyroid Hormone and Thyromimetics
20. Fibrates, Antagonists, Subtype Selective Compounds Clofibric acid, fenofibrate, etiofibrate, gemfibrozil and the thiazolidinedione antidiabetic compounds (Ibrahimi et al., *Mol. Pharmacol.* 46:1070–1076 (1994)) are all known to stimulate transcriptional activity of the PPAR nuclear hormone receptors. Inhibitors of PPAR activity are useful as well.

21. RAR-selective Agonists and Antagonists

The compounds disclosed and referred to in (Antras et al., *J. Biol. Chem.* 266:1157–1161 (1991)) are incorporated by reference herein.

22. RXR-selective Agonists and Antagonists
23. Estrogens, Agonists, Partial Agonists, Partial Antagonists and Antagonists
24. Androgens, Agonists, Partial Agonists, Partial Antagonists and Antagonists
25. Progestins, Agonists, Partial Agonists, Partial Antagonists and Antagonists
26. Mineralocorticoids, Agonists, Partial Agonists, Partial Antagonists and Antagonists
27. Insulin
28. Fatty Acids and Sugars
29. Non-steroidal Anti-inflammatory Drugs (NSAIDS): Prostacylins The compounds disclosed and referred to in Knight et al., *Mol. Endocrinol.* 1:36–43 (1987) and Negrel et al., *Biochem. J.* 257:399–405 (1989) are incorporated by reference herein.

30. Dihydroepiandosterone (DHEA), its Precursors and Derivatives

DHEA has been known for some time to reduce body weight (for review see Cleary, *Proc. Soc. Exp. Biol. Med.* 196 (1991)). Recently a number of more specific compounds, with a greater effect in reducing body weight and less potential harmful side effects have been developed (Schwartz et al., *Canc. Res.* 48:4817–4822 (1988)). In a short experiment performed in rats, applicant determined that DHEA was capable of reducing the gain in body weight already after a three day treatment period. The reduction in body weight was associated with a significant decrease in food intake.

Furthermore, independent on its effects on food intake DHEA has also important effects on adipocyte differentiation (Shantz et al., *Proc. Natl. Acad. Sci. USA* 86:3582–3856 (1989)).

31. TNF, Cytokines, and Related Molecules
32. Fetuin

The compounds disclosed and referred to in Gaillard et al., *Biochim. Biophys. Acta* 846:185–191 (1985) are incorporated by reference herein.

33. Amylin Antagonists and Agonists
34. Prolactin
35. Niacin, Acepimox and Other Nicotinic Acid Derivatives These compounds are antilipolytic.

36. Triacsins

The compounds disclosed and referred to in (Tomoda et al., *J. Biol. Chem.* 266:4214–4219 (1991); inhibitors of ACS) are incorporated by reference herein.

37. Amphetamine and Derivatives (Including Fenfluramine and Dexfenfluramine)
38. Endorphin Antagonists
39. Somatostatin
40. Cholecystokinin (CCK)
41. Bombesin
42. Gastrin
43. Oral Antidiabetic Agents and Antagonists The compounds disclosed and referred to in Sparks et al., *J. Cell. Physiol.* 146:101–109 (1991) and Hirugan et al., *J. Cell. Physiol.* 134:124–130 (1988) (AD4743) are incorporated by reference herein.

Thiazolidinedione antidiabetic compounds (see under fibrates), competitors, agonists, antagonists, homologs, structural analogs thereof and compounds antagonizing thiazolidinedione's action: These compounds strongly activate PPARs. (Ibrahimi et al., *Mol. Pharmacol.* 126:1514–1520 (1990)).

The compounds disclosed and referred to in Fong et al., *Biochem. Biophys. Res. Commun.* 181:1385–1391 (1991) (tolbutamide) are incorporated by reference herein.

Antidiabetics reviewed by Colca and Morton In *New Antidiabetic Drugs;* Bailey, C. J., Flatt, P. R., Eds.; Smith-Gordon; 1990 and Stevenson, et al. In *Diabetes Annual;* Marshall, S., Home, P., Rizza,, R., Eds.; Elsevier Science: Amsterdam, 1995; Vol. 9, p 175 are incorporated by reference herein.

Exemplary thiazolidinedione candidate compounds include Troglitazone (CS-045) (Yoshioka, et al. *J. Med. Chem.* 32:421, 1989; Fujiwara, et al. *Diabetes* 37:1549, 1988); Pioglitazone (AD-4833) (Meguro, et al. U.S. Pat. No. 4,687,777, 1987); Ciglitazone (ADD-3878) and analogs (e.g. WAY-120, 744) (Sohda, et al. *Chem. Pharm. Bull.* 30:3563, 1982; Ellingboe, et al. *J. Med. Chem.* 36:2485, 1993); BRL 49653 and analogs (Cantello, et al. *J. Med. Chem.* 27:3977, 1994; Young, et al. *Diabetologia* 36(Suppl. 1):A75, 1993); Englitazone (Hargrove, et al. In *Frontiers in Diabetes Research;* E, S., Ed.; Smith-Gordon and Co Ltd: U.K., 1990; Vol. 7, p 313 and references therein); AD 5075 (Williams, et al. *Diabetes* 42 (Suppl. 1):52A, 1993 and references therein); and Darglitazone (CP-86325) (Hulin, et al. *J. Med. Chem.* 35:1853, 1992).

Other related antidiabetic agents to be screened include Oxazolidinediones and oxadiazolidinediones (Dow, et al. *J. Med. Chem.* 34:1538, 1991; Goldstein, et al. *J. Med. Chem.* 36:2238, 1993); 5-benzyltetrazoles, (Kees, et al. *J. Med. Chem.* 35:944, 1992); Hydroxyureas (Goldstein, et al. *J. Med. Chem.* 36:2238, 1993); and Ciglitazone-like Carboxylic acid derivatives or analogs.

44. CRH

Hypothalamic administration of corticotropin-releasing hormone into fat rats reduces body weight (Rohner-Jeanrenaud et al., *Endocrinology* 124:733–739 (1989)). The exact mechanism for this effect is actually unknown. It has been suggested that CRII affects the sympathetic output from the hypothalamus.

45. Adrenocorticotropic Hormones, ACTH a and b MSH

The lethal yellow mutation in mouse, which is associated with an overexpression of the agouti gene product is characterized amongst others by the development of massive obesity and diabetes (Bultman et al., *Cell* 71:1195–1204 (1992)). It has been shown that the mouse agouti gene interacts with the product of the extension gene (which encodes the melanocyte receptor for alpha-melanocyte stimulating hormone α-MSH) (Lu et al., *Nature* 371:799–802 (1994)). MSH agonists or antagonists may have an effect on the development of obesity.

46. Gastric Inhibitory Peptides (GIP)

The compounds disclosed and referred to in Eckel et al., *Diabetes* 28:1141–1142 (1979) are incorporated by reference herein.

47. Compounds Acting Through Insulin-like Growth Factor (IGF)

III. Treating Diseases with a Modulator of ob Gene Expression ob gene is a target for therapeutic intervention of metabolic disorders and related pathological conditions White adipose tissue (WAT) is composed of adipocytes, which play a central role in lipid homeostasis and the maintenance of energy balance in vertebrates. These cells store energy in the form of triglycerides during periods of nutritional affluence and release it in the form of free fatty acids (FFA) at times of nutritional deprivation. An excess of WAT leads to obesity whereas absence of WAT is associated with lipodystrophic syndromes. In man, obesity is an independent risk factor for several diseases including NIDDM (non-insulin-dependent-diabetes-mellitus), hypertension, infertility and coronary artery disease. An important gene involved in the pathogenesis of obesity is the product of the human homologue of the murine obese gene (i.e., ob gene). This gene has been identified by positional cloning in the ob/ob mouse (Zhang et al., *Nature* 372:425–432, 1994). The obese mutation in mice is one of five recessive mutations, which give rise to a profound obesity and NIDDM (Friedman et al, *Genomics* 11:1054–1062, 1991), similar to conditions in humans with morbid obesity. Cross-circulation experiments between mutant and wild-type mice suggest that ob mice are deficient for a blood-borne factor that regulates nutrient intake and metabolism (Coleman, *Diabetologia* 14:141–148, 1978). This blood-borne factor is considered by some to be identical to the 18 kDa protein synthesized from the ob gene.

The ob sequence is highly conserved between mouse and man, suggesting an important regulatory function. Its expression is restricted to WAT, suggesting that the ob protein, leptin, is a fat-derived satiety factor (Zhang et al., *Nature* 372:425–432, 1994). ob mice either have a nonsense mutation resulting in the production of a truncated and non-functional mRNA (C57B16J ob/ob) or carry a genomic alteration resulting in the absence of mRNA (SM/Ckc-+ $^{Dac}$ob$^{2J}$/ob$^{2J}$) (Zhang et al., *Nature* 372:425–432, 1994).

The fact that the ob mRNA level in adipose tissue of the C57B16J ob/ob mice is greatly increased suggests that the level of expression of this gene signals the size of the adipose depot. An increase in the ob signal (as might occur after prolonged eating) may act directly on the central nervous system (CNS) to inhibit food intake and/or regulate energy expenditure as part of a homeostatic mechanism to maintain constancy of adipose tissue mass, etc. The level of ob expression is inversely correlated with food intake, energy expenditure and the onset of obesity. This invention pertains to using modulators of ob gene expression to change the level of ob gene expression product (i.e. leptin), which in turn changes the homeostatic status of a host to achieve therapeutic purposes.

EXAMPLE 2

Reducing Body Weight Gain with Hormones that Stimulate ob Gene Expression

Applicant studied the effects of high doses of glucocorticoids on the expression of the ob gene and changes in body weight and food intake.

Rat was chosen as a model because its body weight and adipose tissue mass keeps increasing throughout its entire life-span, thereby resembling the human situation of adult onset obesity.

Figure 4A:
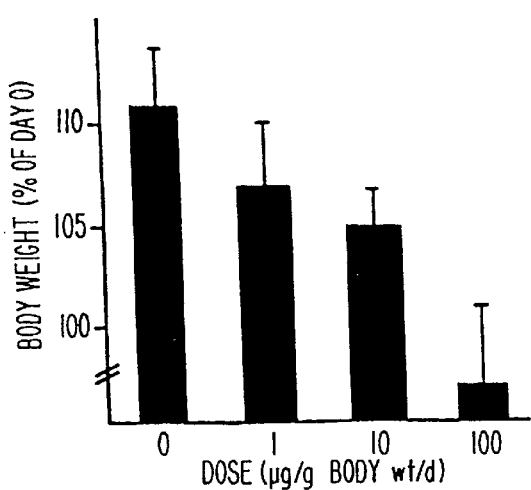
FIGS. 4A–B is a graph which shows body weight gain (A) an adipose tissue's ob mRNA levels (B). Adult male rats (n=4 animals/group) received once-daily subcutaneous injections of hydrocortisone at the indicated doses for 20 days. Control animals received saline only.
Figure 4B:
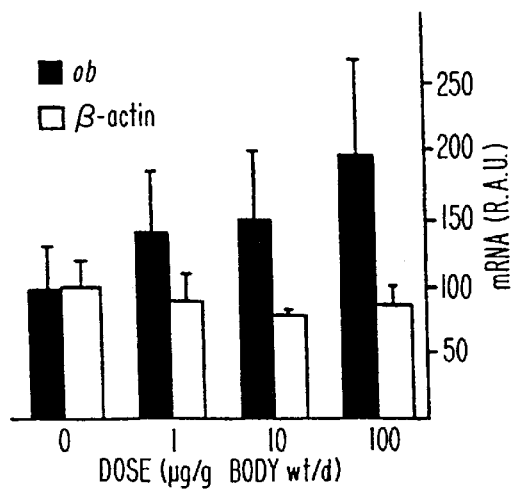

Corticosteroids (such as hydrocortisone) are known to exert dual metabolic actions, reflected by a bitonic dose-response curve for body weight gain (Devenport et al. *Life Science* 4S:1389–1396, 1989). In order to evaluate the dose-dependent effects of hydrocortisone on body weight and ob gene expression, adult rats were treated once daily during 20 days with 3 different doses of hydrocortisone (1, 10 or 100 µg/g body weight), resulting in a dose-dependent reduction in body weight gain (FIG. 4A) accompanied by a dose-dependent induction of ob mRNA levels in adipose tissue (FIG. 4B).

The results demonstrate that administration of pharmacological doses of glucocorticoids induces adipose tissue ob gene expression. This induction is accompanied by reduced food intake and decreased body weight gain in these animals. These data indicate that modification of ob gene expression is subject to hormonal/pharmacological regulation, leading to the modulation of caloric intake and body mass gain.

Figure 1:
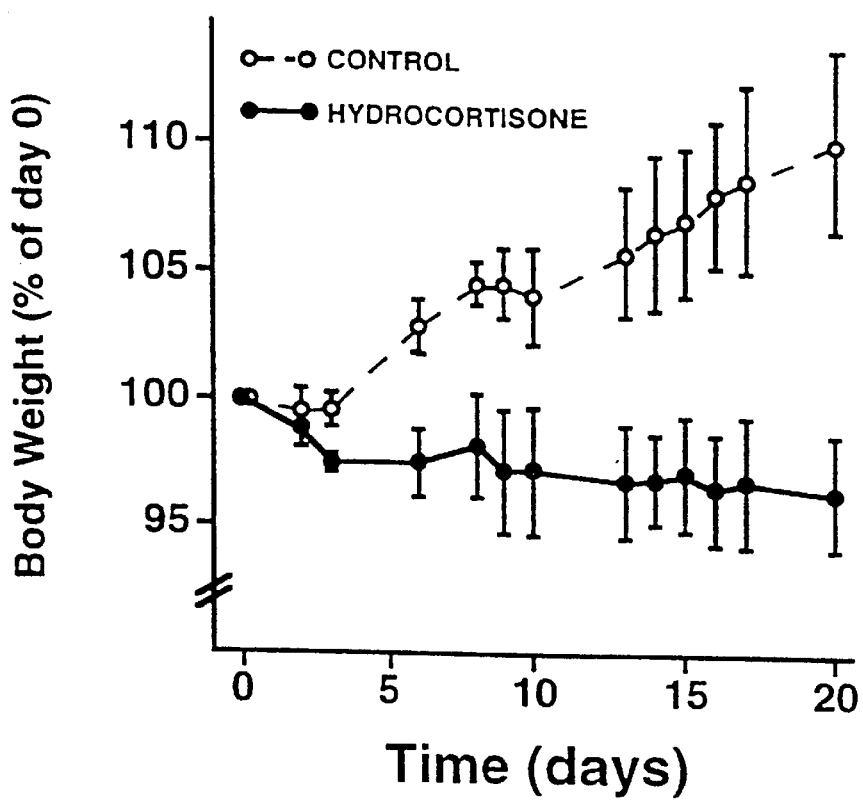
FIG. 1 is a graph which shows body weights of rats upon treatment with hydrocortisone. Adult male rats received once-daily subcutaneous injections of hydrocortisone (100 μg/g body weight) for the indicated number of days. Control animals received saline only. Body weights were recorded at regular intervals and are expressed as a percentage of pretreatment (day 0) body weight. Values represent the mean +/−SD of 4 animals/group.

A. Glucocorticoid Decreases Body Weight Gain and Food Intake 80-day-old male rats were treated once daily during 20 days with 100 µg/g body weight of hydrocortisone. Sham-treated control rats exhibited a significant, steady gain in body weight throughout the treatment period, attaining approximately 110% of the initial body weight after 20 days (FIG. 1). Administration of hydrocortisone, however, completely prevented this gain in body weight, and resulted in a slight decrease in body weight at the end of the treatment period (FIG. 1).

This difference in body weight gain between control and treated animals became only gradually apparent. During the first 2 days of treatment, body weights did not differ significantly from controls and only thereafter a gradually more pronounced difference was observed.

Compared to untreated animals, hydrocortisone-injected animals consumed 10–15% less food throughout the entire treatment period (FIG. 2), indicating that a reduction of food intake may, at least in part, account for the lower gain in body weight after hydrocortisone treatment.

B. Glucocorticoid Increases ob Gene Expression in vivo

Figure 3:
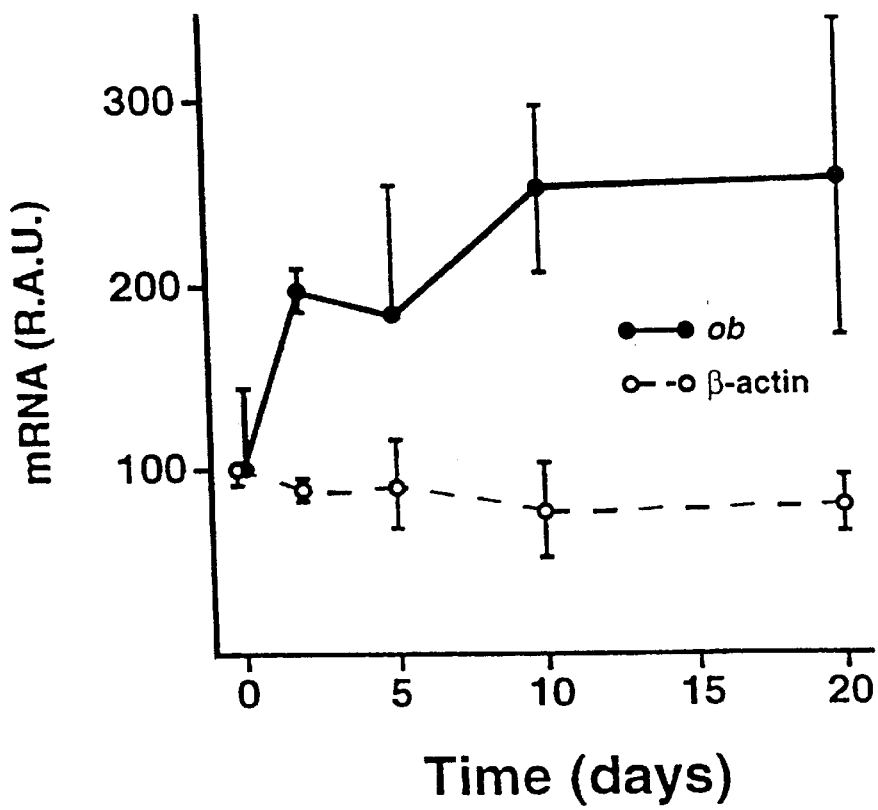
FIG. 3 is a graph which shows ob mRNA level in adipose tissue with treatment with hydrocortisone. Adult male rats (n=4/group) were treated as described in FIG. 1. Adipose tissue was isolated, RNA was extracted and ob and β-actin mRNA levels were measured as described below. Values represent the mean +/−SD of 4 animals and are expressed in relative absorbance units (R.A.U.) taking the pre-treatment values as 100%.

The regulation of adipose tissue ob mRNA expression by hydrocortisone was determined next. Treatment with hydrocortisone increased ob mRNA levels more than 2-fold, and the effect which was maximal after 2 days (FIG. 3). ob mRNA levels remained elevated throughout the entire treatment period. This induction was specific because β-actin mRNA levels remained constant throughout the entire treatment period (FIG. 3).

The effects of the synthetic glucocorticoids, dexamethasone and triamcinolone, which are relatively pure type II corticosteroid receptor agonists and produce a more pronounced monotonic negative dose-response curve of body weight gain (Devenport et al. Life Science 45:1389–1396, 1989), were analyzed and compared to hydrocortisone.

Treatment of adult male rats during 4 days with triamcinolone or dexamethasone also resulted in reduced food consumption (FIG. 5A) with concomitant increase of ob mRNA levels (FIG. 5B).

Northern blot hybridization analysis indicated that the ob cDNA probe hybridized to an mRNA of approximately 4.5 kb, a size similar to mouse adipose tissue ob mRNA (Zhang et al., Nature 372:425–432, 1994). Furthermore, ob mRNA levels increased 2.2-fold in rat adipose tissue within 24 hr after a single injection of dexamethasone, indicating that the induction of ob gene expression by corticosteroids is a very rapid event.

These results demonstrate that glucocorticoids induce ob expression in rat adipose tissue with concomitant gain in body weight and food intake decrease.

Several lines of evidence support a causal relationship between the induction of ob gene expression and a decrease in food intake and body weight.

First, the induction of ob gene expression is very rapid and nearly maximal within 24 hr after a single injection of corticosteroids. By contrast, the changes in body weight follow much more gradually, the difference with sham-treated controls only becoming significant after 3 days of treatment. Taking into account that a 16-hour overnight fast reduces the body weight of rats by approximately 7.5% (fed: 376+/−12; fasted: 350+/−10 grams), it appears that the effects of corticosteroids on body weight changes are much more gradual and lag behind the induction of ob gene expression.

Second, the induction of ob expression by corticosteroids is independent of food intake, since it is observed regardless whether animals are fed or fasted.

Third, it is unlikely that the alterations in ob expression are secondary to the decrease in food intake and body weight, since ob mRNA levels are increased in hyperphagic C57B16J ob/ob mice, which have apparently normal regulation of the ob gene.

Finally, in contrast to normal mice, genetically obese ob/ob mice are dramatically resistant to glucocorticoid-induced weight loss (McGinnis et al., Life Sciences 40:1561–1570, 1987), indicating that the presence of a functional ob gene product is required to transmit the glucocorticoid-induced weight loss.

Therefore, the induction of ob expression after corticosteroid treatment precedes and probably provokes the ob gene related alterations in food intake and body weight.

In this respect it is interesting to note that plasma corticosteroid levels are elevated in obese C57B16J ob/ob mice (Dubuc, Hormone and Metabolism Research 9:95–97, 1976; Herberg et al., Hormone and Metabolism Research 7:410–415, 1975; and Naeser, Diabetologia 10:449–453, 1974), which may, at least in part, explain the increase in ob mRNA levels observed in these mice (Zhang et al., Nature 372:425–432, 1994).

Depending on the dose used, corticosteroids seem to exert a dual metabolic action on gain in body weight and feeding efficiency (Devenport et al. Life Science 45:1389–1396, 1989). Administration of high doses of glucocorticoids, such as in this study, results in a marked decrease in food intake and body weight. In contrast, lower doses of corticosteroids have anabolic activity marked by increased appetite in humans and stimulation of food intake in laboratory animals.

However, in contrast to their catabolic effects, it is unlikely that the anabolic effects of glucocorticoids at low doses are mediated through changes in ob gene expression. Indeed, although ob/ob mice do not express a functional ob gene product, adrenalectomy reduces food intake and normalizes energy balance (Solomon et al., Endocrinology 93:510–513, 1973; Solomon et al., Hormone and Metabolism Research 9:152–156, 1977; and Yukimura et al., Proc. Soc. Exp. Biol. Med. 159:364–367, 1978), whereas corticosteroid replacement therapy restores food intake in these adrenalectomized ob/ob mice (Saito et al., American Journal of Physiology 246:R20–25, 1984).

The effects of corticosteroids on ob gene expression may be due to a direct or indirect action of these hormones on ob gene transcription. High doses of glucocorticoids may, for instance, influence the plasma concentrations of other hormones which regulate food intake, such as Dihydroepiandosterone (DHEA). Glucocorticoids may act by altering plasma concentrations of a modulator of gluconeogenesis, which in turn induces ob gene expression resulting in a reduction of food consumption. In this case, factors involved in glucose metabolism, such as glucose itself, glucagon and insulin, would be expected to be important modulators of ob gene expression. Low doses (anabolic) of glucocorticoids may produce similar but opposite effects in this metabolic pathway leading to reduced ob gene expression and a corresponding increase in food consumption.

Glucocorticoids may also exert their therapeutic effects by binding to a superfamily of intracellular receptors (IRs), which are regulators of gene transcription. The classical mechanism of transcriptional regulation by IRs involves binding of the IRs to specific response elements in the promoters of the regulated genes, for example, the binding of the estrogen receptor to its response site in the vitellogenin gene (Klein-Hitpass et al., Cell 46:1053–1061, 1986). More recently a different mechanism of IRs function has been described in glucocorticoid receptor mediated AP-1 transcription regulation that does not require direct DNA-binding of the IRs (Yang-Yen et al., Cell 62:1205–1215, 1990).

Materials and Methods

Animals and Treatments

Eighty-day-old male rats received once-daily subcutaneous injections with the indicated corticosteroids at a dose and for the period of time indicated. Control animals received saline only. Rats were group-housed and accustomed to a 12:12 hr day-night illumination cycle. Animals were allowed free access to standard rat chow. Body weight (per animal) and food consumption (per treatment group) were measured at regular intervals throughout the experiment. At the end of the experiment, animals were killed between 9–10 AM by exsanguination while under ether anesthesia. Epididymal fat pads were removed immediately and frozen in liquid $N_2$.

RNA Analysis

Total cellular RNA was prepared by the acid guanidinium thiocyanate/phenolchloroform method (Choeczynski, et al., Analytical Biochemistry 162:156–159, 1987). Northern and dot blot hybridizations of total cellular RNA were performed as described previously (Staels, et al., Development 115:1035–1043, 1992). A mouse ob cDNA fragment spanning nucleotides +50 to +659 was cloned from adipose tissue by reverse transcription and PCR-amplification (sense primer: 5'CCA AGA AGA GGG ATC CCT GCT CCA GCA GC-3' (SEQ ID NO:35); antisense primer: 5° CCC TCT ACA TGA TTC TTG GGT ACC TGG CC-3' (SEQ ID NO:36) (Zhang et al., *Nature* 372:425–432, 1994). a β-actin cDNA clone was used as a control probe (Cleveland, et al., *Cell* 20:95–105, 1980). All probes were labeled by random primers (Boehringer Mannheim). Filters were hybridized to $1.5 \times 10^6$ cpm/ml of each probe as described (Staels, et al., *Development* 115:1035–1043, 1992). They were washed once in 0.5× SSC and 0.1% SDS for 10' at room temperature and twice for 30' at 65° C. and subsequently exposed to X-ray film (X-OMAT-AR, Kodak). Autoradiograms were analyzed by quantitative scanning densitometry (Biorad GS670 Densitometer) as described (Staels, et al., *Development* 115:1035–1043, 1992).

C. Feeding and Insulin Treatment Up Regulate ob Gene Expression in vivo

The effects of feeding and insulin on ob gene expression in rats was studied by Applicant. The results demonstrate that in fasting rats the ob gene expression is upregulated by insulin administration or feeding to a similar extent.

Adult male Sprague-Dawley rats were group-housed and acclimated to a 12hr:12hr day:night illumination cycle (light from 6 A.M. to 6 P.M.). To determine the diurnal variation of ob gene expression, rats (n=4 per experimental group) were sacrificed at regular intervals (4 hrs) throughout a period of 24 hrs.

To study the role of acute food consumption and insulin treatment, rats were divided into 5 groups (n=3 per experimental group). A first group was allowed free access to food and served as a fed control. All other groups were denied access to food during a 12 hr overnight period (the dark cycle). At the beginning of the light cycle, 3 groups of fasted animals received either free access to food, a single injection with insulin (1 U; Actrapid HMge, Novo Nordisk), or both. The last group of fasted animals served as a fasting control. Food consumption was monitored throughout the experiment. All animals were sacrificed four hours after insulin administration and/or access to food by exsanguination under ether anesthesia. Epididymal adipose tissue was removed, rinsed with 0.9% NaCl and frozen in liquid nitrogen.

RNA isolation, analysis of ob gene expression by Northern hybridization, and quantitation were performed as described above.

As shown in FIG. 7, fasted rats that received a single dose of insulin showed about 50–60% increase in adipose tissue ob gene expression relative to fasted rats. Fasted rats that received food showed similar increase relative to the fasted controls.

Since feeding stimulates increases in plasma insulin levels, it was tested to determine if insulin is a mediator of the up regulation of ob gene expression seen in fed animals. As shown in FIG. 11, overnight fasting decreased ob mRNA levels to a basal level normalized to 100 relative absorbance units (R.A.U.). A single subcutaneous injection of 1 I.U. insulin resulted in an approximately two-fold increase in ob mRNA 4 hours post injection relative to actin controls as measured by Northern analysis. This is a comparable increase to refeeding after an overnight fast. Refeeding plus insulin gave no additive effects on ob mRNA level. Plasma glucose levels confirmed the effects of administration of insulin and the fed state.

FIG. 12 shows the effect of insulin on ob mRNA under hyper- or eu-glycemic clamps. The stimulatory effect of insulin on ob mRNA was maintained when plasma glucose levels were maintained at either high or low levels.

Insulin also affects ob mRNA expression in primary rat adipocytes. Primary rat adipocytes were cultured in media containing 10% Fetal Bovine Serum (FBS) and treated with either 1 or 10 nM insulin added to the medium. As shown in FIG. 13, insulin stimulated the production of ob mRNA in a dose dependent manner.

A similar result is obtained when the ob promoter driven luciferase vector pGL3B-OB1 is introduced into the primary adipocytes. A 140% increase of the level of ob mRNA in media containing 10% FBS is observed upon the addition of 200 nM insulin. Since fetal bovine serum contains insulin which could affect the basal level of expression, the experiment is repeated with a reduced level of FBS to more precisely measure the effects of insulin in this system.

EXAMPLE 3

Treating Diseases with a Down Reagulator of an ob Gene

Cachexia is a combination of anorexia, reduced intake of nutrients, and stimulation of catabolic processes leading to protein loss and depletion of lipid reserves.

As shown in Example 1, administration of the thiazolidinedione compound BRL49653, a PPARγ agonist, increased food intake and adipose tissue weight while reducing ob mRNA levels in rats in a dose-dependent manner. BRL49653 was also observed in vitro to reduce the activity of the human ob promoter in primary adipocytes. In undifferentiated 3T3-L1 preadipocytes lacking endogenous PPARγ, cotransfection of PPARγ was required to observe the decrease. In conclusion, these data suggest that a down regulator of an ob gene, e.g. a PPARγ agonist such as a thiazolidinedione compound, is capable of increasing food intake and body weight, and thus treating cachexia, anorexia and other wasting diseases.

IV. Pharmaceutical Formulations and Modes of Administration

The particular compound that affects the disorders or conditions of interest can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

The compounds also can be prepared as pharmaceutically acceptable salts. Examples of pharmaceutically acceptable salts include acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See e.g., PCT/US92/03736). Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents.

In addition, the molecules tested can be used to determine the structural features that enable them to act on the ob gene control region, and thus to select molecules useful in this invention. Those skilled in the art will know how to design drugs from lead molecules, using techniques such as those disclosed in PCT publication WO 94/18959, incorporated by reference herein.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in *The Pharmacological Basis of Therapeutics*, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Some methods of delivery that may be used include:

a. encapsulation in liposomes, b. transduction by retroviral vectors, c. localization to nuclear compartment utilizing nuclear targeting site found on most nuclear proteins, d. transfection of cells ex vivo with subsequent reimplantation or administration of the transfected cells, e. a DNA transporter system.

All publications referenced are incorporated by reference herein, including the nucleic acid sequences and amino acid sequences listed in each publication. All the compounds disclosed and referred to in the publications mentioned above are incorporated by reference herein, including those compounds disclosed and referred to in articles cited by the publications mentioned above.

Other embodiments of this invention are disclosed in the following claims.

TABLE 1

List of Candidate Compounds to Modulate ob

| CANDIDATE COMPOUNDS | REFERENCES |
|---|---|
| 1) Compounds Modulating Glucocorticoids | *p.1213 ff, and references therein WO/92/16546, PCT/US92/02024 WO92/16658, PCT/US92/02014 US 4,981,787 US 5,071,773 R. Evans, Science 240:889–895 (1988) |
| 2) Thyroid hormones and thyromimetics | |
| 3) Fibrates, free fatty acids & other agonists of PPAR such as Di (2-ethylhexyl)-phthalate & other plasticizers & herbicides such as | #36 (see INDEX) S. Green, Biochem. Pharm. 43:393–400 (1992) |

TABLE 1-continued

List of Candidate Compounds to Modulate ob

| CANDIDATE COMPOUNDS | REFERENCES |
|---|---|
| 2, 4, 5 trichlorophenoxyacetic acid and leukotriene antagonists | |
| 4) Antagonists of PPAR and subtype selective compounds (see Section II, item no. 43) | |
| 5) RAR selective agonists & antagonists including subtype selective compounds | WO 91/07488 PCT/US90/06626 |
| 6) RXR selective agonists & antagonists including subtype selective compounds | PCT/US93/10094, WO94/15901, PCT/US92/11214, WO93/11755, PCT/US93/10166, PCT/US93/10204 WO94/15902 PCT/US93/03944 WO93/21146 Boehm, M. F. et al., J. Med. Chem. 37:2930–2941 (1994), #43 |
| 7) Estrogens-agonists & antagonists | *p. 1193 ff and references therein |
| 8) Androgens-agonists & antagonists | *p. 1208 ff, and references therein US 4,144,270 US 3,847,988 US 3,995,060 |
| 9) Progestins-agonists & antagonists | *p. 1200 ff, and references therein |
| Non-steroid progestins | PCT/US93/03909 PCT/US93/10086 WO 94/24080 |
| 10) Mineralocorticoids-agonists & antagonists | *p. 1213 ff, and references therein |
| 11) Insulin | from Obesity to Diabetes J. P. Felber, K. J. Acheson, Luc Tappy, John Wiley & Sons, 1993 pp. 33–44 |
| 12) Glucose, glucagon, free fatty acids, amino acids, sugars & other secretagogues such as buguanides (antidiabetics, e.g. AD4743, metformin & phenformin), pyroglyrides, linoglyrides & benzothenediones | #67, 68 compound (See INDEX) |
| 13) Non steroidal anti-inflammatory drugs | #61 (See INDEX) |
| 14) Prostacyclins | #61 (See INDEX) |
| 15) Dihydroepiandosterone and precursors and derivatives including Dioscorea spp. & aloe vera extracts & compounds derived therefrom | #15, 62, 64 (See INDEX) |
| 16) Tumor necrosis factors | #51, 52, 53 (See INDEX) |
| 17) Cytokines & related signaling molecules & growth factors | #54 (See INDEX) |
| 18) Fetuin | #65 (See INDEX) |
| 19) Amylin agonists & antagonists | |
| 20) Prolactin | p. 452, Obesity |
| 21) Niacin, acepimox & other nicotine acid derivatives | p. 765 in Obesity |
| 22) Triacsins | #66 (See INDEX) |
| 23) Amphetamines & derivatives including fenfluramine & dexfenfluramine | pp. 414–418, in Obesity |
| 24) Endorphin antagonists | |
| 25) Somatostatin | *p. 858 ff, |
| 26) Cholecystokinin | pp. 399–401 in Obesity |
| 27) Bombesin | pp. 402–404 in Obesity (Brodoff) |
| 28) Gastrin | p. 403 Obesity |

TABLE 1-continued

List of Candidate Compounds to Modulate ob

| CANDIDATE COMPOUNDS | REFERENCES |
|---|---|
| 29) Oral anti-diabetic agents & eventual antagonists | #67 (See INDEX) |
| 30) Corticotropin releasing hormone | #70 & 16 (See INDEX) pp. 545–547 in Obesity |
| 31) Adrenocorticotropic hormones | |
| 32) Melanocyte stimulating hormone | |
| 33) Gastric inhibitory peptide | #71 |
| 34) Growth hormone agonists & antagonists | pp. 103–104 in Obesity; Pathophysiology, psychology and treatment G. L. Blackburn, ed. Chapman & Hall (1994) |
| 35) Beta adrenergic agonists & antagonists including phenoxybenzamide fluloxetine | #56, 57 (See INDEX) pp. 766–769, 774 in Obesity, |

*Intracellular receptor general reference Comprehensive Medicinal Chemistry "The Rational Design, Mechanistic Study and Therapeutic Applications of Chemical Compounds," C. Hamsch, P. G. Sammes, John B. Taylor and John C. Emmett Vol. 3-Membrane and Receptors, Pregammon Press, Oxford, Ch. 16.3 Steroid Hormone Receptors pp. 1176–1226
*Obesity P. Bjorntorp and B. N. Brodoff, Eds. J. B. Lippencott Co., Philadelphia
INDEX
16. Muglia et al., Nature 373:427–432 (1995)
36. Auwerx et al. Hormone Research 38:269–277 (1993)
43. Salazar-Olivo et al., Biochem. Biophys. Res. Commun. 204:257–263 (1994)
51. Torti et al., Science 229:867–869 (1985)
52. Kawakami et al., J. Cell. Physiol. 138:1–7 (1989)
53. Hotamisligil et al., Science 259:87–91 (1993)
54. Gimble et al., Mol. Cell. Biol. 57:4587–4595 (1989)
56. Bouloumie et al., J. Biol. Chem. 269:30254–30259 (1994)
57. Lowell et al., Endocrinology 126:1514–1520 (1990)
59. Knight et al., Mol. Endocrinol. 1:36–43 (1987)
61. Negrel et al., Biochem. J 257:399–405 (1989)
62. Cleary et al., Proc. Soc. Exp. Biol. Med. 196 (1991)
64. Shantz et al., Proc. Natl. Acad. Sci. USA 86:3582–3856 (1989)
65. Gaillard et al., Biochim. Biophys. Acta 846:185–191 (1985)
66. Tomoda et al., J. Biol. Chem. 266:4214–4219 (1991)
67. Sparks et al., J. Cell. Physiol. 146:101–109 (1991)
68. Hiragun et al., J. Cell. Physiol. 134:124–130 (1988)
70. Rohner-Jeanrenaud et al., Endocrinology 124:733–739 (1989)
71. Eckel, R. H. et al., Diabetes 28:1141–1142 (1979)

TABLE 2

5'-UTR sequences obtained by 5'-RACE with human adipose total RNA.

Clone 1 (SEQ ID NO:41)    CGGTTGCAAGGCCCAAGAAGCCCATCCTGGGAAGGAAAATG...

Clone 2 (SEQ ID NO:42)    CGCAGCGCCAACGGTTGCAAGGCCCAAGAAGCCCATCCTGGGAAGGAAAATG...

Clone 3 (SEQ ID NO:43)    AGCGCCAACGGTTGCAAGGCCCAAGAAGCCCATCCTGGGAAGGAAAATG...

Clone 4 (SEQ ID NO:43)    AGCGCCAACGGTTGCAAGGCCCAAGAAGCCCATCCTGGGAAGGAAAATG...

TABLE 3

5'-UTR sequences obtained by 5'-RACE using human adipose cDNA.

Clone 5 (SEQ ID NO:44) AGCGCCAACGGTTGCAAGGCCCAAGAAGCCATCCTGGGAAGGAAAATG...

Clone 6 (SEQ ID NO:44) AGCGCCAACGGTTGCAAGGCCCAAGAAGCCATCCTGGGAAGGAAAATG...

Clone 7 (SEQ ID NO:44) AGCGCCAACGGTTGCAAGGCCCAAGAAGCCATCCTGGGAAGGAAAATG...

TABLE 4

Comparison of 5'-UTR sequence obtained from 5'-RACE with the human genomic ob DNA sequence.

Clone 2 (SEQ ID NO:45)　　　　CGCAGCGCCAACGGTTGCAAGGCCCAAGAAGCCCATCCTGGGAAGGAAAATG...
　　　　　　　　　　　　　　　　　　　　　||||||||||||||||||||||||||||||||||
Genomic (SEQ ID NO:46) ...CTTGCAGTGTGTGTTCCTTCTGTGTCAGCCCAAGAAGCCCATCCTGGGAAGGAAAATG...

TABLE 5

Effects of administration of different doses of BRL 49653 on body mass, liver weight and weight of the epidydimal fat pad.

| | Body Mass (g) | Epidydimal fat (g) | Liver (g) |
|---|---|---|---|
| Control | 344 ± 22 | 2.5 ± 0.3 | 16.8 ± 1.3 |
| BRL 49653 (1 mg/kg/day) | 355 ± 21 | 3.3 ± 0.2* | 17.9 ± 1.3 |
| BRL 49653 (2 mg/kg/day) | 361 ± 18 | 3.8 ± 0.5* | 18.9 ± 0.6 |
| BRL 49653 (5 mg/kg/day) | 338 ± 9 | 4.0 ± 0.6* | 17.4 ± 1.8 |

(*Statistically different from control, $p < 0.05$)

What is claimed is:

1. An isolated, purified, enriched or recombinant nucleic acid comprising a control region of the human ob gene wherein said control region is selected from the group consisting of 5' non-coding sequence of SEQ. ID. NO. 1, intron one of SEQ. ID. NO. 3, and SEQ. ID. NO. 4.

2. The nucleic acid of claim 1, wherein said control region comprises the sequence 5' to exon 1 of said human ob gene cloned in a P1 plasmid or a portion thereof, wherein said P1 plasmid is selected from the group consisting of P1 clone 5135, P1 clone 5136, and P1 clone 5137, all of which are deposited at American Type Culture Collection with accession numbers 69761, 69762, and 69763, respectively.

3. The nucleic acid of claim 1, wherein said control region comprises a positive transcription element capable of up regulating or a negative transcription element capable of down regulating the transcription of said human ob gene.

4. The nucleic acid of claim 3, wherein said negative transcription element comprises nucleotide −978 to −217, relative to the transcription initiation site, of said human ob gene or its complementary strand.

5. The nucleic acid of claim 3, wherein said negative transcription element comprises −1869 to −217, relative to the transcription site of said human ob gene or its complementary strand.

6. The nucleic acid of claim 1, wherein said control region is from the 5' upstream of the transcription initiation site of the human ob gene.

7. The nucleic acid of claim 1, wherein said control region is from a region between the transcription initiation site of the human ob gene and the HindIII site about 3 kb upstream of said transcription initiation site.

8. The nucleic acid of claim 1, wherein said control region is from a region between Exon 1 and Exon 2 of the human ob gene.

9. The nucleic acid of claim 1, wherein said control region comprises a transcription regulation element selected from the group consisting of PPRE, RXRE, GRE, insulin response element, SP1 binding site, Oct-1 binding site, serum response element, cAMP response element, AP-1 binding site, AP-2 binding site, NFκB site and C/EBP binding site.

10. The nucleic acid of claim 1, wherein said control region comprises a C/EBP binding site or a Sp1 binding site from SEQ. ID NO. 1.

11. Isolated, purified, enriched or recombinant nucleic acid comprising a promoter of a human ob gene capable of initiating the transcription of said human ob gene.

12. The nucleic acid of claim 11, wherein said promoter comprises nucleotide −217 to −1, relative to the transcription initiation site, of said human ob gene or its complementary strand.

13. The nucleic acid of claim 11, wherein said promoter comprises nucleotide −2921 to −1, relative to the transcription initiation site, of said human ob gene or its complementary strand.

14. The nucleic acid of claim 11, wherein said promoter comprises at least 60 contiguous nucleotides from nucleotide −217 to −1, relative to the transcription initiation site, of said human ob gene or its complementary strand.

15. A recombinant nucleic acid comprising a control region of a human ob gene tanscriptionally linked to a reporter sequence for the effective initiation or regulation of transcription of said reporter sequence, said control region comprising at least 12 contiguous nucleotides from a 5' non-coding sequence of said human ob gene selected from the group consisting of SEQ. ID. NO. 1, intron one of SEQ. ID. NO. 3, and SEQ. ID. NO. 4.

16. A vector comprising the recombinant nucleic acid of claim 15, wherein said control region and reporter sequence are inserted therein.

17. A vector comprising the recombinant nucleic acid of claim 15, wherein said control region comprises a positive transcription element or a negative transcription element of said human ob gene.

18. The vector of claim 17, wherein said negative transcription element comprises nucleotide −978 to −217, relative to the transcription initiation site, of said human ob gene or its complementary strand.

19. The vector of claim 17, wherein said negative transcription element comprises nucleotide −1869 to −217, relative to the transcription initiation site, of said human ob gene or its complementary strand.

20. The vector of claim 17 selected from the group consisting of pGL3-OBΔ12 and pGL3-OBΔ5.

21. An isolated, purified, enriched or recombinant nucleic acid comprising a control region of the human ob gene wherein said control region is selected from the group consisting of SEQ. ID. NO. 1, inton one of SEQ. ID. NO. 3, and SEQ. ID. NO. 4.

22. An isolated, purified, enriched or recombinant nucleic acid consisting of a fragment of at least 12 contiguous nucleotides of SEQ. ID. NO. 1, or intron one of SEQ. ID. NO. 3, or SEQ. ID. NO. 4.

23. An isolated, purified, enriched or recombinant nucleic acid of claim 22, consisting of a fragment of at least 30 contiguous nucleotides of SEQ ID. NO. 1, intron one of SEQ ID. NO. 3, or SEQ ID. NO. 4.

24. A vector comprising a recombinant nucleic acid comprising a promoter of a human ob gene and a reporter sequence; wherein said promoter is tanscriptionally linked to said reporter sequence so as to effectively initiate the transcription of said reporter sequence.

25. The vector of claim 24, wherein said promoter comprises nucleotide −2921 to −1 , relative to the transcription initiation site, of said human ob gene or its complementary strand.

26. The vector of claim 24, wherein said promoter comprises nucleotide −217 to −1, relative to the transcription initiation site, of said human ob gene or its complementary strand.

27. The vector of claim 24 selected from the group consisting of pGL3B-OB1, pGL3B-OB2, pGL3B-OB3 and pGL3B-OB4.

28. A method for screening for an agent modulating the expression of a human ob gene, comprising the steps of:

providing a cell containing a control region of said human ob gene and a reporter sequence transcriptionally linked to said control region wherein said control region is effective to initiate, terminate or regulate the transcription of said reporter sequence;

contacting a agent with said cell; and comparing the level of transcription of said reporter sequence with the level in the absence of said agent; wherein a measurable difference in the level of transcription of said reporter sequence is an indication that said agent is useful for modulating the expression of said human ob gene.

29. The method of claim 28, wherein said control region and reporter sequence are inserted in a vector.

30. The method of claim 28, wherein said cell further comprises a transcriptional protein.

31. The method of claim 30, wherein said transcriptional protein is an intracellular receptor.

32. The method of claim 31, wherein said intracellular receptor is PPARγ or PPARα.

33. The method of claim 30, wherein said transcriptional protein is expressed from a recombinant nucleic acid in said cell.

34. The method of claim 30, wherein said transcriptional protein binds to a C/EBP site in SEQ. ID NO.1.

35. The method of claim 28, wherein said control region and reporter sequence are inside a preadipocyte cell.

36. The method of claim 28, wherein said control region and reporter sequence are inside an adipocyte cell.

37. The method of claim 28, wherein said control region and reporter sequence are inside a primary adipocyte cell.

38. The method of claim 28, wherein said control region and reporter sequence are inside a cell selected from the group consisting of COS, 3T3-L1, rat primary adipocyte, human primary adipocyte, mouse primary adipocyte and immortalized adipocyte cell.

39. The method of claim 28, wherein said agent is selected from the group consisting of glucocorticoids; thyroid hormones; thyromimetics; fibrates, free fatty acids and other agonists of PPAR including Di-(2-ethylhexyl)-phthalate, plasticizers and herbicides including 2,4,5-trichlorophenoxyacetic acid and leukotriene antagonists; antagonists of PPAR and PPAR subtype selective compounds; RAR selective agonists and antagonists including subtype selective compounds; RXR selective agonists and antagonists including subtype selective compounds; estrogens and other agonists and antagonists of ER; androgens and other agonists and antagonists of AR; progestins and other agonists and antagonists of PR; non-steroid progestins; mineralocorticoids and other agonists and antagonists of MR; insulin; glucose; glucagon; free fatty acids; amino acids; sugars and other secretagogues including biguanides; antidiabetics including metformin and phenformin; pyroglyrides; linoglyrides and benzothenediones; non-steroidal anti-inflammatory drugs; prostacyclins; dihydroepiandosterone and stimulators, precursors and derivatives thereof including Dioscorea and aloe vera, and extracts and compounds derived therefrom; tumor necrosis factors; cytokines and related signaling molecules; growth factors; fetuin; Amylin agonists and antagonists; prolactin; niacin; Acepimox and other nicotinic acid derivatives; triacsins; amphetamines and derivatives including fenfluramine and dexfenfluramine; endorphin antagonists; somatostatin; cholecystokinin; bombesin; gastrin; oral anti-diabetic agents; corticotropin releasing hormone; thiazolidinedione compounds; adrenocorticotropic hormones; melanocyte stimulating hormone; gastric inhibitory peptide; growth hormone agonists and antagonists; β-adrenergic agonists and antagonists including phenoxybenzamide; fluoxetine; neuropeptide Y and agents modulating neuropeptide Y activity or expression.

40. The method of claim 28 used to screen for an agent increasing the transcription of said human ob gene, wherein said agent is selected from the group consisting of PPARγ antagonist, C/EBP protein agonist, PPARα agonist, glucocorticoid, insulin derivative, insulin secretagogue, insulin sensitizer and insulin mimetic.

41. The method of claim 28 used to screen for an agent decreasing the transcription of said human ob gene, wherein said potential agent is selected from the group consisting of PPARγ agonist, C/EBP protein antagonist, PPARα antagonist, glucocorticoid antagonist, and insulin antagonist.

42. The method of claim 41, wherein said PPARγ agonist is a thiazolidinedione compound.

* * * * *

SEQUENCE LISTING (1) GENERAL INFORMATION:

(iii) NUMBER OF SEQUENCES:       48

(2) INFORMATION FOR SEQ ID NO: 1:

(i) SEQUENCE CHARACTERISTICS:
      (A) LENGTH:         294 base pairs
      (B) TYPE:           nucleic acid
      (C) STRANDEDNESS:  single
      (D) TOPOLOGY:      linear (ii) MOLECULE TYPE:     DNA (genomic)
      (A) DESCRIPTION:   Sequence upstream of exon 1
           including a promoter (xi) SEQUENCE DESCRIPTION: SEQ ID NO: 1:

```
CGCCATAGTC GCGCCGGAGC TCTGGAGGG ACATCAAGGA TTTCTCGCTC CTACCAGCCA      60

CCCCCAAATT TTTGGGAGGT ACCCAAGGGT GCGCGCGTGG CTCCTGGCGC GCCGAGGCCC    120

TCCCTCGAGG CCCCGCGAGG TGCACACTGC GGGCCCAGGG CTAGCAGCCG CCCGGCACGT    180
```

```
CGCTACCCTG AGGGGCGGGG CGGGAGCTGG CGCTAGAAAT GCGCCGGGGC CTGCGGGGCA      240

GTTGCGCAAG TTGTGATCGG GCCGCTATAA GAGGGGCGGG CAGGCATGGA GCCC            294

(2) INFORMATION FOR SEQ ID NO: 2:

(i) SEQUENCE CHARACTERISTICS:
        (A) LENGTH:         30 base pairs
        (B) TYPE:           nucleic acid
        (C) STRANDEDNESS:   single
        (D) TOPOLOGY:       linear (ii) MOLECULE TYPE:     DNA (genomic)
        (A) DESCRIPTION:    Sequence of exon 1

(xi) SEQUENCE DESCRIPTION: SEQ ID NO: 2:

CGTAGGAATC GCAGCGCCAA CGGTTGCAAG                                        30

(2) INFORMATION FOR SEQ ID NO: 3:

(i) SEQUENCE CHARACTERISTICS:
        (A) LENGTH:         10684 base pairs
        (B) TYPE:           nucleic acid
        (C) STRANDEDNESS:   single
        (D) TOPOLOGY:       linear (ii) MOLECULE TYPE:     DNA (genomic)
        (A) DESCRIPTION:    Sequence between exon 1 and exon 2

(xi) SEQUENCE DESCRIPTION: SEQ ID NO: 3:

GTAAGGCCCC GGCGCGCTCC TTCCTCCTTC TCTGCTGGTC TTTCTTGGCA GGCCACAGGG       60

CCCCACACAA CTCTGGATCC CGGGGAAACT GAGTCAGGAG GGATGCAGGG CGGATGGCTT      120

AGTTCTGGAC TATGATAGCT TTGTACCGAG TTCTAGCCAG ATAGAAGGTT ACCGGGAGCT      180

GGGGAGCGTT GGATTTGCTG CTGGGCTGTG CCGGTGCCCA GAAGGCAGGA CCTTGCAGAA      240

CCAGCCAGGT CCCTGGGAGA CTGTCAGACC CACCAACCTG GTGGCATTCG CAGAGCTGAG      300

ATGCATTGGA AATTGCCTTG GCACATCCC CAAAGATCAG GATGTCCCAC CCCAGTCTGA       360

AGGAGATAAA GTTGGGGGTA GGAGAGACGC AGATGCAAGT GATCAGTCTC AGTCCCAGAC      420

ATTGCCTTGC TCTGCGGGTA GGAATTCAGG ATTCATTTTC CAGGGAAGTT CCTGACCTCT      480

GAATGAGAGG GGCTGTGTAA GGCCAATGCC TGGGAGGAAG GCAAGGATGA GTAGAGGTGG      540

GGGGAAACAA GTGTCAGGAA GACTCAAAAT CTTCCAGAGA AATTGTGCAG GGTCTTACCA      600

GATCTGTCCT CAAAGCCATG CAAATTGCCT TCTTTGCAAT GCATACAATG AGGTGTCTCT      660

GGGGGTCAGA ACTGGTTATT AGGGAACTTC TAGCCAGGAC TGCTAAATAC GCGCTGTTGG      720

CCCACCAGGC TCACCTATAG CCTTCCTTCA GTCTGGGCTT GGTTTGGATT TCACTGTGGG      780

TGCCATCGCC TTTACACTCC TGTTTCTATA GTTTAAAGAT AGTGGTGCTT TGGGAAAGTG      840

ACTCCTTAAA TACAGTTAGG TCCAAGTGAG ACAAGTGGCC TGGCTGTCAT TTCAGAATAG      900

CAGCTTCCAA GAGGTGATTA ATTTCTGTTG GAAGGGTGAT CTTTGGGGAG GTGGGTGAAG      960

AGCAGAGACT TGGTGGTACC GTTCCAGGAG CACAGGCTCT CTTCCTTTGC AGTGCAGAAT     1020

GACCTCTGGC AGCCGGAGTT GTGTTTGTTC TGTAGGATTC TGAGGTGGGC CATGGGCAGC     1080

TGGAACTGGG GAATTTTGCC AATCTCTTTC ATATTAGGAT TGTCTGCAGA ACCAGATATG     1140

GAGGCTTCTA GCAACGTGAG TGCTCCTGTT CTAATGCCCT TAGAAACAAG AAGGCCACAC     1200

TGATCATTTC TCTCACTTAG GCAGGAGAC AAGGCAAGAG AGAAACAGTG GATGCTTTTA      1260

GGTTCTTTCC CTTCCCAAGC AGTTGTGGAC ATTGGGCTGA GGGGAACATT TCCACATTGG     1320
```

-continued

```
CTAAAGGAGC GTCCTCCTCA TATTTTGTAC ATTTTATACC CAAAATAACT CTTCTTGGTA    1380

TTTGGGAAA TATTTTCCTC CCCGTCCATT CCAGGAAATG GCTCCAAGTG CCAAGGACAG    1440

AGCCAGGGAA GTTGCAATGA ATTCCTGCCC GTCAGCCCCA GGCAGATGCC TTGCACGTCT    1500

GAGTGGCCCA TGCAGAGCGT GGAGGTGGCC GCCACGGAAC CTGGGTCAAT GTCCCACCCC    1560

CGCTTAGATG CCACCAGGGG CGTGGGAGCC AAGGAGAGAA GAGGGCTCC AGGAAGGTAG    1620

AGTCCTTGTG TCTTGTGCAT CTGTGAACAG CACTGGTATG ATTTAAAGGA AAATTGAGCC    1680

AAATTTTCCG GCAGTCAGTT ACCCCATCCC CACCGGGGTA GGAGTCTGGC AGCCGCAGCT    1740

CCATTCTGGC CAGTCGGCAG AGAGCCTTGA AATTCTTCTT TGTCCACACA GTTGTCTCAG    1800

AGAAACAGAG AGGTTGTTTC TGCTTAAAAA CAACACACTT GGTGTCTGGG CCCACAGACT    1860

CCTTTGCACT TATTCCACGT GTGACAGCCA ATGTGCCTCG TTGCTTAGCA GACAGCATGT    1920

TACCGTCTTT CCTGCTCAGT TTGTTAGCTC TATGGAATGG AATCTATAAT CAATGCCCAT    1980

ACCAACATTT CACTAATATC ATAGGAGATT TAGTCTCCAT CTGGGTGTAC ATTACATTTG    2040

CTCTGGGGTG CTCCAGGCTG GGGGGTTGCC AAGGAAGAGA AGAGAAACCG CAGAGAAGAC    2100

GGGAGGGCAG GGCAGGGGTC TCTGAGAAGG GGAGGGGTCC CAGAGTGCAG GAGCAGGAGC    2160

CAGGCTCATG AAAGGGGCCA CGGGCGGGAG TATCCAGGGA CGGCAGTCAA GATGGAGCAC    2220

AGCTTAGGAA GCTGAAGGGA ATCCTGGCCC ACCTGGGTGC TAGAGGGCAC ATAGGAAGTG    2280

CAGGAAGCAG ACCAAGGTCC CCAAGAGAGG GAGACCTGGA CGCTGAAGCA TTTTCAGTCT    2340

TTATTAAGAC AACTCCGTAA GAATTCCTGC TGGGCCAAAG TGAATTCTAG GATGCGACTT    2400

TAAGATGGGA GCAAGCGAAC CATTGAGGAG GCAGGTTACC CTAGTTAGCC AATGCAGATC    2460

GAGAATGGGA AATCTTTCAT TTATTCATGC AACAGATATT TATCGAAGCC CTGCCGTGTT    2520

CCAGGCCTGT GATAGATGCT GGAACAGGTA CAGAGATACA GGTGTCATTA ATTGATCAGG    2580

GCAACCTCTC CTTCTGAGTC TTGCTGGAGC TTCAGATGCC CCTCACACAG AGCTCGAGGG    2640

AGCCTCAACA ATTGATCAGA AGTCAGGCAC CATGGCTCAC GCATATAATC CCAGCACTTT    2700

GGGAGGCCAA GGCAGGTGGA TCACTGGAGC CCAGGAGTTC CAGATCAGCT GGGGCAACAT    2760

GGCAAAACCC CATCTCTATT AAAAAAAAAA AAAATTAACT GGATGTGATG GTACACACCT    2820

GTAGTCCCAG CTACTTGGGA GGCTGAGAGG TGGGAGAATT GCTTGAGCCC GGGAAGTCGG    2880

GGGTCCAGTG AGCCTTGATC ACACCACTGC ACTCCAGCCT GAGTGACAGA GCAAGACCCT    2940

GACACACACA CACACACACA CACACACACA CAGATTAGAG CTGAAACAGG AGTAGAAACC    3000

TATCTGTATC TCTGATGAGA TCAGATTTTT CTGATGAACA GAAAGAATGT AACCCCTGTA    3060

CTCACACCCT CTCTGCTGGT TACATATGTT AACACGATTT CTCAAATGAG GCTTTTGGGT    3120

TGCAAATAAG AGAAAATCAC TCACGCTGGC CCTGTGTTTT TCAAATTGTT TATTGTGATC    3180

AACATTTGAA AAAAGAGCCG AGACTCTCAA GAGTGCATTA CCCACGGTAA GGGTGAATTT    3240

TACTTCTTGA CACTTATTTC TCTTACATGT ATCTATCTGT CTCAAATGAA AAATATATTT    3300

AGAAAGTTGA AAGCTATCCA AGTGAGTATA AGAAAAGAGT ATCTCACCCT GAAGGCTAAG    3360

GACAGGGAGG GCCACCAGGC CTCACGAGGA CCCAGGAACC ACAAAGAAGG CTAGGAAGGA    3420

GCACAGGCGG TGACCATACT CTGGCTCAGT GGCTATGTGG GCTCTGGTCT CTCTCAGCTG    3480

TTCCATGCAT ATGAGGCCAA ATGTGGCTAC CCTAGAGCTT CTGAGCCCTC AACAGAGATG    3540

AACTGGACTC TCTGCAGCCC CACTCTAAAT TCCTAAGAGA GAAGTTGATT GACCCAATCA    3600

GGGTCAGGAG AAGGAAGGGA GGAGGAAAGG GAGGAGAGAA GAGCCTCTTC GTCTCTTGCC    3660

TACCACTGGC CAGGCAATTG TAGCCAAGGG GGCTGGAGTG TAAATGCAAA CATAGCCATC    3720
```

```
AAGGGTTGTG TATGTGTGTG TGTGTGTCTG TGTGTGTGTA TGTGTGTCTC TTGGGTAGGT      3780

TAGATCTCCC AGGAGGTCCC TACTAAACAG ACTTAAGCCC GCAAAATTTT AGCTCTCCAG      3840

CCTCACACAC TCCACCCCTC TACCATATTG AATCTTCCCA AACCAACTAT GGCTTTCCCT      3900

AACTCCGGAG CTTGGCCTGG AATGCCCTGC TTCCCCTCTT TCCCCTGGGG AACGCCTGTC      3960

CTTCAGGCCT CAGTTCACAC ACTGCCTCCC TTGCAAAGCT CTCCTCCCAT CCCCGGAGTC      4020

CCTCTTCCCC TTTGTTCTTT GGGTTCTATG CTTCTTCCCT CATAACTCCC ACCAGGTTGT      4080

GTTAAAATGA GTTGTTCAAG GTCCTGTCTG TTCCACTAGA TTCTGAGCAA CTTGGAGAAC      4140

GAAGATCCAA ACTTCGCTGC CTTTATTTCC TCCTTTGTTC TTTTCTCATC CCCAAGTCCC      4200

TTCCAACTTG GAGTTATGAA GAAAGGAAGG AAGGAAGGGT GGGAGGGAAG AACAGGAGGG      4260

GATCCCACAG GAGAATGTGT ATAGGGAGAG GACTCAGACT AGCTAAAGCT TTTCCCTCAT      4320

AATTAATAGC AAATACCATG TTACCTGAAT TTAATTCACA GTAGCATACA AAAGACTCGC      4380

TTTGTTCTCC CCATTGATGT CATCAGAGGG CTGTGGGCAG GCCTAATCTT GGCTCAGGAG      4440

GCCCTCCAGC CTGGATCTAA AGAGCAGCAG ATGGGCCAGG CTCGGTGGCT CATGCCTGTA      4500

ATCCCAGCAT TTTGGGAGGC CGAGGCGGGT GGATCACGAG GTCAGGAGTT TGAGACCAGC      4560

CTGGCCAAGA TGGTGAAGCC TCGTCTCTAC TAAAAATACA AAAATTAGCC AGGTGCGGTG      4620

GTGGGCGCCT GTATTTCCAG CTACCCGGGA GGCTGAGGAG GCTGAGGCAG GAGAATCGCT      4680

TGAACCCGGG AGGCGGAGGT TGCAGTGAGC CGAGGTCACG CCACTGCACT CTAGCCTGGG      4740

CAACAGAGCA AGACTCCGTC AAAAAAAAAA TAAAAAAATA AAAAAATAAA AAAAATAAAG      4800

AGGAGCACAC ATCTCTGCCC ATCCTAACTC CCACTTTGAC ATTGAGGTCC CCAGGATGGA      4860

GGGTCTGCCT CCATCTGCCT TGTCCCCTGC AATGGTGGGA AGGTGATGGA GCTCAAGTCT      4920

AGAGGCCACC AGCTTCTTAG GGAGGTAGGA GGTGGAGGGT GGGGTGCGGC CCCTGCACAC      4980

AACTGCCAAG TGAGGATGGG GGTGGGGTCC ACCTGAGGAT AAGTAACAGT GAGGCTGGTG      5040

CAGAGGACCC AGGTGGAGGT AGACAGCAGA ATTTGTGGTG GGGTGGATGG CACATTATAT      5100

AAGCCTCTCT TGCTGCCCTG TTTACTGAGA TTGTTTCATT ATCTTTTTTG GCTTTTGTTT      5160

TTAAGAGATG GGGTCTTGCT GTGTCACACA GGCTGGAGTG CACTGTGTGA TCATACCTCA      5220

CTGCAGCCTC GACATCCTGG GCTCAGGCAA ACCTCCCACC TTGGCCTCCC AAGTAGCTGG      5280

GACCACAAGC GTTTGCCACC ACACTCAGCT ATTTTTATTT TTATTTTTTT TTTTTTAGAG      5340

ATGGGGTCTT GCTGTGTCGC CCAGGCTGGT CTTGAACTCC TGGGCTCAAG CGATCCTCCT      5400

GCCTTGGCCT CCCAAAGCCC TGGGATTATA GGCTGAGGCC ACCACACCCA GCCACATTTC      5460

ATCTGTGCAG CTCCAGGGGC TCCACATTCT ACTCTTCTCA TTTCTTCTCC AGGGTACCCA      5520

TGGCAAGGGA TGAGGGTAGA AGATGGGGCA GCCAGGCCTT GATTAAAGGA GAAGGAAGGC      5580

AGCCTGTGGA GAGGGCAGCC CAGGGAGTGC AGAGAGAAGT GGCCCATGAG GGAGACAGCA      5640

GAGTGCAGCC TGCGTCCCAA ATGAGCACAC AGCCCACTGT GAGCCCACCA TCTTCCTAGA      5700

GACCCCTCTC CTCTCCAGGA GCTGCTTCAG TAGCACTCAG AGGAAAGAAT GATGCTGTAT      5760

CAACATTTCA GCAGCTCATC TTTTAACTCT AAGAAAATGG CAGCTCCTAA ATGTTCAAAA      5820

CTGCTTTGGA AACTTCTGGA GAGAGGTTTT GCAGCTCAGG CAGACAGCTG ATCGCGGCCT      5880

TTCTTCCACC CCAACCCATG CTCTCCCCAT GCTCTCCTGC CACAGCTGCA GCGGGCCCCT      5940

GGGTCCTACA TTTGCAGCCC TTTGTCTCTG AGCTCAGACT TCCAATTCCA AGCGGCAGCT      6000

GGGCAGGCTC ACCAGCATGT CCAGCCAGTA CTAGGACATC AGCAGGAGCC CAACCACCTC      6060
```

```
TTTCCAAAAT CTCTCCTCAT GTCTCTCCTA GTTTCCATCT CCATCCTTCT AGTCAGCCAG    6120

GCTGAAAACA TTTGCTCCTC AGGGTGCAGA AGGGAAAGCT TTGCCTCCCT TCCTGGTGCT    6180

CACTGCCCCT GCGATTCCAG CCCAAGCCCT CCCCGGCTCC TCACCCTGGT GTCAGCTGGA    6240

AGCCACCATC TCCTAAACCC ACCTGTGTTC TTCCACCTCT GCCAGGGCTG CCCTCTCCTC    6300

CACCTTCACA AACTCAATTC CTACCCATTG CTCAGGTCCC TTATCAAATG CCATCTCCTC    6360

CATGATGCCT CCCTGATTCC CCTGCTGGAA ATAATGGTGA TAACAGCTAA GGCATTGGGG    6420

TTGGCTACGT GCCAGGCAAG GAGTTGGCAC TTTACATGCT TTATCTCATT TCAGCCACAT    6480

AACATCGACA GGTGGCATTA TGATTCATAT CATCCCCATC TGATAGCCAG GAAAACTGAG    6540

TCCCAGAGAG GTTAGCCACT TTCCTAGGGC CCTGTGCTCT GACTCAAGCA TAGCTCTGAG    6600

GAACTCTAGC ATTCATCAGT TTAAGCACCA TGACTTTCTT TGCTGAGTCA CCCAAGGCAT    6660

TTCTTCATTT AAATGTTCTT CCTTGGCCAG GCGCAGTGGC TCAGGCCCAA TGCGGTGGCT    6720

CACGCCTGTA ATCTCAACAC TTTGGGAGGC CGAGGTGGGC AGATAATCTG AGGTCAGGAG    6780

TTCAAGACCA GCCTGGCCAA CATGGTGAAA CCCCATCTCT ACTAAAAATA CAAAAAAATG    6840

AGGCTGGGCG TGATGACTCA CACCTGTAAT CCCAGCACTT TGGGAGGCCG AGGCAGGTGG    6900

ATTACATGAG GTCAGGAGTT CGAGACCAGC CTGGCCAACA TGGTGAAATC CTATCTCTAT    6960

TAAAAATACA AAAAATTAGC CAGGCATGGT GGCAGGCACC TGTAATCCCA GCTACTTGGG    7020

AGGCTGAGGC AGGAAAATGG CTTGAACCCG GGAGGTGGAG GTTGCAGTGA GCCAAGGTTG    7080

CACCATTGGA CTCCAGCCTG GGCAAAAAGA GGGAAACATC GTCTAAAAAA GAAAAAAAAA    7140

AAATTAGCCA GGCTGGGTGG TGCATGCCCG TAATTCCAGC TACTCAGGAG GATGAAGCAA    7200

GAGAATTGCT TGAACCCAGG AGGCAGAGAT TACAGTGAGC TGAGATCACA ACACTGCACT    7260

CCAGCCTAGG TAAAGAACAA GACTCCATCT CAAAAATAAA TAAATAAAAA TAAATGTTCT    7320

TCCTTGCATT GAAGTTAAAT ATGTAAATTC TCAAACCAGT TGCTTAAGGG CACAGTTTTG    7380

GTTCTTTACC TATATTTTTA ACAAATATTT TATGTAAGTA GTTGACAAAA TCAAATACTG    7440

TGTACACTAC CGAGGCTTCC CTGGGAAAGC CATCAGCCTC TGCCCCATCC CTTCCCACTC    7500

CTGATTCCAC TTTCCTGTGT TTCCATATCT TTTTCATGTC TGTTTCTGGC CCACAGTGGG    7560

CGATCAATAC ATGTTAGCCA CCAACCATCA AACCTATATT GAGTAATTAT GGTATGTCAG    7620

GCACTATGCT CAATGAAATT GTATTAGGCT TGTACAAAAG TAATTGTGGT TTTTAAGAGT    7680

AATGGCAAAA ACGGCAGTTA CTTTCGCACC AACTATTTGG TGCCTTGAAT TATTCCTCCT    7740

CTCCTCATCC CTAAACCCTG CTCCTCCCAG CCATTCTTCC TCCCCTTCTT GGGCCATGGC    7800

CAGGCCCCAC CCAGGTACTA AGACTCAGGT GAACCAAGGA AGACTTAATG CCCACTCTTT    7860

TCTGATGCCC ATGTTGGCAT GTGTTAAGTC GGTTAGCATT AAGTTTGGCT GCATTTAGCA    7920

GAGACCCAAA AGAACAGTGC CTTTTAAAAG GCAGAGGTTA TGTCTCTCAC ACACACCCAG    7980

CACAAGTCCA AGACCAGCAT GGCATCTCAG CTCCATCAAC CTCAGGAACC GAGCTCCTGC    8040

AGCTCCCTGC CCTGCAGTTG ATAAGGTGAG GTCTTTGTCC TCCTGGTTCA AGATGGTGCT    8100

AGAATGTTGG CTACCATATC TATAGTCCAG GCATCAGAAT GGAGCAAGGG ATGAAAAAGG    8160

AAGAGATGAA GGCACACGAC AGGTTCCTGA GAGCTGGCAC AGGACACTTC TGCTTATATT    8220

TCACTGGCCA GAACTTAGTC ACATGGTCAC ACCTAGTTGG GAGACTCTGA GAAGTAAAGT    8280

ATTTATTCTA GATGGCCATA TCCCTACCTA AGACTTGGAG TTTTCTATGA CTGGGGAAGA    8340

ACGGAAGACA AGATATTGGG AAAGACTAGC AGCCTCTACT AAAAGGGTGA TCTGTGTTGA    8400

TGTGCGTGTG TGTGTGATGT TTGTATGAGC ATGTGTGTTA TGTGTTGTGT GTTGGTGGGG    8460
```

-continued

```
CAGATTCTTG CGAGCACTTT GGTCTCAGAT GGACCTGCTA CCAGTTCTCT CTGCAGACCC     8520

CCATAGGTTT CTCCTAAACC TGGCCTCTCC TATTAGGCAG CCTTACTCAG CGGCAGCTTC     8580

TCAGCTCCAT GTTTTCAAGG AACCACAATT TATTTCCAGC ATCCACTGAA GCATATTATC     8640

AGTGGTGATA GAGGGGGCTT GTAAAACTGT TTTTCCACTT AGGTATTAGA GGGTGGCCAT     8700

TACTTGAGAG TGACTATGAC CACAGTTAAT CTGGTAATAA ATTCTCTTGG GTAGGAGGAA     8760

AGGAAAGGAT GCTTTAAGGA AGCATCTTGC CGGGAGACAC AAAGCTAACA AGAGTGGAGC     8820

CTGCAGCTGG AGCCGCAGAG CCTAATCACT ACACCCGCCC ATCTCTGCTA GGGTTTCATG     8880

ACTTCGTATC GGGGATTAGC AGTATTTAAC TCTGTTGCAC AAACATTTGG TGTATTATTC     8940

AGGTAACAAG TAGCTAATAG AGGAAGTTTT ACTTTTTTAA GACATAAATT TGCCTTTTCC     9000

CAAATTACTT GGTACATAGT ACTTTTCATG TTTGAAGTTG AGATGTGGGT ACAATACCAT     9060

AGCTTTATTC CAGAGCAGGG TATTTGTTTC CAAATGCCAT GTTCCCAGCA GCTGCCCTTG     9120

ACTGGGAATT GGGGTGTGAT TTGGGCTTTT CCTTAAATCC TTGAGGAGCT GGAGGGGTGG     9180

GTGGCTCGCA CTCCTGCTTT CTGGATCTGA ATCCTGACTC TGTCATGGAC CTGTTTGACT     9240

TTGGGCAAGT TGACTCCTAT TCCTGAGCCC CATATTTTTC TCTTCTGTAA AATTCAGATT     9300

AAAAAAACAT GGCTTTGATC AAACATTATA AATAATATAT AGACAGACTG CTTGTTTTTA     9360

TTGTATTGCC AGAAATGAAT CCTACTAATA TTGCCATCTA TGGACAGAAA ATGTATTACC     9420

TGTCTTCATC AAGACCCAGA CGAGGAAGAA CACGAAAAGC GGAGATTAAT TTTACTGCCA     9480

TCTCCAGAAC CGTCATCCTA ATATTTACTT ACATTTTATT ATTATTTCAG GCTCATGCAC     9540

ATATACTTAG CATGGATCAT TGGCCACAGA CTCGCATACA TTTAACTTTA TTACCTTTTG     9600

CCTCATGTAT CTCATTAAAA TTTTGCTGCT TAATCAAGGA TCTGCATATT ATTTTAATTT     9660

TAGAATTCAC AGTTCCAAGA CTTTGAAAGT TTCAAGCGTT CTGGGTGAAT GTGTTATGCT     9720

CTCTCCCACC ACCATGTCTT TATACCCCCT GATTTCTCAG CCACTATGGC AACCACTTTC     9780

TACTCTTAGT AGCCCATATT TAGTCCAATC CCCAGCTCAG GAAGACACTT CTTCCAGGGA     9840

GCCCCCTGTG CCTTCCAGTA GTATCTTTGT ACCCTGCCCT TTTTCCAAAG CTCTTTCCTC     9900

CTGGCTTAGA ATGGCCCATT GACCTGTTTG TTTCTCCTAT TAAACTGTAA GCCACTCGAG     9960

GGTAGAGAGC ATCTGTTGTT CACCATTGCA TCCTCGGTGC TGAGCACTGC GTCTGACATA    10020

TTATTTAGAA GGTCAGTAAG TGCTAGTGGG ATTCAGGCTC CCAGTGGGTG GGAGAGAAAG    10080

GACATAAGGA AGCAAGTGGT AAAGGCCCTC ACAGAGTATC AGCAGGCTGG TGTGAGGGAG    10140

AAATGCAGAG GATGGGTGAG TAGCATAATC GCTAATGATA GGGTAATGAT AGAGCACATT    10200

TCACAACACC TTTAAGCCCT TTCACGTGCA TCAGATAATT TGATCCTCAT AGAAGCCTAG    10260

AGATAGATAT ATTACAGGGA TGAAGGTGGA GTATTTTGTG GTTATGTGAT ATGTTTAAAA    10320

TTATGCAGTG AGTAAATGAC TGGGTTCAAA CCAGACCTTA AAAGTCTGTT ATCTTTCCCT    10380

CGAGCATGCA ATGAAGTCTA CATCATCCCT ACCATGTCCA TTTGATCACA CCCTGGCCTC    10440

ACAGCTCTGT GGTCTACAGG ATACCTCATG GTGGTTTTAT TGACCAGACA ATAATCCTCT    10500

TTCTAAGGGG ATGCATTTCA TTAATACATA TGTAGATCAT GAATTGTCTT TGACTTTGAG    10560

GGGATGGTAG CCAGAGCAGA AAGCAAAGCT GATTTTCATC CCCGTCTGGT AATGTGGTTG    10620

GTAATGTGAA GATGGGTGTA TTCTGAGATA CCGGCTCCTT GCAGTGTGTG TTCCTTCTGT    10680

GTCA                                                                 10684
```

(2) INFORMATION FOR SEQ ID NO: 4:

```
    (i) SEQUENCE CHARACTERISTICS:
         (A) LENGTH:          2921 base pairs
         (B) TYPE:            nucleic acid
         (C) STRANDEDNESS:    single
         (D) TOPOLOGY:        linear (ii) MOLECULE TYPE:        DNA (genomic)
         (A) DESCRIPTION:     Sequence upstream of the
             transcription initiation site (xi) SEQUENCE DESCRIPTION: SEQ ID NO: 4:

AAGCTTCTTT AAGGATGGAG AGGCCCTAGT GGAATGGGGA GATTCTTCCG GGAGAAGCGA      60

TGGATGCACA GTTGGGCATC CCCACAGACG GACTGGAAAG AAAAAAGGCC TGGAGGAATC     120

AATGTGCAAT GTATGTGTGT TCCCTGGTTC AAGGGCTGGG AACTTTCTCT AAAGGGCCAG     180

GTAGAAAACA TTTTAGGCTT TCTAAGCCAA GGCAAAATTG AGGATATTAC ATGGGTACTT     240

ATACAACAAG AATAAACAAT TTACACAATT TTTTGTTGAC AGAATTCAAA ACTTTATAGA     300

CACAGAAATG CAAATTTCCT GTAATTTTCC CGTGAGAACT ATTCTTCTTT TGTTTTGTTT     360

TGCGACAGGG TTGCGCTGAT CCTCCCGCCT CAGTCTCCCT AAGTGCTGAG ATGTTGCAGG     420

AAGTCAGGGA CCCCGAACAG AGAGATCGGC TGGAGCCGTG GCAGAGGAAC ATAAATTTTG     480

AAGATTTCAT TTTAATATGG ACACTTATCA GTTCCCAAAT AATACTTTTA TAATTTTTA      540

TGCCTGTCTT TGCTTTAATC TCTTAATCCT GTTATCTTCA TAAGCTAAGG ATGTACGTCA     600

CCTCAGGACC ACTGTGATAA TTGTGTTAAC TGTACAGATT GATTGCAAAA CATGTGTGTT     660

TGAACAATAT GAAATCAGTG CACCTTGAAA AAGAGCAGAA TAACAGCAAT TTTTAGGGAA     720

CAAGGGAAGA CAACTATAAG GTCTGACTGC CTGCGGGGTC GGGCAAAGGG AGCCATATTT     780

TTCTTCTTGC AGAGAGCCTA TAAATAGACC TGCAAGTAGG AGAGATATTG CTAATTTCTT     840

TTGCTAGCAT GGAATATTAA TATTAACACC CTGGGAAAGG AATGCATTCC TGGGGGGAGG     900

TCTATAAATG GCCGCTCTGG GAATGTCTAT CCTACGCAAC GGAGATAAGG ACTGAGATAC     960

GCCCTGGTCT CCTGCAGTAC CCTCAGGCTT ACTAGGGTGG TGAAAAACTC CGCCCTGGTA    1020

AATTTGTGGT CAGACCAGTT TTCTGCTCTC GAACACTGTT TTCTGTTGTT TAAGATGTTT    1080

ATCAAGACAA TACGTGCACC GCTGAACACA GACCCTTATC AGTAGTTCTC CTTTTTGCCC    1140

TTTGAAGCAT GTGATCTACT CCCTGTTTTA CACCCCCTCA CCTTTTGAAA CCCTTAATAA    1200

AAAACTTGCT GGTTTGAGGC TCAGGTGGGC ATCACAGTAC TACCGATATG TGATGTCACC    1260

CCCGGCGGCC CAGCTGTAAA ATTCCTCTCT TTGTACTCTC TCTCTTTATT TCTCAGCCAG    1320

CTGACACTTA TGGAAAATAG AAAGAACCTA CGTTGAAATA TTGGGGGCAG GTTCCCCCAA    1380

TATCTGGTGC CCAACGTGGG ATACTGAGAT TACAAGCATG AGCCACTGCA TCTGGCCTCT    1440

TCTTTTGATT TTTTTTTTTC AAACTTTTAC AAATGTAGAA ACCATTCTTA GCTTTTGGGC    1500

ATTACCAAAC CCGGCAGTGG CAGGCTCGGT TCACCGACGT CATTTGCAGT TCCCCGCTTT    1560

ATGTTATGGG TTTTGTTTTG TTTTGTTTTT TTTATTGAGA CAGAGTTTCA CTCTTGTTGC    1620

CCAGGCTGTA GTGCAATGGT CTGATCTTGG CTCACTGCAA CCTCCACTTC CCAGGTTCAA    1680

GCCATTCTCC TGCCTCAGCC TCTCAAGTAG CTGGGATTAC AGACACTCAC CACCACACCT    1740

GGCTAATTTT GTATTTTTAG TAGAGATGAG GTTTCACCAT GTTGGCCAGG CTGGTCTCGA    1800

AATCCTGACC TCAGGTGATC CACCCACCTT GGCCTCCCAA AGTGCTGGGA TTACAGGCTT    1860

GAGCTACCAC GCCTGGCTGG GTTGGTTCTC AATGGAGTGG TTTGTTTTTG GAGCTGCTCT    1920

GCGCAGTGGG GACCAGAATA GGCCTGGGTT CCTAGCCCAT TGCTATTCCT TACCAGCTGT    1980
```

```
GGATTCTAAG GAAAGTCATT TAACCTCGCT GGACCTTAGA TTCCTCATCC CTGAAGCCCA      2040

AGGGTAAAAC AAAACAAAAC AAAACAAAAC AAACCAACCC ATCATGTAAA GCGGGGAACT      2100

ACAAACGATA CAGGTGAAAC ATGCCTACCA CACCACTCAC AGGCTATGAT GACAAAAACG      2160

TGGCTACATC TGGGACCACC CCCCAACCCC CACTTTGTAC GTAGGAAATA CGGAGTTGAG      2220

GATGGAGACC CACAGTATGT CCAGAGTGTC CCCAAAGGCC ACAGTGCCCG CCTGGAGCCC      2280

TCCAGAGAGC GTGCACTCCC TGGGGTGCCA GCCAGAGACA ACTTGCCCTG AGGCTTGGAA      2340

CTCGATTCTC CGCGTGCCAG AGAAGGGGTG GGACTTCAGA ACCCCAACC CCGCAATCTG       2400

GGTCGGGGAG CCTGGCGCAC TGCGGGCCGC TCCCTCTAAC CCTGGGCTTC CCTGGCGTCC      2460

AGGGCCGTCG GGGCCGAGTC CCGATTCGCT CCCACCCCGA AGCCGCGCCA GGACCAACGA      2520

GGGCGCAGCC GTATGCCCCA GCCCGCTCCG CGGAGCCCCT CACAGCCACC CCCGCCCCGA      2580

CCGCGCCCCG CGCGGCTCGA AGCACCTTCC CAAGGGGCTG GTCCTTGCGC CATAGTCGCG      2640

CCGGAGCCTC TGGAGGGACA TCAAGGATTT CTCGCTCCTA CCAGCCACCC CCAAATTTTT     2700

GGGAGGTACC CAAGGGTGCG CGCGTGGCTC CTGGCGCGCC GAGGCCCTCC CTCGAGGCCC      2760

CGCGAGGTGC ACACTGCGGG CCCAGGGCTA GCAGCCGCCC GGCACGTCGC TACCCTGAGG      2820

GGCGGGGCGG GAGCTGGCGC TAGAAATGCG CCGGGGCCTG CGGGGCAGTT GCGCAAGTTG      2880

TGATCGGGCC GCTATAAGAG GGGCGGGCAG GCATGGAGCC C                         2921

(2) INFORMATION FOR SEQ ID NO: 5:

(i) SEQUENCE CHARACTERISTICS:
        (A) LENGTH:        23 base pairs
        (B) TYPE:          nucleic acid
        (C) STRANDEDNESS:  single
        (D) TOPOLOGY:      linear (xi) SEQUENCE DESCRIPTION: SEQ ID NO: 5:

ATGCATTGGG GAACCCTGTG CGG                                              23

(2) INFORMATION FOR SEQ ID NO: 6:

(i) SEQUENCE CHARACTERISTICS:
        (A) LENGTH:        30 base pairs
        (B) TYPE:          nucleic acid
        (C) STRANDEDNESS:  single
        (D) TOPOLOGY:      linear (xi) SEQUENCE DESCRIPTION: SEQ ID NO: 6:

TGTGAAATGT CATTGATCCT GGTGACAATT                                       30

(2) INFORMATION FOR SEQ ID NO: 7:

(i) SEQUENCE CHARACTERISTICS:
        (A) LENGTH:        24 base pairs
        (B) TYPE:          nucleic acid
        (C) STRANDEDNESS:  single
        (D) TOPOLOGY:      linear (xi) SEQUENCE DESCRIPTION: SEQ ID NO: 7:

GAGGGTTTTG GTGTCATCTT GGAC                                             24

(2) INFORMATION FOR SEQ ID NO: 8:

(i) SEQUENCE CHARACTERISTICS:
        (A) LENGTH:        26 base pairs
        (B) TYPE:          nucleic acid
        (C) STRANDEDNESS:  single
        (D) TOPOLOGY:      linear
```

(xi) SEQUENCE DESCRIPTION: SEQ ID NO: 8:

CCTGCTCAGG GCCACCACCT CTGTCG                                        26

(2) INFORMATION FOR SEQ ID NO: 9:

(i) SEQUENCE CHARACTERISTICS:
        (A) LENGTH:            52 base pairs
        (B) TYPE:              nucleic acid
        (C) STRANDEDNESS:      single
        (D) TOPOLOGY:          linear (ix) FEATURE:
        (D) OTHER INFORMATION:  "N" represents any base.

(xi) SEQUENCE DESCRIPTION: SEQ ID NO: 9:

TTCTAGAATT CAGCGGCCGC TTTTTTTTTT TTTTTTTTTT TTTTTTTTTT NN           52

(2) INFORMATION FOR SEQ ID NO: 10:

(i) SEQUENCE CHARACTERISTICS:
        (A) LENGTH:            27 base pairs
        (B) TYPE:              nucleic acid
        (C) STRANDEDNESS:      single
        (D) TOPOLOGY:          linear (xi) SEQUENCE DESCRIPTION: SEQ ID NO: 10:

CCATCCTAAT ACGACTCACT ATAGGGC                                       27

(2) INFORMATION FOR SEQ ID NO: 11:

(i) SEQUENCE CHARACTERISTICS:
        (A) LENGTH:            23 base pairs
        (B) TYPE:              nucleic acid
        (C) STRANDEDNESS:      single
        (D) TOPOLOGY:          linear (xi) SEQUENCE DESCRIPTION: SEQ ID NO: 11:

ACTCACTATA GGGCTCGAGC GGC                                           23

(2) INFORMATION FOR SEQ ID NO: 12:

(i) SEQUENCE CHARACTERISTICS:
        (A) LENGTH:            31 base pairs
        (B) TYPE:              nucleic acid
        (C) STRANDEDNESS:      single
        (D) TOPOLOGY:          linear (xi) SEQUENCE DESCRIPTION: SEQ ID NO: 12:

GCCACAAGAA TCCGCACAGG GTTCCCCATG C                                  31

(2) INFORMATION FOR SEQ ID NO: 13:

(i) SEQUENCE CHARACTERISTICS:
        (A) LENGTH:            21 base pairs
        (B) TYPE:              nucleic acid
        (C) STRANDEDNESS:      single
        (D) TOPOLOGY:          linear (xi) SEQUENCE DESCRIPTION: SEQ ID NO: 13:

CTCTTAGAGA AGGCCAGCAC G                                             21

(2) INFORMATION FOR SEQ ID NO: 14:

(i) SEQUENCE CHARACTERISTICS:
        (A) LENGTH:            33 base pairs
        (B) TYPE:              nucleic acid

```
        (C) STRANDEDNESS:      single
        (D) TOPOLOGY:          linear (xi) SEQUENCE DESCRIPTION: SEQ ID NO: 14:

CGCGGGCTCG AGAAGGTCAG GATGGGGTGG AGC                                    33

(2) INFORMATION FOR SEQ ID NO: 15:

(i) SEQUENCE CHARACTERISTICS:
        (A) LENGTH:            23 base pairs
        (B) TYPE:              nucleic acid
        (C) STRANDEDNESS:      single
        (D) TOPOLOGY:          linear (xi) SEQUENCE DESCRIPTION: SEQ ID NO: 15:

CGCAGCGCCA ACGGTTGCAA GGC                                               23

(2) INFORMATION FOR SEQ ID NO: 16:

(i) SEQUENCE CHARACTERISTICS:
        (A) LENGTH:            23 base pairs
        (B) TYPE:              nucleic acid
        (C) STRANDEDNESS:      single
        (D) TOPOLOGY:          linear (xi) SEQUENCE DESCRIPTION: SEQ ID NO: 16:

GCCTTGCAAC CGTTGGCGCT GCG                                               23

(2) INFORMATION FOR SEQ ID NO: 17:

(i) SEQUENCE CHARACTERISTICS:
        (A) LENGTH:            35 base pairs
        (B) TYPE:              nucleic acid
        (C) STRANDEDNESS:      single
        (D) TOPOLOGY:          linear (xi) SEQUENCE DESCRIPTION: SEQ ID NO: 17:

CGCGGGAAGC TTGCCTTGCA ACCGTTGGCG CTGCG                                  35

(2) INFORMATION FOR SEQ ID NO: 18:

(i) SEQUENCE CHARACTERISTICS:
        (A) LENGTH:            20 base pairs
        (B) TYPE:              nucleic acid
        (C) STRANDEDNESS:      single
        (D) TOPOLOGY:          linear (xi) SEQUENCE DESCRIPTION: SEQ ID NO: 18:

GAGCCTCTGG AGGGACATCA                                                   20

(2) INFORMATION FOR SEQ ID NO: 19:

(i) SEQUENCE CHARACTERISTICS:
        (A) LENGTH:            20 base pairs
        (B) TYPE:              nucleic acid
        (C) STRANDEDNESS:      single
        (D) TOPOLOGY:          linear (xi) SEQUENCE DESCRIPTION: SEQ ID NO: 19:

TGGCGTCTTC CATGGGGTCT                                                   20

(2) INFORMATION FOR SEQ ID NO: 20:

(i) SEQUENCE CHARACTERISTICS:
        (A) LENGTH:            31 base pairs
        (B) TYPE:              nucleic acid
        (C) STRANDEDNESS:      single
```

(D) TOPOLOGY:         linear (xi) SEQUENCE DESCRIPTION: SEQ ID NO: 20:

GCCTGCGGGG CAGTTAAAAA AGTTGTGATC G                              31

(2) INFORMATION FOR SEQ ID NO: 21:

(i) SEQUENCE CHARACTERISTICS:
          (A) LENGTH:           30 base pairs
          (B) TYPE:             nucleic acid
          (C) STRANDEDNESS:     single
          (D) TOPOLOGY:         linear (xi) SEQUENCE DESCRIPTION: SEQ ID NO: 21:

CGATCACAAC TTAAAAAACT GCCCCGCAGG                                30

(2) INFORMATION FOR SEQ ID NO: 22:

(i) SEQUENCE CHARACTERISTICS:
          (A) LENGTH:           56 base pairs
          (B) TYPE:             nucleic acid
          (C) STRANDEDNESS:     single
          (D) TOPOLOGY:         linear (xi) SEQUENCE DESCRIPTION: SEQ ID NO: 22:

GCTTCTTGGG CCTTGCAACC GTTGGCGCTG CGATTCCTAC GGGGCTCCAT GCCTGC    56

(2) INFORMATION FOR SEQ ID NO: 23:

(i) SEQUENCE CHARACTERISTICS:
          (A) LENGTH:           29 base pairs
          (B) TYPE:             nucleic acid
          (C) STRANDEDNESS:     single
          (D) TOPOLOGY:         linear (xi) SEQUENCE DESCRIPTION: SEQ ID NO: 23:

CCAAGAAGAG GGATCCCTGC TCCAGCAGC                                 29

(2) INFORMATION FOR SEQ ID NO: 24:

(i) SEQUENCE CHARACTERISTICS:
          (A) LENGTH:           32 base pairs
          (B) TYPE:             nucleic acid
          (C) STRANDEDNESS:     single
          (D) TOPOLOGY:         linear (xi) SEQUENCE DESCRIPTION: SEQ ID NO: 24:

CCCTCTACAT GATTCTTGGG TACCTGGTGG CC                             32

(2) INFORMATION FOR SEQ ID NO: 25:

(i) SEQUENCE CHARACTERISTICS:
          (A) LENGTH:           93 base pairs
          (B) TYPE:             nucleic acid
          (C) STRANDEDNESS:     single
          (D) TOPOLOGY:         linear (xi) SEQUENCE DESCRIPTION: SEQ ID NO: 25:

GGCCCCTGAC CACCAGGAAC TGAACCTTGA TGCGTCCCTC CAACTGCCCA GCCGCAGCTC    60

CAAGCCAAGA AGCCCATCCT GGGAAGGAAA ATG                                93

(2) INFORMATION FOR SEQ ID NO: 26:

(i) SEQUENCE CHARACTERISTICS:
          (A) LENGTH:           19 base pairs
          (B) TYPE:             nucleic acid

```
        (C) STRANDEDNESS:      single
        (D) TOPOLOGY:          linear (xi) SEQUENCE DESCRIPTION: SEQ ID NO: 26:

CATTTTCCTT CCCAGGATG                                                    19

(2) INFORMATION FOR SEQ ID NO: 27:

(i) SEQUENCE CHARACTERISTICS:
        (A) LENGTH:            20 base pairs
        (B) TYPE:              nucleic acid
        (C) STRANDEDNESS:      single
        (D) TOPOLOGY:          linear (xi) SEQUENCE DESCRIPTION: SEQ ID NO: 27:

TGGGTGAGTA CCATAATCGC                                                   20

(2) INFORMATION FOR SEQ ID NO: 28:

(i) SEQUENCE CHARACTERISTICS:
        (A) LENGTH:            74 base pairs
        (B) TYPE:              nucleic acid
        (C) STRANDEDNESS:      single
        (D) TOPOLOGY:          linear (xi) SEQUENCE DESCRIPTION: SEQ ID NO: 28:

AAGCTTCTTT AAGGATGGAG AGGCCCTAGT GGAATGGGGA GATTCTTCCG GGAGAAGCGA        60

TGGATGCACA GTTG                                                         74

(2) INFORMATION FOR SEQ ID NO: 29:

(i) SEQUENCE CHARACTERISTICS:
        (A) LENGTH:            59 base pairs
        (B) TYPE:              nucleic acid
        (C) STRANDEDNESS:      single
        (D) TOPOLOGY:          linear (xi) SEQUENCE DESCRIPTION: SEQ ID NO: 29:

AAGCTTTAGC TAGTCTGAGT CCTCTCCCTA TACACATTCT CCTGTGGGAT CCCCTCCTG         59

(2) INFORMATION FOR SEQ ID NO: 30:

(i) SEQUENCE CHARACTERISTICS:
        (A) LENGTH:            118 base pairs
        (B) TYPE:              nucleic acid
        (C) STRANDEDNESS:      single
        (D) TOPOLOGY:          linear (ix) FEATURE:
         (D) OTHER INFORMATION:  "N" represents any base.

(xi) SEQUENCE DESCRIPTION: SEQ ID NO: 30:

GAATTCCTAC CCGCAGAGCA AGGCAATGTC TGGGACTGAG ACTGATCACT TGCATCTGCG        60

TCTCTCCTAN NCCCAACTTT ATCTCCTTCA GACTGGGTG GGACATCTGA TCTTTGGG         118

(2) INFORMATION FOR SEQ ID NO: 31:

(i) SEQUENCE CHARACTERISTICS:
        (A) LENGTH:            70 base pairs
        (B) TYPE:              nucleic acid
        (C) STRANDEDNESS:      single
        (D) TOPOLOGY:          linear (ix) FEATURE:
         (D) OTHER INFORMATION:  "N" represents any base.

(xi) SEQUENCE DESCRIPTION: SEQ ID NO: 31:
```

```
GAATTCAAAA CTTTATAGAC ACAGAAATGC AAATTTCCTG TAATTTNNCC GTTGAGAACT      60

ATTCTTCTTT                                                             70
```

(2) INFORMATION FOR SEQ ID NO: 32:

(i) SEQUENCE CHARACTERISTICS:
        (A) LENGTH:        127 base pairs
        (B) TYPE:          nucleic acid
        (C) STRANDEDNESS:  single
        (D) TOPOLOGY:     linear (ix) FEATURE:
        (D) OTHER INFORMATION:  "N" represents any base.

(xi) SEQUENCE DESCRIPTION: SEQ ID NO: 32:

```
ACTGCCCCGC NGGCCCCGGC GCATTTCTAG CGCCAGCTCC CGCCCCGCCC CTTCAGGTAG      60

CGACAGTGCC GGGCGGCTGC TAGCCCTGGG CCCGCAGTGT GCACCTCGCG GGGCCTCGAG     120

GGAGGGC                                                               127
```

(2) INFORMATION FOR SEQ ID NO: 33:

(i) SEQUENCE CHARACTERISTICS:
        (A) LENGTH:        9 base pairs
        (B) TYPE:          nucleic acid
        (C) STRANDEDNESS:  single
        (D) TOPOLOGY:     linear (xi) SEQUENCE DESCRIPTION: SEQ ID NO: 33:

```
TTGCGCAAG                                                               9
```

(2) INFORMATION FOR SEQ ID NO: 34:

(i) SEQUENCE CHARACTERISTICS:
        (A) LENGTH:        7 base pairs
        (B) TYPE:          nucleic acid
        (C) STRANDEDNESS:  single
        (D) TOPOLOGY:     linear (xi) SEQUENCE DESCRIPTION: SEQ ID NO: 34:

```
TATAAGA                                                                 7
```

(2) INFORMATION FOR SEQ ID NO: 35:

(i) SEQUENCE CHARACTERISTICS:
        (A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 35:

```
GTAAAACGAC GGCCAGT                                                     17
```

(2) INFORMATION FOR SEQ ID NO: 36:

(i) SEQUENCE CHARACTERISTICS:
        (A) LENGTH:        239 base pairs
        (B) TYPE:          nucleic acid
        (C) STRANDEDNESS:  single
        (D) TOPOLOGY:     linear (xi) SEQUENCE DESCRIPTION: SEQ ID NO: 36:

```
GGAGGTACCC AAGGGTGCGC GCGTGGCTCC TGGCGCGCCG AGGCCCTCCC TCGAGGCCCC      60

GCGAGGTGCA CACTGCGGGC CCAGGGCTAG CAGCCGCCCG GCACGTCGCT ACCCTGAGGG     120
```

```
GCGGGGCGGG AGCTGCGCTA GAAATGCGCC GGGGCCTGCG GGGCAGTTGC GCAAGTTGTG      180

ATCGGGCCGC TATAAGAGGG GCGGGCAGGC ATGGAGCCCG CAGCGCCAAC GGTTGCAAG       239
```

(2) INFORMATION FOR SEQ ID NO: 37:

(i) SEQUENCE CHARACTERISTICS:
        (A) LENGTH:        9 base pairs
        (B) TYPE:          nucleic acid
        (C) STRANDEDNESS:  single
        (D) TOPOLOGY:     linear (xi) SEQUENCE DESCRIPTION: SEQ ID NO: 37:

```
TTGCGCAAG                                                              9
```

(2) INFORMATION FOR SEQ ID NO: 38:

(i) SEQUENCE CHARACTERISTICS:
        (A) LENGTH:        9 base pairs
        (B) TYPE:          nucleic acid
        (C) STRANDEDNESS:  single
        (D) TOPOLOGY:     linear (xi) SEQUENCE DESCRIPTION: SEQ ID NO: 38:

```
TTAAAAAAG                                                              9
```

(2) INFORMATION FOR SEQ ID NO: 39:

(i) SEQUENCE CHARACTERISTICS:
        (A) LENGTH:        29 base pairs
        (B) TYPE:          nucleic acid
        (C) STRANDEDNESS:  single
        (D) TOPOLOGY:     linear (xi) SEQUENCE DESCRIPTION: SEQ ID NO: 39:

```
CCAAGAAGAG GGATCCCTGC TCCAGCAGC                                        29
```

(2) INFORMATION FOR SEQ ID NO: 40:

(i) SEQUENCE CHARACTERISTICS:
        (A) LENGTH:        29 base pairs
        (B) TYPE:          nucleic acid
        (C) STRANDEDNESS:  single
        (D) TOPOLOGY:     linear (xi) SEQUENCE DESCRIPTION: SEQ ID NO: 40:

```
CCCTCTACAT GATTCTTGGG TACCTGGCC                                        29
```

(2) INFORMATION FOR SEQ ID NO: 41:

(i) SEQUENCE CHARACTERISTICS:
        (A) LENGTH:        41 base pairs
        (B) TYPE:          nucleic acid
        (C) STRANDEDNESS:  single
        (D) TOPOLOGY:     linear (xi) SEQUENCE DESCRIPTION: SEQ ID NO: 41:

```
CGGTTGCAAG GCCCAAGAAG CCCATCCTGG GAAGGAAAAT G                          41
```

(2) INFORMATION FOR SEQ ID NO: 42:

(i) SEQUENCE CHARACTERISTICS:
        (A) LENGTH:        52 base pairs
        (B) TYPE:          nucleic acid
        (C) STRANDEDNESS:  single
        (D) TOPOLOGY:     linear (xi) SEQUENCE DESCRIPTION: SEQ ID NO: 42:

```
CGCAGCGCCA ACGGTTGCAA GGCCCAAGAA GCCCATCCTG GGAAGGAAAA TG                    52
```

(2) INFORMATION FOR SEQ ID NO: 43:

(i) SEQUENCE CHARACTERISTICS:
        (A) LENGTH:       49 base pairs
        (B) TYPE:         nucleic acid
        (C) STRANDEDNESS:  single
        (D) TOPOLOGY:     linear (xi) SEQUENCE DESCRIPTION: SEQ ID NO: 43:

```
AGCGCCAACG GTTGCAAGGC CCAAGAAGCC CATCCTGGGA AGGAAAATG                        49
```

(2) INFORMATION FOR SEQ ID NO: 44:

(i) SEQUENCE CHARACTERISTICS:
        (A) LENGTH:       48 base pairs
        (B) TYPE:         nucleic acid
        (C) STRANDEDNESS:  single
        (D) TOPOLOGY:     linear (xi) SEQUENCE DESCRIPTION: SEQ ID NO: 44:

```
AGCGCCAACG GTTGCAAGGC CCAAGAAGCC ATCCTGGGAA GGAAAATG                         48
```

(2) INFORMATION FOR SEQ ID NO: 45:

(i) SEQUENCE CHARACTERISTICS:
        (A) LENGTH:       52 base pairs
        (B) TYPE:         nucleic acid
        (C) STRANDEDNESS:  single
        (D) TOPOLOGY:     linear (xi) SEQUENCE DESCRIPTION: SEQ ID NO: 45:

```
CGCAGCGCCA ACGGTTGCAA GGCCCAAGAA GCCCATCCTG GGAAGGAAAA TG                    52
```

(2) INFORMATION FOR SEQ ID NO: 46:

(i) SEQUENCE CHARACTERISTICS:
        (A) LENGTH:       58 base pairs
        (B) TYPE:         nucleic acid
        (C) STRANDEDNESS:  single
        (D) TOPOLOGY:     linear (xi) SEQUENCE DESCRIPTION: SEQ ID NO: 46:

```
CTTGCAGTGT GTGTTCCTTC TGTGTCAGCC CAAGAAGCCC ATCCTGGGAA GGAAAATG             58
```

(2) INFORMATION FOR SEQ ID NO: 47:

(i) SEQUENCE CHARACTERISTICS:
        (A) LENGTH:       30 base pairs
        (B) TYPE:         nucleic acid
        (C) STRANDEDNESS:  single
        (D) TOPOLOGY:     linear (xi) SEQUENCE DESCRIPTION: SEQ ID NO: 47:

```
CGTAGGAATC GCAGCGCCAA CGGTTGCAAG                                             30
```

(2) INFORMATION FOR SEQ ID NO: 48:

(i) SEQUENCE CHARACTERISTICS:
        (A) LENGTH:        29 base pairs
        (B) TYPE:          nucleic acid
        (C) STRANDEDNESS:  single
        (D) TOPOLOGY:     linear (xi) SEQUENCE DESCRIPTION: SEQ ID NO: 48:

GGAGGAATCC CTGCTCCAGC AGCTGCAAG                                                29